United States Patent
Takyo et al.

(10) Patent No.: US 7,759,291 B2
(45) Date of Patent: Jul. 20, 2010

(54) PYRAZOLE COMPOUNDS AND USE THEREOF

(75) Inventors: Hayato Takyo, Toyonaka (JP); Masaya Hashizume, Yokohama (JP); Noriyasu Sakamoto, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1047 days.

(21) Appl. No.: 10/585,639

(22) PCT Filed: Jan. 25, 2005

(86) PCT No.: PCT/JP2005/001309

§ 371 (c)(1),
(2), (4) Date: Jul. 7, 2006

(87) PCT Pub. No.: WO2005/075433

PCT Pub. Date: Aug. 18, 2005

(65) Prior Publication Data

US 2009/0192208 A1  Jul. 30, 2009

(30) Foreign Application Priority Data

Feb. 5, 2004 (JP) ............................. 2004-029041
Sep. 22, 2004 (JP) ............................. 2004-274835

(51) Int. Cl.
  *A01N 43/56* (2006.01)
  *C07D 231/10* (2006.01)
(52) U.S. Cl. .................. 504/282; 548/366.1; 548/377.1
(58) Field of Classification Search .................. 504/282; 548/366.1, 377.1
See application file for complete search history.

(56) References Cited

U.S. PATENT DOCUMENTS

| 4,843,068 | A | 6/1989 | Hamaguchi et al. |
| 2004/0142820 | A1 | 7/2004 | Ebenbeck et al. |
| 2006/0142367 | A1 | 6/2006 | Hashizume et al. |

FOREIGN PATENT DOCUMENTS

| EP | 0 376 598 A2 | 7/1990 |
| EP | 0 648 729 A1 | 4/1995 |
| JP | 62-53970 A | 3/1987 |
| JP | 63-183564 A | 7/1988 |
| WO | WO-2004/085405 A1 | 10/2004 |

*Primary Examiner*—Kamal A Saeed
*Assistant Examiner*—Samantha L Shterengarts
(74) *Attorney, Agent, or Firm*—Birch, Stewart, Kolasch & Birch, LLP

(57) ABSTRACT

The present invention provides a pyrazole compound of formula (a): a noxious arthropod pests controlling composition containing the compound shown by the formula (a) as an active ingredient; and a method for controlling noxious arthropod pests comprising applying an effective amount of the compound shown by the formula (a).

(a)

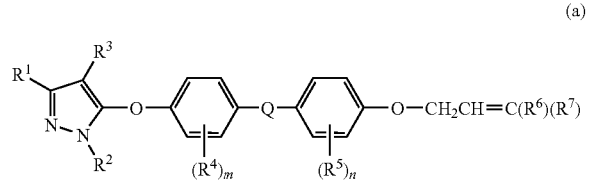

15 Claims, No Drawings

PYRAZOLE COMPOUNDS AND USE THEREOF

TECHNICAL FIELD

The present invention relates to pyrazole compounds, their use, and intermediate compounds.

BACKGROUND ART

Various compound have been developed and used for active ingredient of noxious arthropod pests controlling composition.

On the other hand, a certain type of pyrazole compounds is known as a intermediate of medically and pesticidal active compounds, and fungicidally active compounds. See Japanese Laid-Open patent specification No. sho 62-53970A.

DISCLOSURE OF INVENTION

The present invention provides a pyrazole compound of formula (a) (hereinafter, referred as the compound of the present invention):

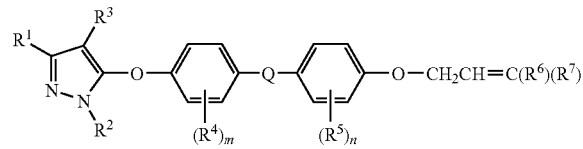

(a)

wherein,
$R^1$ represents a hydrogen atom, a C1 to C4 alkyl group or a trifluoromethyl group,
$R^2$ represents a C1 to C4 alkyl group,
$R^3$ represents a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group, a halogen atom or a cyano group,
$R^4$ represents a halogen atom, a C1 to C3 alkyl group, a C1 to C3 alkoxy group, a C1 to C3 haloalkyl group or a C1 to C3-haloalkoxy group,
m represents an integer of 0 to 4 and when m is an integer of 2 to 4, each of $R^4$s may be the same or different,
$R^5$ represents a halogen atom, a C1 to C3 alkyl group, a C1 to C3 alkoxy group, a C1 to C3 haloalkyl group or a C1 to C3 haloalkoxy group,
n represents an integer of 0 to 4 and when n is an integer of 2 to 4, each of $R^5$s may be the same or different,
each of $R^6$ and $R^7$ may be the same or different and represents a hydrogen atom, a halogen atom or a methyl group,
Q represents an oxygen atom, a sulfur atom or a C1 to C5 alkylidene group;
a noxious arthropod pests controlling composition comprising the compound of the present invention as an active ingredient and an inert carrier; and a method for controlling noxious arthropod pests comprising applying an effective amount of the compound of the present invention to noxious arthropod pests or habitat noxious arthropod pests.

Furthermore, the present invention also provides a compound of formula (b) (hereinafter, referred as the intermediate compound of the present invention):

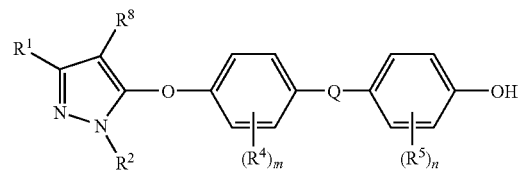

(b)

wherein,
$R^1$ represents a hydrogen atom, a C1 to C4 alkyl group or a trifluoromethyl group,
$R^2$ represents a C1 to C4 alkyl group,
$R^8$ represents a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group, a carboxyl group, a halogen atom or a cyano group,
$R^4$ represents a halogen atom, a C1 to C3 alkyl group, a C1 to C3 alkoxy group, a C1 to C3 haloalkyl group or a C1 to C3 haloalkoxy group,
m represents an integer of 0 to 4 and when m is an integer of 2 to 4, each of $R^4$s may be the same or different,
$R^5$ represents a halogen atom, a C1 to C3 alkyl group, a C1 to C3 alkoxy group, a C1 to C3 haloalkyl group or a C1 to C3 haloalkoxy group,
n represents an integer of 0 to 4 and when n is an integer of 2 to 4, each of $R^5$s may be the same or different,
Q represents an oxygen atom, a sulfur atom or a C1 to C5 alkylidene group;

which is useful as an intermediate of the compound of the present invention.

MODE OF CARRYING OUT THE INVENTION

In the present invention, the description of "a C2 to C6" in "a C2 to C6 alkoxycarbonyl group" or the like means the total number of carbon atoms which constitutes the substituent.

In the compound of the present invention, the C1 to C4 alkyl group represented by $R^1$ and $R^2$ includes a methyl group, an ethyl group, a propyl group, anisopropyl group, a butyl group, an isobutyl group, a sec-butyl group and a tert-butyl group.

The C1 to C6 alkyl group represented by $R^3$ and $R^8$ includes, for example, a methyl group, an ethyl group, a propyl group, an isopropyl group, a butyl group, an isobutyl group, a sec-butyl group, a pentyl group, an isopentyl group, a neopentyl group, a 1-methylbutyl group, a 2-methylbutyl group, a 1,2-dimethylpropyl group and a hexyl group;
the C1 to C6 haloalkyl group includes, for example, a fluoromethyl group, a difluoromethyl group, a trifluoromethyl group, a 2-fluoroethyl group, a 2,2,2-trifluoroethyl group, a 3-fluoropropyl group, a 3,3,3-trifluoropropyl group, a 4-fluorobutyl group, a 4,4,4-trifluorobutyl group, a 5,5,5-trifluoropentyl group, a 2-chloroethyl group, a 1,2-dichloroethyl group, a 2-bromoethyl group, a 1,2-dibromoethyl group, a 3-chloropropyl group, a 2,3-dichloropropyl group, a 3-bromopropyl group, a 2,3-dibromopropyl group, a 4-chlorobutyl group, a 4-bromobutyl group, a 5-choloropentyl group, a 5-bromopentyl group, a 6-cholorohexyl group and a 6-bromohexyl group;

the C2 to C6 alkenyl group includes, for example, a vinyl group, an allyl group, a 1-propenyl group, an isopropenyl group, a 1-butenyl group, a 2-butenyl group, a 3-butenyl group, a 1-methyl-1-propenyl group, a 1-methyl-2-propenyl group, a 2-methyl-1-propenyl group, a 2-methyl-2-propenyl group, an isobutenyl group, a 1-pentenyl group, a 1-methyl-1-butenyl group, a 1-methyl-2-butenyl group, a 1-methyl-3-butenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,2-dimethyl-1-propenyl group and a 1-hexenyl group;

the C2 to C6 haloalkenyl group includes, for example, a 2-chlorovinyl group, a 2,2-dichlorovinyl group, a 2-chloro-1-propenyl group, a 3-chloro-2-propenyl group, a 2,3-dichloro-2-propenyl group, a 3,3-dichloro-2-propenyl group, a 2-bromovinyl group, a 2,2-dibromovinyl group, a 2-bromo-1-propenyl group, a 3-bromo-2-propenyl group, a 3,3-dibromo-2-propenyl group, a 2,3-dichloro-2-propenyl group, a 3-chloro-2-butenyl group, a 3-chloro-4,4,4-trifuluoro-2-butenyl group, a 3-bromo-2-butenyl group, a 3,3,3-trifluoro-1-propenyl group, a 4,4,4-trifluoro-1-butenyl group and a 5,5,5-trifluoro-2-pentenyl group;

the C2 to C6 alkynyl group includes, for example, an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group and a 4-hexynyl group;

the C2 to C6 haloalkynyl group includes, for example, a 2-chloroethynyl group, a 3-chloro-2-propynyl group, a 4-chloro-3-butynyl group, a 5-chloro-4-pentynyl group, a 6-choloro-5-hexynyl group, a 2-bromoethynyl group, a 3-bromo-2-propynyl group, a 4-bromo-3-butynyl group, a 5-bromo-4-pentynyl group and a 6-bromo-5-hexynyl group;

the C1 to C5 hydroxyalkyl group includes, for example, a hydroxymethyl group, a 1-hydroxyethyl group, a 3-hydroxypropyl group, a 2-hydroxyethyl group, a 4-hydroxybuthyl group and a 5-hydroxypentyl group;

the C2 to C6 alkoxyalkyl group includes, for example, a methoxymethyl group, an ethoxymethyl group, a propoxymethyl group, an isopropoxymethyl group, a buthoxymethyl group, a penthyloxymethyl group, a 1-methoxyethyl group, a 2-methoxyethyl group, a 2-ethoxyethyl group, a 2-propoxyethyl group, a 2-isopropoxyethyl group and a 3-ethoxypropyl group;

the C2 to C6 alkoxycarbonyl group includes, for example, a methoxycarbonyl group, an ethoxycarbonyl group, a propoxycarbonyl group, an isopropoxycarbonyl group, a butoxycarbonyl group and a tert-butoxycarbonyl group;

the C4 to C6 alkenyoxycarbonyl group includes, for example, a 2-propenyloxycarbonyl group, a 1-methyl-2-propenyloxycarbonyl group, a 2-methyl-2-propenyloxycarbonyl group, a 2-butenyloxycarbonyl group, a 1-methyl-2-butenyloxycarbonyl group, a 2-methyl-2-butenyloxycarbonyl group and a 3-methyl-2-butenyloxycarbony group;

the C4 to C6 haloalkenyoxycarbonyl group includes, for example, a 3-chloro-2-propenyloxycarbonyl group, a 3,3-dichloro-2-propenyloxycarbonyl group, a 3-chloro-2-butenyloxycarbonyl group, a 3-bromo-2-propenyloxycarbonyl group, a 3,3-dibromo-2-propenyloxycarbonyl group and a 3-bromo-2-butenyloxycarbonyl group;

the halogen atom includes a fluorine atom, a chlorine atom, a bromine atom and an iodine atom.

The halogen atom represented by $R^4$ and $R^5$ includes a fluorine atom, a chlorine atom, a bromine atom and an iodine atom;

the C1 to C3 alkyl group includes a methyl group, an ethyl group, a propyl group and an isopropyl group;

the C1 to C3 alkoxy group includes a methoxy group, an ethoxy group, a propoxy group and an isopropoxy group;

the C1 to C3 haloalkyl group includes a trifluoromethyl group, a 2-fluoroethyl group, a 2,2,2-trifluoroethyl group, a 3,3,3-trifluoropropyl group, a 2-chloroethyl group and a 3-bromopropyl group;

the C1 to C3 haloalkoxy group includes a trifluoromethoxy group, a 2,2,2-trifluoroethoxy group and a 3,3,3-trifluoropropoxy group.

The halogen atom represented by $R^6$ includes a fluorine atom, a chlorine atom, a bromine atom and an iodine atom.

The halogen atom represented by $R^7$ includes a fluorine atom, a chlorine atom, a bromine atom and an iodine atom.

The C1 to C5 alkylidene group represented by Q includes, for example, a methylene group, an ethylene group, a propylidene group, a buthylidene group, a butane-2-ylidene group, a pentane-2-ylidene group and a pentane-3-ylidene group.

The embodiments of the compound of the present invention are exemplified followings:

the pyrazole compound wherein $R^1$ is a methyl group or an ethyl group in the formula (a);

the pyrazole compound wherein $R^1$ is a methyl group or a trifluoromethyl group in the formula (a);

the pyrazole compound wherein $R^1$ is a methyl group in the formula (a);

the pyrazole compound wherein $R^2$ is a methyl group in the formula (a);

the pyrazole compound wherein $R^3$ is a hydrogen atom or a cyano group in the formula (a);

the pyrazole compound wherein $R^3$ is a C1 to C6 alkyl group, a C2 to C6 alkenyl group or a C2 to C6 alkynyl group in the formula (a);

the pyrazole compound wherein $R^3$ is a C1 to C6 haloalkyl group, a C2 to C6 haloalkenyl group or a C2 to C6 haloalkynyl group in the formula (a);

the pyrazole compound wherein $R^3$ is a C1 to C6 alkyl group, a C1 to C6 haloalkyl group or a C2 to C6 alkoxycarbonyl group in the formula (a);

the pyrazole compound wherein $R^3$ is a C2 to C6 alkenyl group, a C2 to C6 haloalkenyl group, a C4 to C6 alkenyloxycarbonyl group or a C4 to C6 haloalkenyloxycarbonyl group in the formula (a);

the pyrazole compound wherein $R^3$ is a C1 to C5 hydroxyalkyl group or a C2 to C6 alkoxyalkyl group in the formula (a);

the pyrazole compound wherein $R^3$ is a C4 to C6 alkenyloxycarbonyl group or a C4 to C6 haloalkenyloxycarbonyl group in the formula (a);

the pyrazole compound wherein m is an integer 0 in the formula (a);

the pyrazole compound wherein n is an integer 0 in the formula (a)

the pyrazole compound wherein $R^6$ is a chlorine atom in the formula (a);

the pyrazole compound wherein $R^6$ and $R^7$ are chlorine atoms in the formula (a);

the pyrazole compound wherein $R^3$ is a C1 to C6 alkyl group, a C1 to C6 haloalkyl group, a C2 to C6 alkenyl group or a C2 to C6 alkynyl group in the formula (a);

the pyrazole compound wherein $R^3$ is a halogen atom in the formula (a);

the pyrazole compound wherein $R^1$ is a C1 to C4 alkyl group or a trifluoromethyl group in the formula (a);

the pyrazole compound wherein $R^1$ is a C1 to C4 alkyl group or a trifluoromethyl group, and $R^3$ is a C1 to C6 alkyl group, a C1 to C6 haloalkyl group, a C2 to C6 alkenyl group or a C2 to C6 alkynyl group in the formula (a);

the pyrazole compound wherein $R^1$ is a C1 to C4 alkyl group or a trifluoromethyl group, and $R^3$ is a halogen atom in the formula (a);

the pyrazole compound wherein $R^1$ is a hydrogen atom in the formula (a);

the pyrazole compound wherein $R^1$ is a hydrogen atom, $R^3$ is a C1 to C6 alkyl group, a C1 to C6 haloalkyl group, a C2 to C6 alkenyl group or a C2 to C6 alkynyl group in the formula (a);

the pyrazole compound wherein $R^1$ is a halogen atom, and $R^3$ is a halogen atom in the formula (a);

the pyrazole compound wherein Q is an oxygen atom in the formula (a);

the pyrazole compound wherein $R^3$ is a C1 to C6 alkyl group, a C1 to C6 haloalkyl group, a C2 to C6 alkenyl group or a C2 to C6 alkynyl group, and Q is an oxygen atom in the formula (a);

the pyrazole compound wherein $R^3$ is a halogen atom, and Q is an oxygen atom in the formula (a);

the pyrazole compound wherein $R^1$ is a C1 to C4 alkyl group or a trifluoromethyl group, and Q is an oxygen atom in the formula (a);

the pyrazole compound wherein $R^1$ is a C1 to C4 alkyl group or a trifluoromethyl group, and $R^3$ is a C1 to C6 alkyl group, a C1 to C6 haloalkyl group, a C2 to C6 alkenyl group or a C2 to C6 alkynyl group, and Q is an oxygen atom in the formula (a);

the pyrazole compound wherein $R^1$ is a C1 to C4 alkyl group or a trifluoromethyl group, and $R^3$ is a halogen atom, and Q is an oxygen atom in the formula (a);

the pyrazole compound wherein $R^1$ is a hydrogen atom, and Q is an oxygen atom in the formula (a);

the pyrazole compound wherein $R^1$ is a hydrogen atom, $R^3$ is a C1 to C6 alkyl group, a C1 to C6 haloalkyl group, a C2 to C6 alkenyl group or a C2 to C6 alkynyl group, and Q is an oxygen atom in the formula (a);

the pyrazole compound wherein $R^1$ is a halogen atom, $R^3$ is a halogen atom, and Q is an oxygen atom in the formula (a);

the pyrazole compound wherein Q is a sulfur atom or a C1 to C5 alkylidene group in the formula (a);

the pyrazole compound wherein $R^3$ is a C1 to C6 alkyl group, a C1 to C6 haloalkyl group, a C2 to C6 alkenyl group or a C2 to C6 alkynyl group, and Q is a sulfur atom or a C1 to C5 alkylidene group in the formula (a);

the pyrazole compound wherein $R^3$ is a halogen atom, and Q is a sulfur atom or a C1 to C5 alkylidene group in the formula (a);

the pyrazole compound wherein $R^1$ is a C1 to C4 alkyl group or a trifluoromethyl group, and Q is a sulfur atom or a C1 to C5 alkylidene group in the formula (a);

the pyrazole compound wherein $R^1$ is a C1 to C4 alkyl group or a trifluoromethyl group, and $R^3$ is a C1 to C6 alkyl group, a C1 to C6 haloalkyl group, a C2 to C6 alkenyl group or a C2 to C6 alkynyl group, and Q is a sulfur atom or a C1 to C5 alkylidene group in the formula (a);

the pyrazole compound wherein $R^1$ is a C1 to C4 alkyl group or a trifluoromethyl group, and $R^3$ is a halogen atom, and Q is a sulfur atom or a C1 to C5 alkylidene group in the formula (a);

the pyrazole compound wherein $R^1$ is a hydrogen atom, and Q is a sulfur atom or a C1 to C5 alkylidene group in the formula (a);

the pyrazole compound wherein $R^1$ is a hydrogen atom, $R^3$ is a C1 to C6 alkyl group, a C1 to C6 haloalkyl group, a C2 to C6 alkenyl group or a C2 to C6 alkynyl group, and Q is a sulfur atom or a C1 to C5 alkylidene group in the formula (a);

the pyrazole compound wherein $R^1$ is a halogen atom, $R^3$ is a halogen atom, and Q is a sulfur atom or a C1 to C5 alkylidene group in the formula (a);

the pyrazole compound wherein $R^1$ is a methyl group or an ethyl group and $R^2$ is a methyl group in the formula (a);

the pyrazole compound wherein $R^1$ is a methyl group or a trifluoromethyl group and $R^2$ is a methyl group in the formula (a);

the pyrazole compound wherein $R^1$ is a methyl group and $R^2$ is a methyl group in the formula (a);

the pyrazole compound wherein $R^1$ is a methyl group or an ethyl group and $R^6$ is a chlorine atom in the formula (a);

the pyrazole compound wherein $R^1$ is a methyl group or a trifluoromethyl group and $R^6$ is a chlorine atom in the formula (a);

the pyrazole compound wherein $R^1$ is a methyl group and $R^6$ is a chlorine atom in the formula (a);

the pyrazole compound wherein $R^1$ is a methyl group or an ethyl group and $R^6$ and $R^7$ are chlorine atoms in the formula (a);

the pyrazole compound wherein $R^1$ is a methyl group or a trifluoromethyl group and $R^6$ and $R^7$ are chlorine atoms in the formula (a);

the pyrazole compound wherein $R^1$ is a methyl group and $R^6$ and $R^7$ are chlorine atoms in the formula (a);

the pyrazole compound wherein $R^1$ is a methyl group or an ethyl group and Q is an oxygen atom in the formula (a);

the pyrazole compound wherein $R^1$ is a methyl group or a trifluoromethyl group and Q is an oxygen atom in the formula (a);

the pyrazole compound wherein $R^1$ is a methyl group and Q is an oxygen atom in the formula (a);

the pyrazole compound wherein $R^1$ is a methyl group or an ethyl group, $R^2$ is a methyl group, and $R^6$ is a chlorine atom in the formula (a);

the pyrazole compound wherein $R^1$ is a methyl group or a trifluoromethyl group, $R^2$ is a methyl group, and $R^6$ is a chlorine atom in the formula (a);

the pyrazole compound wherein $R^1$ is a methyl group, $R^2$ is a methyl group, and $R^6$ is a chlorine atom in the formula (a);

the pyrazole compound wherein $R^1$ is a methyl group or an ethyl group, $R^2$ is a methyl group, and $R^6$ and $R^7$ are chlorine atoms in the formula (a);

the pyrazole compound wherein $R^1$ is a methyl group or a trifluoromethyl group, $R^2$ is a methyl group, and $R^6$ and $R^7$ are chlorine atoms in the formula (a);

the pyrazole compound wherein $R^1$ is a methyl group, $R^2$ is a methyl group, and $R^6$ and $R^7$ are chlorine atoms in the formula (a);

the pyrazole compound wherein $R^1$ is a methyl group or an ethyl group, $R^2$ is a methyl group, and Q is an oxygen atom in the formula (a);

the pyrazole compound wherein $R^1$ is a methyl group or a trifluoromethyl group, $R^2$ is a methyl group, and Q is an oxygen atom in the formula (a);

the pyrazole compound wherein $R^1$ is a methyl group, $R^2$ is a methyl group, and Q is an oxygen atom in the formula (a);

the pyrazole compound wherein $R^1$ is a methyl group or an ethyl group, $R^2$ is a methyl group, m is an integer 0 and n is an integer 0 in the formula (a);

the pyrazole compound wherein $R^1$ is a methyl group or a trifluoromethyl group, $R^2$ is a methyl group, m is an integer 0 and n is an integer 0 in the formula (a);

the pyrazole compound wherein $R^1$ is a methyl group, $R^2$ is a methyl group, m is an integer 0 and n is an integer 0 in the formula (a);

the pyrazole compound wherein $R^1$ is a methyl group or an ethyl group, $R^2$ is a methyl group, m is an integer 0, n is an integer 0 and $R^6$ is a chlorine atom in the formula (a);

the pyrazole compound wherein $R^1$ is a methyl group or a trifluoromethyl group, $R^2$ is a methyl group, m is an integer 0, n is an integer 0 and $R^6$ is a chlorine atom in the formula (a);

the pyrazole compound wherein $R^1$ is a methyl group, $R^2$ is a methyl group, m is an integer 0, n is an integer 0 and $R^6$ is a chlorine atom in the formula (a);

the pyrazole compound wherein $R^1$ is a methyl group or an ethyl group, $R^2$ is a methyl group, m is an integer 0, n is an integer 0 and Q is an oxygen atom in the formula (a);

the pyrazole compound wherein $R^1$ is a methyl group or a trifluoromethyl group, $R^2$ is a methyl group, m is an integer 0, n is an integer 0 and Q is an oxygen atom in the formula (a);

the pyrazole compound wherein $R^1$ is a methyl group, $R^2$ is a methyl group, m is an integer 0, n is an integer 0 and Q is an oxygen atom in the formula (a);

the pyrazole compound where in m is an integer 0 and n is an integer 0 in the formula (a);

the pyrazole compound wherein m is an integer 0, n is an integer 0 and $R^6$ is a chlorine atom in the formula (a);

the pyrazole compound wherein m is an integer 0, n is an integer 0 and $R^6$ and $R^7$ are chlorine atoms in the formula (a);

the pyrazole compound wherein m is an integer 0, n is an integer 0 and Q is an oxygen atom in the formula (a);

the pyrazole compound wherein $R^1$ is a C1 to C4 alkyl group or a trifluoromethyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group and Q is an oxygen atom in the formula (a);

the pyrazole compound wherein $R^1$ is a methyl group or an ethyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group and Q is an oxygen atom in the formula (a);

the pyrazole compound wherein $R^1$ is a methyl group or a trifloromethyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group and Q is an oxygen atom in the formula (a);

the pyrazole compound wherein $R^1$ is a methyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group and Q is an oxygen atom in the formula (a);

the pyrazole compound wherein $R^1$ is a methyl group or an ethyl group, $R^3$ is a C1 to C6 alkyl group, a C1 to C6 haloalkyl group, a C2 to C6 alkenyl group, a C2 to C6 alkynyl group and Q is an oxygen atom in the formula (a);

the pyrazole compound wherein $R^1$ is a methyl group or a trifluoromethyl group, $R^3$ is a C1 to C6 alkyl group, a C1 to C6 haloalkyl group, a C2 to C6 alkenyl group, a C2 to C6 alkynyl group and Q is an oxygen atom in the formula (a);

the pyrazole compound wherein $R^1$ is a methyl group, $R^3$ is a C1 to C6 alkyl group, a C1 to C6 haloalkyl group, a C2 to C6 alkenyl group, a C2 to C6 alkynyl group and Q is an oxygen atom in the formula (a);

the pyrazole compound wherein $R^1$ is a C1 to C4 alkyl group or a trifluoromethyl group, $R^3$ is a C1 to C6 alkyl group, a C1 to C6 haloalkyl group, a C2 to C6 alkenyl group, a C2 to C6 alkynyl group and Q is an oxygen atom in the formula (a);

the pyrazole compound wherein $R^1$ is a C1 to C4 alkyl group or a trifluoromethyl group, $R^2$ is a methyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group and Q is an oxygen atom in the formula (a);

the pyrazole compound wherein $R^1$ is a C1 to C4 alkyl group or a trifluoromethyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group, m is an integer 0, n is an integer 0 and Q is an oxygen atom in the formula (a);

the pyrazole compound wherein $R^1$ is a C1 to C4 alkyl group or a trifluoromethyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group, $R^6$ is a chlorine atom and Q is an oxygen atom in the formula (a);

the pyrazole compound wherein $R^1$ is a C1 to C4 alkyl group or a trifluoromethyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2, to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group, $R^6$ is a chlorine atom, $R^7$ is a chlorine atom and Q is an oxygen atom in the formula (a);

the pyrazole compound wherein $R^1$ is a C1 to C4 alkyl group or a trifluoromethyl group, $R^3$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group, m is an integer 0, n is an integer 0, $R^6$ is a chlorine atom, $R^7$ is a chlorine atom and Q is an oxygen atom in the formula (a);

the pyrazole compound wherein $R^1$ is a methyl group, $R^3$ is a C1 to C6 alkyl group, a C1 to C6 haloalkyl group, a C2 to C6 alkenyl group or a C2 to C6 alkynyl group, m is an integer 0, n is an integer 0 and Q is an oxygen atom in the formula (a); the pyrazole compound wherein $R^1$ is a methyl group, $R^3$ is a C1 to C6 alkyl group, a C1 to C6 haloalkyl group, a C2 to C6 alkenyl group or a C2 to C6 alkynyl group, $R^6$ is a chlorine atom, $R^7$ is a chlorine atom and Q is an oxygen atom in the formula (a);

the pyrazole compound wherein $R^1$ is a methyl group, $R^3$ is a C1 to C6 alkyl group, a C1 to C6 haloalkyl group, a C2 to C6 alkenyl group or a C2 to C6 alkynyl group, m is an integer 0, n is an integer 0, $R^6$ is a chlorine atom, $R^7$ is a chlorine atom and Q is an oxygen atom in the formula (a).

The embodiments of the intermediate compound of the present invention are exemplified followings:

the compound wherein $R^8$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group in the formula (b);

the compound wherein $R^8$ is a C1 to C6 alkyl group, a C2 to C6 alkenyl group or a C2 to C6 alkynyl group in the formula (b);

the compound wherein $R^8$ is a C1 to C6 haloalkyl group, a C2 to C6 haloalkenyl group or a C2 to C6 haloalkynyl group in the formula (b);

the compound wherein $R^8$ is a C1 to C6 alkyl group, a C1 to C6 haloalkyl group or a C2 to C6 alkoxycarbonyl group in the formula (b);

the compound wherein $R^8$ is a C2 to C6 alkenyl group, a C2 to C6 haloalkenyl group, a C4 to C6 alkenyloxycarbonyl group or a C4 to C6 haloalkenyloxycarbonyl group in the formula (b);

the compound wherein $R^8$ is a carbxyl group in the formula (b);

the compound wherein Q is an oxygen atom in the formula (b);

the compound wherein $R^1$ is a C1 to C4 alkyl group or a trifluoromethyl group, $R^8$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group a carboxyl group or a cyano group and Q is an oxygen atom in the formula (b);

the compound wherein $R^1$ is a C1 to C4 alkyl group or a trifluoromethyl group, $R^8$ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group and Q is an oxygen atom in the formula (b);

the compound wherein $R^1$ is a C1 to C4 alkyl group or a trifluoromethyl group, $R^8$ is a carboxyl group and Q is an oxygen atom in the formula (b);

the compound wherein $R^1$ is a C1 to C4 alkyl group or a trifluoromethyl group, $R^8$ is a C1 to C6 alkyl group, a C2 to C6 alkenyl group or a C2 to C6 alkynyl group and Q is an oxygen atom in the formula (b);

the compound wherein $R^1$ is a C1 to C4 alkyl group or a trifluoromethyl group, $R^8$ is C1 to C6 haloalkyl group, C2 to C6 haloalkenyl group or a C2 to C6 haloalkynyl group and Q is an oxygen atom in the formula (b);

the compound wherein $R^1$ is a C1 to C4 alkyl group or a trifluoromethyl group, $R^8$ is a C1 to C6 alkyl group, a C1 to C6 haloalkyl group or a C2 to C6 alkoxycarbonyl group and Q is an oxygen atom in the formula (b);

the compound wherein $R^1$ is a C1 to C4 alkyl group or a trifluoromethyl group, $R^8$ is a C2 to C6 alkenyl group, a C2 to C6 haloalkenyl group, a C4 to C6 alkenyloxycarbonyl group or a C4 to C6 haloalkenyloxycarbonyl group and Q is an oxygen atom in the formula (b).

The compound of the present invention can be produced by the following method such as Production Method 1 to Production Method 8.

Production Method 1

A method of carrying out a reaction of the inetrmediate compound of the present invention, which is shown by the formula (b-x):

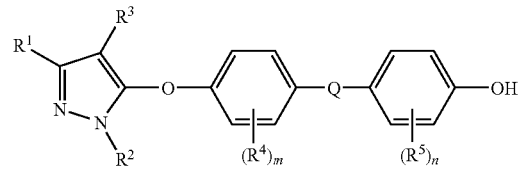

(b-x)

wherein $R^1$ represents a hydrogen atom, a C1 to C4 alkyl group or a trifluoromethyl group, $R^2$ represents a C1 to C4 alkyl group, $R^3$ represents a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group, a halogen atom or a cyano group, $R^4$ represents a halogen atom, a C1 to C3 alkyl group, a C1 to C3 alkoxy group, a C1 to C3 haloalkyl group or a C1 to C3 haloalkoxy group, m represents an integer of 0 to 4 and when m is an integer of 2 to 4, each of $R^4$s may be the same or different, $R^5$ represents a halogen atom, a C1 to C3 alkyl group, a C1 to C3 alkoxy group, a C1 to C3 haloalkyl group or a C1 to C3 haloalkoxy group, n represents an integer of 0 to 4 and when n is an integer of 2 to 4, each of $R^5$s may be the same or different;

and the compound shown by the formula (c)

$L-CH_2CH=C(R^6)(R^7)$ (c)

wherein each of $R^6$ and $R^7$ maybe the same or different and represents a hydrogen atom, a halogen atom or a methyl group, and L represents a halogen atom (such as a chlorine atom or bromine atom), methanesulfonyloxy group, benzensulfonyloxy group or toluenesulfonyloxy group.

The reaction is carried out in the presence of a base usually in a solvent.

Examples of the solvents used for the reaction include ketones such as acetone, methyl ethyl ketone and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformamide, N,N-diethylacetamide and so on; nitrites such as acetonitrile and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), hydrides of alkali metal or alkaline earth metal (sodium hydride, potassium hydride, calcium hydride and so on), carbonates of alkali metal or alkaline earth metal (sodium carbonate, potassium carbonate and so on); and organic bases such as triethylamine and so on.

The amount of the reagents to be used in the reaction is usually 1 to 3 moles of the compound shown by the formula (c) and 1 to 3 moles of the base based on one mole of the compound shown by the formula (b-x). The reaction temperature is usually in the range of −78 to 150° C., and the reaction period is usually in the range of 0.1 to 24 hours.

After the reaction, the compound of the present invention can be isolated, for example, by subjecting the reaction mixture to post-treatment, such as the reaction mixture is poured into water, extracted with an organic solvent, the organic layer is dried and concentrated and the like.

The isolated compound of the present invention can be purified by a technique such as chromatography, recrystallization and the like.

Production Method 2

A production method of the compound of the present invention, wherein $R^3$ is a cyano group.

The compound of the present invention, which is shown by the formula (d):

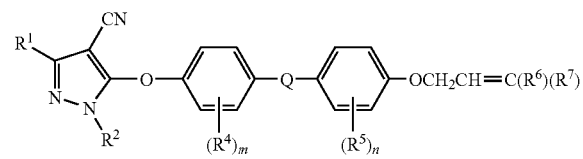

(d)

wherein $R^1$, $R^2$, $R^4$, $R^5$, $R^6$, $R^7$, Q, m and n have the same meaning as described above;

can be produced by dehydration reaction of the compound shown by the formula (e):

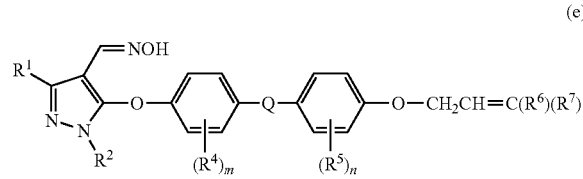

(e)

wherein $R^1$, $R^2$, $R^4$, $R^5$, $R^6$, $R^7$, Q, m and n have the same meaning as described above.

The reaction is carried out in the presence of a dehydration agent, and without a solvent or in a solvent.

Examples of the solvents used for the reaction include ketones such as acetone, methyl ethyl ketone and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformamide, N,N-diethylacetamide and so on; nitrites such as acetonitrile and so on; dimethylsulfoxide; and the mixture thereof.

Examples of the dehydration agents used for the reaction include acid anhydrides such as acetic anhydride and so on.

The amount of the dehydration agent to be used in the reaction is usually 1 mole to excess amount based on one mole of the compound shown by the formula (e). In case of excess amount of dehydration agent based on the compound shown by the formula (e), a solvent may be needless.

The reaction temperature is usually in the range of −78 to 150° C., and the reaction period is usually in the range of 0.1 to 24 hours.

After the reaction, the compound shown by the formula (d) can be isolated, for example, by subjecting the reaction mixture to ordinary post-treatment, such as the reaction mixture is poured into water, extracted with an organic solvent, the organic layer is dried and concentrated and the like. The isolated compound shown by the formula (d) can be purified by a technique such as chromatography, recrystallization and the like.

Production Method 3

A production method of the compound of the present invention, wherein $R^3$ is a group of the formula $CHR^9OH$ wherein $R^9$ is a hydrogen atom or a C1 to C4 alkyl group.

The compound of the present invention, which is shown by the formula (f):

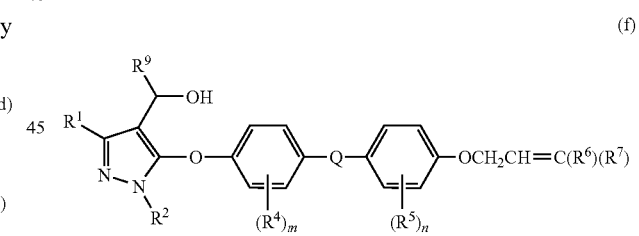

(f)

wherein $R^1$, $R^2$, $R^4$, $R^5$, $R^6$, $R^7$, $R^9$, Q, m and n have the same meaning as described above;

can be produced by reduction reaction of the compound shown by the formula (g):

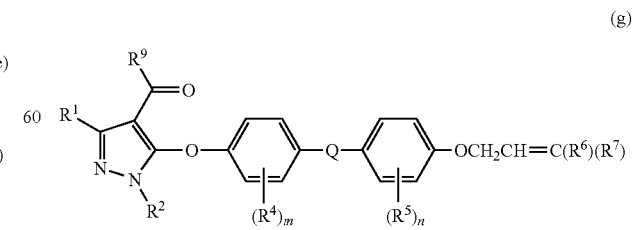

(g)

wherein $R^1$, $R^2$, $R^4$, $R^5$, $R^6$, $R^7$, $R^9$, Q, m and n have the same meaning as described above.

The reaction is carried out in the presence of a reductant usually in a solvent.

Examples of the reductants used for the reaction include sodium borohydride and so on.

Examples of the solvents used for the reaction include organic solvents selected from alcohols such as methanol, ethanol and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as dichloromethane, chloroform, 1,2-dichloroethane, chlorobenzene, dichlorobenzene and so on; the mixture thereof; and the mixture of water and an organic solvent described above.

The reaction temperature is usually in the range of −78 to 150° C., and the reaction period is usually in the range of 0.1 to 24 hours.

The amount of the reductant to be used in the reaction is, although it is various depend on the reductant to be used, usually 0.25 to 3 moles based on one mole of the compound shown by the formula (g).

After the reaction, the compound shown by the formula (f) can be isolated, for example, by subjecting the reaction mixture to post-treatment, such as the reaction mixture is poured into water, extracted with an organic solvent, the organic layer is dried and concentrated and the like. The isolated compound shown by the formula (f) can be purified by a technique such as chromatography, recrystallization and the like.

Production Method 4

A production method of the compound of the present invention, wherein $R^3$ is a group of the formula

$CHR^9OR^{10}$ wherein $R^9$ is the same meaning as described above, $R^{10}$ is a C1 to C5 alkyl group.

The compound of the present invention, which is shown by the formula (h):

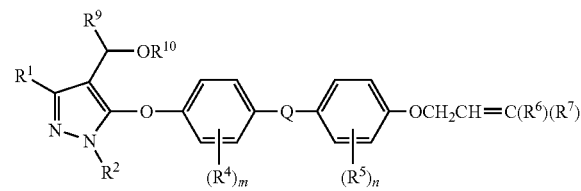

(h)

wherein $R^1$, $R^2$, $R^4$, $R^5$, $R^6$, $R^7$, $R^9$, $R^{10}$, Q, m and n have the same meaning as described above;

can be produced by the reaction of the compound shown by the formula (g) with the compound shown by the formula

$R^{10}OH$ wherein $R^{10}$ have the same meaning as described above;

in the presence of an acid and reductant.

The reaction is carried out in a solvent or without a solvent.

Examples of the solvents used for the reaction include organic solvents selected from aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as dichloromethane, chloroform, 1,2-dichloroethane, chlorobenzene, dichlorobenzene and so on; the mixture thereof; and an mixture of water and the organic solvent described above.

Examples of the reductant used for the reaction include sodium borohydride and triethylsilane.

Examples of the acid used for the reaction include inorganic acid such as hydrochloric acid, sulfuric acid and so on; organic acid such as acetic acid, trifluoroacetic acid and so on.

The amount of reagents to be used in the reaction is usually 1 mole to excess amount of the reductant and 1 mole to excess amount of the alcohol compound shown by the formula

$R^{10}OH$ based on one mole of the compound shown by the formula (g)

The reaction temperature is usually in the range of −78 to 150° C., and the reaction period is usually in the range of 0.1 to 24 hours.

After the reaction, the compound shown by the formula (h) can be isolated, for example, by subjecting the reaction mixture to post-treatment, such as the reaction mixture is poured into water, extracted with an organic solvent, the organic layer is dried and concentrated and the like. The isolated compound shown by the formula (h) can be purified by a technique such as chromatography, recrystallization and the like.

Production Method 5

A production method of the compound of the present invention, wherein $R^3$ is a group of the formula

$R^9C=C(R^{12})(R^{13})$ wherein $R^9$ is the same meaning as described above, each $R^{12}$ and $R^{13}$ is a hydrogen atom or an alkyl group.

The compound of the present invention, which is shown by the formula (k):

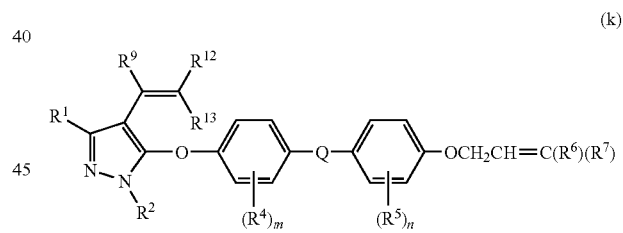

(k)

wherein $R^1$, $R^2$, $R^4$, $R^5$, $R^6$, $R^7$, $R^9$, $R^{10}$, $R^{12}$, $R^{13}$, Q, m and n have the same meaning as described above;

can be produced by the reaction of the compound shown by the formula (g) with phosphorus ylide compound shown by the formula (p)

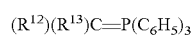
$(R^{12})(R^{13})C=P(C_6H_5)_3$ (p)

wherein $R^{12}$ and $R^{13}$ have the same meaning as described above.

The reaction is usually carried out in a solvent.

Examples of the solvents used for the reaction include ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitriles such as acetnitrile; dimethylsulfoxide and the mixture thereof.

The amount of the phosphorus ylide compound shown by the formula (p) to be used in the reaction is usually 1 to 3 moles based on one mole of the compound shown by the formula (g).

The reaction temperature is usually in the range of −78 to 150° C., and the reaction period is usually in the range of 0.1 to 24 hours.

After the reaction, the compound shown by the formula (k) can be isolated, for example, by subjecting the reaction mixture to post-treatment, such as the reaction mixture is poured into water, extracted with an organic solvent, the organic layer is dried and concentrated and the like. The isolated compound shown by the formula (k) can be purified by a technique such as chromatography, recrystallization and the like.

The phosphorus ylide compound by the formula (p) tan be produced by the reaction of the compound shown by the formula (r)

$$(R^{12})(R^{13})CHP(C_6H_5)_3Z \quad (r)$$

wherein $R^{12}$ and $R^{13}$ have the same meaning as described above, Z represents a halogen atom such as a iodine atom or a bromine atom;

with a base.

The reaction is usually carried out in a solvent.

Examples of the solvents used for the reaction include ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitriles such as acetnitrile; dimethylsulfoxide and the mixture thereof.

Example of the bases used for the reaction include hydrides of alkali metal such as sodium hydride and so on; organoalkaline metal compound such as n-butyllithium and so on.

The amount of the base to be used in the reaction is usually 1 to 3 moles based on one mole of the compound shown by the formula (r).

The reaction temperature is usually in the range of −78 to 150° C., and the reaction period is usually in the range of 0.1 to 24 hours.

The produced phosphorus ylide compound can be used to the reaction of Production Method 5 without isolation and purification.

Production Method 6

A production method of the compound of the present invention, wherein $R^3$ is a group of the formula

C≡CR⁹ wherein $R^9$ is the same meaning as described above.

The compound of the present invention, which is shown by the formula (q):

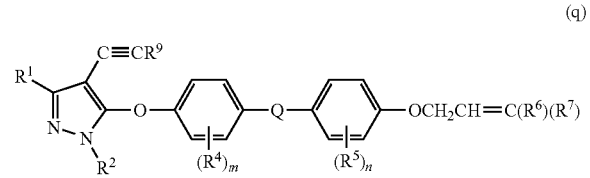

wherein $R^1$, $R^2$, $R^4$, $R^5$, $R^6$, $R^7$, $R^9$, Q, m and n have the same meaning as described above;

can be produced by the reaction of the compound shown by the formula (g) with lithium salt of trimethylsilyldiazomethane.

The reaction is usually carried out in a solvent.

Examples of the solvents used for the reaction include aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; and the mixture thereof.

The amount of the lithium salt of trimethylsilyldiazomethane to be used in the reaction is usually 1 to 3 moles based on one mole of the compound shown by the formula (g).

The reaction temperature is usually in the range of −78 to 150° C., and the reaction period is usually in the range of 0.1 to 24 hours.

After the reaction, the compound shown by the formula (q) can be isolated, for example, by subjecting the reaction mixture to post-treatment, such as the reaction mixture is poured into water, extracted with an organic solvent, the organic layer is dried and concentrated and the like. The isolated compound shown by the formula (q) can be purified by a technique such as chromatography, recrystallization and the like.

Production Method 7

A production method of the compound of the present invention, wherein $R^3$ is a group of the formula

CF₂R⁹ wherein $R^9$ is the same meaning as described above.

The compound of the present invention, which is shown by the formula (Z):

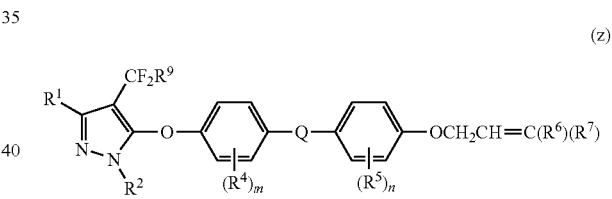

wherein $R^1$, $R^2R^4$, $R^5$, $R^6$, $R^7$, $R^9$, Q, m and n have the same meaning as described above;

can be produced by the reaction of the compound shown by the formula (g) with fluorination reagent agent such as (dimethylamino)sulfur trifluoride.

The reaction is usually carried out in a solvent.

Examples of the solvents used for the reaction include aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as dichloromethane, chloroform, 1,2-dichloroethane, chlorobenzene, dichlorobenzene and so on; nitriles such as acetonitrile and so on; and the mixture thereof.

The amount of the fluorinating reagent to be used in the reaction is usually 1 to 3 moles based on one mole of the compound shown by the formula (g).

The reaction temperature is usually in the range of −78 to 150° C., and the reaction period is usually in the range of 0.1 to 24 hours.

After the reaction, the compound shown by the formula (z) can be isolated, for example, by subjecting the reaction mixture to post-treatment, such as the reaction mixture is poured into water, extracted with an organic solvent, the organic layer is dried and concentrated and the like. The isolated compound shown by the formula (z) can be purified by a technique such as chromatography, recrystallization and the like.

Production Method 8

A production method of the compound of the present invention, wherein $R^3$ is a group of the formula $COOCH_2CH=C(R^6)(R^7)$ wherein $R^6$ and $R^7$ is the same meaning as described above.

The compound of the present invention, which is shown by the formula (aa):

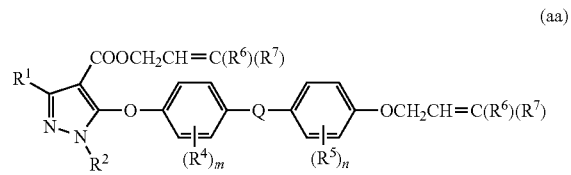

(aa)

wherein $R^1$, $R^2$, $R^4$, $R^5$, $R^6$, $R^7$, m and n have the same meaning as described above, can be produced by the reaction of the compound shown by the formula (ab)

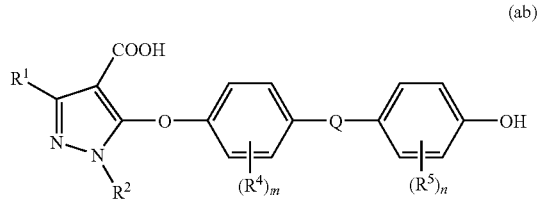

(ab)

wherein $R^1$, $R^2$, $R^4$, $R^5$, m and n have the same meaning as described above;

with a compound shown by the formula (c) in the presence of a base.

The reaction is carried out in the presence of a base usually in a solvent.

Examples of the solvents used for the reaction include ketones such as acetone, methyl ethyl ketone and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformamide, N,N-diethylacetamide and so on; nitrites such as acetonitrile and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), carbonates of alkali metal or alkaline earth metal (sodium carbonate, potassium carbonate and so on); and organic bases such as triethylamine and so on.

The amount of the reagents to be used in the reaction is usually 2 to 4 moles of the compound shown by the formula (c) and 2 to 5 moles of the base based on one mole of the compound shown by the formula (ab). The reaction temperature is usually in the range of −78 to 150° C., and the reaction period is usually in the range of 0.1 to 24 hours.

After the reaction, the compound shown by the formula (aa) can be isolated, for example, by subjecting the reaction mixture to post-treatment, such as the reaction mixture is poured into water, extracted with an organic solvent, the organic layer is dried and concentrated and the like.

The isolated compound shown by the formula (aa) can be purified by a technique such as chromatography, recrystallization and the like.

Next, the intermediate compound of the present invention are described following.

The intermediate compound of the present invention shown by the formula (b) can be produced, for example, by the reaction of the compound shown by the formula (s):

(s)

wherein $R^1$, $R^2$ and $R^8$ have the same meaning as described above; with the compound shown by the formula (t):

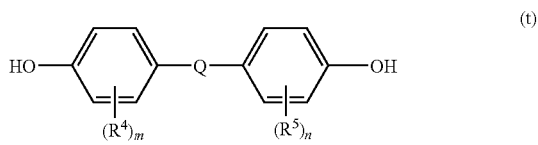

(t)

wherein $R^4$, $R^5$, Q, m and n have the same meaning as described above.

The reaction is carried out in the presence of a base usually in a solvent.

Examples of the solvents used for the reaction include aromatic hydrocarbons such as toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), hydrides of alkali metal or alkaline earth metal (sodium hydride, potassium hydride, calcium hydride and so on), carbonates of alkali metal or alkaline earth metal (sodium carbonate, potassium carbonate and so on); and organic bases such as triethylamine and so on.

The amount of the reagents to be used in the reaction is usually 0.5 to 3 moles of the compound shown by the formula (t) and 1 to 3 moles of the base based on one mole of the compound shown by the formula (s). The reaction temperature is usually in the range of −78 to 150° C., and the reaction period is usually in the range of 0.1 to 24 hours.

The reaction may be carried out in the presence of a catalyst such as copper or copper(I) chloride, if necessary. The amount of the catalyst to be used in the reaction is 0.01 to 0.2 moles based on one mole of the compound shown by the formula (s).

After the reaction, the intermediate compound of the present invention shown by the formula (b) can be isolated, for example, by subjecting the reaction mixture to post-treatment, such as the reaction mixture is poured into water, extracted with an organic solvent, the organic layer is dried and concentrated and the like. The isolated intermediate compound of the present invention shown by the formula (b) can be purified by a technique such as chromatography, recrystallization and the like.

In case of the compound shown by the formula (t) is unsymmetrical, the intermediate compound of the present invention shown by the formula (b) can be produced by protecting one of the two phenolic hydroxy group in the compound shown by the formula (t) with an appropriate protecting group (such as benzyl, tert-butyldimethylsilyl and methoxymethyl), subjecting with the reaction described above, and removing the protecting group.

The intermediate compound of the present invention, which is shown by the formula (b-1):

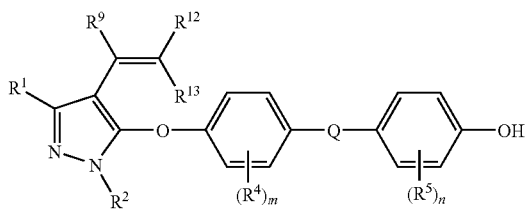

(b-1)

wherein $R^1$, $R^2$, $R^4$, $R^5$, $R^9$, $R^{12}$, $R^{13}$, Q, m and n have the same meaning as described above;

can be produced by the reaction of the compound shown by the formula (u)

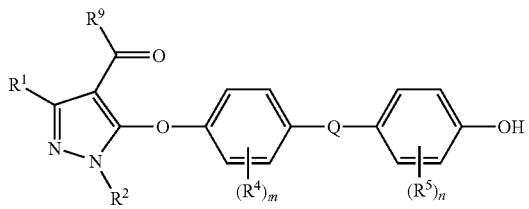

(u)

wherein $R^1$, $R^2$, $R^4$, $R^5$, $R^9$, Q, m and n have the same meaning as described above;

with phosphorus ylide compound shown by the formula (p).

The reaction is usually carried out in a solvent.

Examples of the solvents used for the reaction include ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitriles such as acetnitrile; dimethylsulfoxide and the mixture thereof.

The amount of the phosphorus ylide compound shown by the formula (p) to be used in the reaction is usually 2 to 4 moles based on one mole of the compound shown by the formula (u).

The reaction temperature is usually in the range of −78 to 150° C., and the reaction period is usually in the range of 0.1 to 24 hours.

After the reaction, the compound shown by the formula (b-1) can be isolated, for example, by subjecting the reaction mixture to post-treatment, such as the reaction mixture is poured into water, extracted with an organic solvent, the organic layer is dried and concentrated and the like. The isolated compound shown by the formula (b-1) can be purified by a technique such as chromatography, recrystallization and the like.

The intermediate compound of the present invention, which is shown by the formula (b-2):

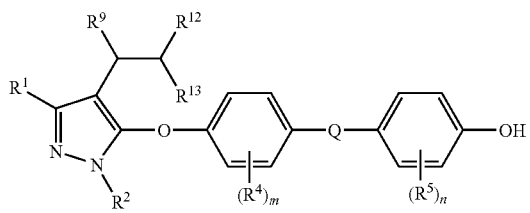

(b-2)

wherein $R^1$, $R^2$ $R^4$, $R^5$, $R^9$, $R^{12}$, $R^{13}$, Q, m and n have the same meaning as described above;

can be produced by the catalytic hydrogenation of the compound shown by the formula (b-1) in the presence of transition metal catalyst such as palladium-carbon.

The reaction is usually carried out in a solvent.

Examples of the solvents used for the reaction include ketones such as acetone, methyl ethyl ketone, and so on; alcohols such as methanol, ethanol and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitrites such as acetnitrile; dimethylsulfoxide and the mixture thereof.

The amount of the transition metal catalyst to be used in the reaction is usually 0.01 to 0.2 moles based on one mole of the compound shown by the formula (b-1).

The reaction temperature is usually in the range of −78 to 150° C., and the reaction period is usually in the range of 0.1 to 24 hours.

After the reaction, the compound shown by the formula (b-2) can be isolated, for example, by subjecting the reaction mixture to post-treatment, such as the reaction mixture is filtered, filtrate is dried and concentrated and the like. The isolated compound shown by the formula (b-2) can be purified by a technique such as chromatography, recrystallization and the like.

The intermediate compound of the present invention, which is shown by the formula (b-3):

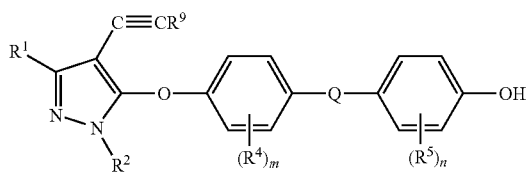

(b-3)

wherein $R^1$, $R^2$, $R^4$, $R^5$, $R^9$, Q, m and n have the same meaning as described above;

can be produced by the reaction of the compound shown by the formula (u) with lithium salt of lithium salt of trimethylsilyldiazomethane.

The reaction is usually carried out in a solvent.

Examples of the solvents used for the reaction include aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; and the mixture thereof.

The amount of the lithium salt of trimethylsilyldiazomethane to be used in the reaction is usually 2 to 4 moles based on one mole of the compound shown by the formula (u).

The reaction temperature is usually in the range of −78 to 150° C., and the reaction period is usually in the range of 0.1 to 24 hours.

After the reaction, the compound shown by the formula (b-3) can be isolated, for example, by subjecting the reaction mixture to post-treatment, such as the reaction mixture is poured into water, extracted with an organic solvent, the organic layer is dried and concentrated and the like. The isolated compound shown by the formula (b-3) can be purified by a technique such as chromatography, recrystallization and the like.

The intermediate compound of the present invention, which is shown by the formula (b-4):

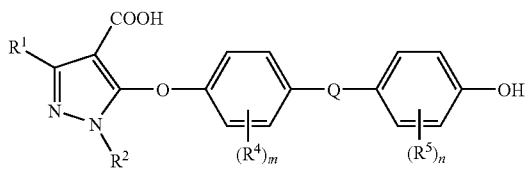

(b-4)

wherein $R^1$, $R^2$, $R^4$, $R^5$, Q, m and n have the same meaning as described above;

can be produced by the hydrolysis reaction of the compound shown by the formula (w)

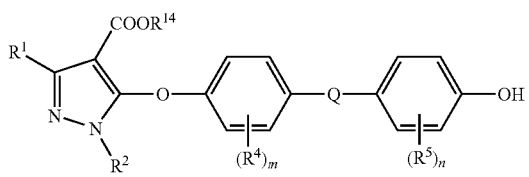

(w)

wherein $R^1$, $R^2$, $R^4$, $R^5$, Q, m and n have the same meaning as described above, $R^{14}$ represents a protective group of carboxyl group such as a methyl group or an ethyl group;

in the presence of a base.

The reaction is carried out in the presence water and usually in a solvent.

Examples of the solvents used for the reaction include ketones such as acetone, methyl ethyl ketone, and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitriles such as acetnitrile; dimethylsulfoxide and the mixture thereof.

Examples of the bases used for the reaction include inorganic bases such as hydroxides of alkali metal or alkaline earth metal (sodium hydroxide, potassium hydroxide, calcium hydroxide and so on), carbonates of alkali metal or alkaline earth metal (for example sodium carbonate, potassium carbonate and so on); and organic bases such as triethylamine and so on.

The amount of the base to be used in the reaction is usually 1 to 3 moles based on one mole of the compound shown by the formula (w).

The reaction temperature is usually in the range of −78 to 150° C., and the reaction period is usually in the range of 0.1 to 24 hours.

After the reaction, the compound shown by the formula (b-4) can be isolated, for example, by subjecting the reaction mixture to post-treatment, such as the reaction mixture is poured into water, acidified by adding an acid (for example hydrochloric acid, sulfuric acid and so on), extracted with an organic solvent, the organic layer is dried and concentrated and the like. The isolated compound shown by the formula (b-4) can be purified by a technique such as chromatography, recrystallization and the like.

The intermediate compound of the present invention, which is shown by the formula (b-5):

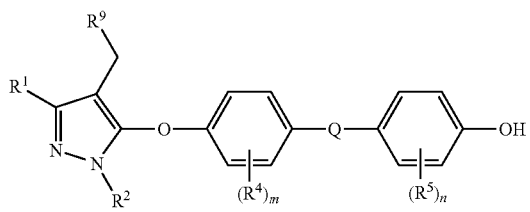

(b-5)

wherein $R^1$, $R^2$, $R^4$, $R^5$, $R^9$, Q, m and n have the same meaning as described above;

can be produced by reduction reaction of the compound shown by the formula (u) with hydrazine in the presence of a base.

The reaction is usually carried out in a solvent.

Examples of the solvents used for the reaction include aromatic hydrocarbons such as benzene, toluene, xylene and so on; aliphatic hydrocarbons such as hexane, heptane and so on; alcohols such as methanol, ethanol, ethylene glycol, diethylene glycol and so on, ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitriles such as acetnitrile; dimethylsulfoxide and the mixture thereof.

Examples of the bases used for the reaction include inorganic bases such as hydroxides of alkali metal or alkaline earth metal (sodium hydroxide, potassium hydroxide, calcium hydroxide and so on), alkoxides of alkali metal such as sodium ethoxide; hydrides of alkali metal or alkaline earth metal (sodium hydride, potassium hydride, calcium hydride and so on), carbonates of alkali metal or alkaline earth metal (sodium carbonate, potassium carbonate and so on); and organic bases such as triethylamine and so on.

The amount of the reagents to be used in the reaction is usually 2 to 4 moles of the base and 1 to 3 moles of hydrazine based on one mole of the compound shown by the formula (u).

The reaction temperature is usually in the range of 0 to 250° C., and the reaction period is usually in the range of 0.1 to 24 hours.

After the reaction, the compound shown by the formula (b-5) can be isolated, for example, by subjecting the reaction mixture to post-treatment, such as the reaction mixture is poured into water, extracted with an organic solvent, the organic layer is dried and concentrated and the like. The isolated compound shown by the formula (b-5) can be purified by a technique such as chromatography, recrystallization and the like.

The intermediate compound of the present invention, which is shown by the formula (b-6):

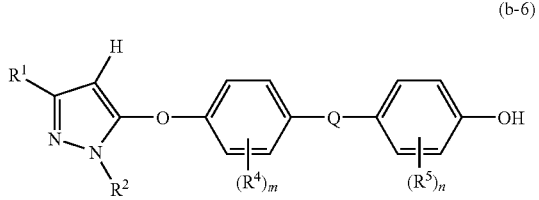

(b-6)

wherein $R^1$, $R^2$, $R^4$, $R^5$, m and n have the same meaning as described above;

can be produced by decarboxylate reaction of the compound shown by the formula (b-4).

The reaction is carried out without a solvent or in a solvent, and in the presence of an acid or a base, if necessary.

Examples of the solvents used for the reaction include organic solvents selected from ketones such as acetone, methyl ethyl ketone, and so on; aromatic hydrocarbons such as benzene, toluene, xylene and so on; aliphatic hydrocarbons such as hexane, heptane and so on; alcohols such as methanol, ethanol and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitriles such as acetnitrile; dimethylsulfoxide; acid anhydride such as acetic anhydride; the mixture thereof; and the mixture of water and an organic solvent described above.

Examples of the acids used for the reaction include inorganic acids such as hydrochloric acid, sulfuric acid and so on.

Examples of the bases used for the reaction include inorganic bases such as hydroxides of alkali metal or alkaline earth metal (sodium hydroxide, potassium hydroxide, calcium hydroxide and so on), carbonates of alkali metal or alkaline earth metal (sodium carbonate, potassium carbonate and so on); and organic bases such as triethylamine, quinoline and so on.

The amount of the reagents to be used in the reaction is usually 1 mole to excess amount of the acid or 1 mole to excess amount of the base based on one mole of the compound shown by the formula (b-4).

The reaction temperature is usually in the range of 0 to 250° C., and the reaction period is usually in the range of 0.1 to 24 hours.

The reaction may be carried out in the presence of a catalyst such as copper or copper(I) chloride, if necessary.

The amount of catalyst to be used in the reaction is 0.01 to 0.1 moles based on one mole of the compound shown by the formula (b-4).

After the reaction, the compound shown by the formula (b-6) can be isolated, for example, by subjecting the reaction mixture to post-treatment, such as the reaction mixture is poured into water, acidified by adding an acid (for example hydrochloric acid, sulfuric acid and so on), extracted with an organic solvent, the organic layer is dried and concentrated and the like. The isolated compound shown by the formula (b-6) can be purified by a technique such as chromatography, recrystallization and the like.

The intermediate compound of the present invention, which is shown by the formula (b-7):

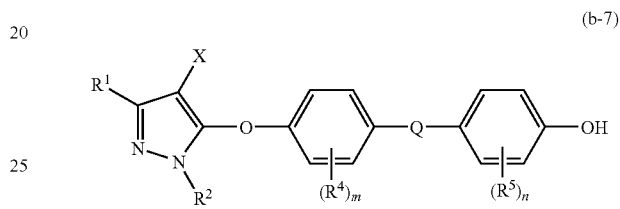

(b-7)

wherein $R^1$, $R^2$, $R^4$, $R^5$, m and n have the same meaning as described above, X represents a halogen atom such as chlorine atom, bromine atom and iodine atom;

can be produced by the reaction of the compound shown by the formula (b-6) with the N-halo succinimide compound shown by the formula (y):

(y)

wherein X have the same meaning as described above.

The reaction is usually carried out in a solvent.

Examples of the solvents used for the reaction include aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformaide, N,N-dimethylacetamide; nitriles such as acetnitrile; dimethylsulfoxide; and the mixture thereof.

The amount of the N-halo succinimide compound to be used in the reaction is usually 1 to 3 moles based on one mole of the compound shown by the formula (b-6).

The reaction temperature is usually in the range of −78 to 150° C., and the reaction period is usually in the range of 0.1 to 24 hours.

After the reaction, the compound shown by the formula (b-7) can be isolated, for example, by subjecting the reaction mixture to post-treatment, such as the reaction mixture is poured into water, extracted with an organic solvent, the organic layer is dried and concentrated and the like. The isolated compound shown by the formula (b-7) can be purified by a technique such as chromatography, recrystallization and the like.

The compound shown by the formula (e) can be produced by the reaction of the compound shown by the formula (g) in which $R^9$ is a hydrogen atom with hydroxylamine or its salt (for example hydrocloric acid salt).

The reaction is carried out in the presence of a base usually in a solvent. The reaction temperature is usually in the range of −78 to 150° C., and the reaction period is in the range of 0.1 to 24 hours.

Examples of the solvents used for the reaction include alcohols such as methanol, ethanol and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; chlorinated hydrocarbons such as dichloromethane, chloroform, 1,2-dichloroethane, chlorobenzene, dichlorobenzene and so on; amides such as N,N-dimethylformamide, N,N-diethylacetamide and so on; nitrites such as acetonitrile and so on; dimethylsulfoxide; water and the mixture thereof.

Examples of the bases used for the reaction include inorganic bases such as hydrides of alkali metal or alkaline earth metal (sodium hydride, potassium hydride, calcium hydride and so on), sodium carbonate, potassium carbonate and so on; and organic bases such as triethylamine, pyridine and so on.

Based on one mole of the compound shown by the formula (g), 1 to 3 moles of the hydroxylamine or the salt thereof and 1 to 3 moles of the base are used.

After the reaction, the compound shown by the formula (e) can be isolated, for example, by subjecting the reaction mixture to post-treatment, such as the reaction mixture is poured into water, extracted with an organic solvent, the organic layer is dried and concentrated and the like. The isolated compound shown by the formula (e) can be purified by a technique such as chromatography, recrystallization and the like.

The compound shown by the formula (g) can be produced by the reaction of the compound shown by the formula (u) with the compound shown by the formula (c).

The reaction is carried out in the presence of a base usually in a solvent.

Examples of the solvents used for the reaction include ketones such as acetone, methyl ethyl ketone and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformamide, N,N-diethylacetamide and so on; nitrites such as acetonitrile and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), carbonates of alkali metal or alkaline earth metal (sodium carbonate, potassium carbonate and so on); and organic bases such as triethylamine and so on.

The amount of the reagents to be used in the reaction is usually 1 to 3 moles of the compound shown by the formula (c) and 1 to 3 moles of the base based on one mole of the compound shown by the formula (u). The reaction temperature is usually in the range of −78 to 150° C., and the reaction period is usually in the range of 0.1 to 24 hours.

After the reaction, the compound shown by the formula (g) can be isolated, for example, by subjecting the reaction mixture to post-treatment, such as the reaction mixture is poured into water, extracted with an organic solvent, the organic layer is dried and concentrated and the like. The isolated compound shown by the formula (g) can be purified by a technique such as chromatography, recrystallization and the like.

The compound shown by the formula (u) can be produced by the reaction of the compound shown by the formula (ad):

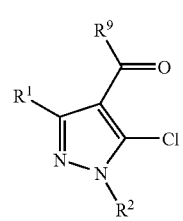

(ad)

wherein $R^1$, $R^2$ and $R^9$ have the same meaning as described above; with the compound shown by the formula (t).

The reaction is carried out in the presence of a base usually in a solvent.

Examples of the solvents used for the reaction include aromatic hydrocarbons such as toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), hydrides of alkali metal or alkaline earth metal (sodium hydride, potassium hydride, calcium hydride and so on), carbonates of alkali metal or alkaline earth metal (sodium carbonate, potassium carbonate and so on); and organic bases such as triethylamine and so on.

The amount of the reagents to be used in the reaction is usually 0.5 to 3 moles of the compound shown by the formula (t) and 1 to 3 moles of the base based on one mole of the compound shown by the formula (ad).

The reaction temperature is usually in the range of −78 to 150° C., and the reaction period is usually in the range of 0.1 to 24 hours.

The reaction may be carried out in the presence of a catalyst such as copper or copper(I) chloride, if necessary.

The amount of the catalyst to be used in the reaction is 0.01 to 0.2 moles based on one mole of the compound shown by the formula (ad).

After the reaction, the compound shown by the formula (u) can be isolated, for example, by subjecting the reaction mixture to post-treatment, such as the reaction mixture is poured into water, extracted with an organic solvent, the organic layer is dried and concentrated and the like. The isolated compound shown by the formula (u) can be purified by a technique such as chromatography, recrystallization and the like.

In case of the compound shown by the formula (t) is unsymmetrical, the compound shown by the formula (u) can be produced by protecting one of the two phenolic hydroxy group in the compound shown by the formula (t) with an appropriate protecting group (such as benzyl, tert-butyldimethylsilyl and methoxymethyl), subjecting with the reaction described above, and removing the protecting group.

The compound shown by the formula (w) can be produced by the reaction of the compound shown by the formula (ae):

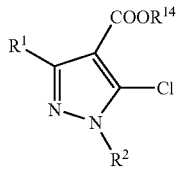
(ae)

wherein $R^1$, $R^2$ and $R^{14}$ have the same meaning as described above;

with the compound shown by the formula (t).

The reaction is carried out in the presence of a base usually in a solvent.

Examples of the solvents used for the reaction include aromatic hydrocarbons such as toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), hydrides of alkali metal or alkaline earth metal (sodium hydride, potassium hydride, calcium hydride and so on), carbonates of alkali metal or alkaline earth metal (sodium carbonate, potassium carbonate and so on); and organic bases such as triethylamine and so on.

The amount of the reagents to be used in the reaction is usually 0.5 to 3 moles of the compound shown by the formula (t) and 1 to 3 moles of the base based on one mole of the compound shown by the formula (ae). The reaction temperature is usually in the range of −78 to 150° C., and the reaction period is usually in the range of 0.1 to 24 hours.

The reaction may be carried out in the presence of a catalyst such as copper or copper(I) chloride, if necessary. The amount of the catalyst to be used in the reaction is 0.01 to 0.2 moles based on one mole of the compound shown by the formula (ae).

After the reaction, the compound shown by the formula (w) can be isolated, for example, by subjecting the reaction mixture to post-treatment, such as the reaction mixture is poured into water, extracted with an organic solvent, the organic layer is dried and concentrated and the like. The isolated compound shown by the formula (w) can be purified by a technique such as chromatography, recrystallization and the like.

In case of the compound shown by the formula (t) is unsymmetrical, the compound shown by the formula (w) can be produced by protecting one of the two phenolic hydroxy group in the compound shown by the formula (t) with an appropriate protecting group (such as benzyl, tert-butyldimethylsilyl and methoxymethyl), subjecting with the reaction described above, and removing the protecting group.

The compound shown by the formula (t-1), which Q is an oxygen atom in the compound shown by the formula (t):

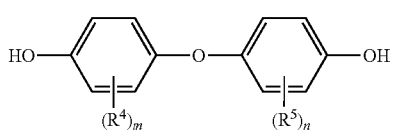
(t-1)

wherein $R^4$, $R^5$, m and n have the same meaning as described above;

can be produced, for example, by deprotection of the protecting group of the compound shown by the formula (tt-1):

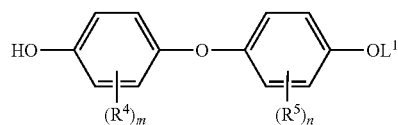
(tt-1)

wherein $R^4$, $R^5$, m and n have the same meaning as described above, $L^1$ represents a protective group (benzyl group, tert-buthyldimethylsilyl group, methyoxymethyl group, and the like).

The condition of depretection of the protecting group of the compound shown by the formula (tt-1) can be adopted known depretection condition for each protecting group.

The compound shown by the formula (tt-1) can be produced, for example, by the reaction of the compound shown by the formula (s-1):

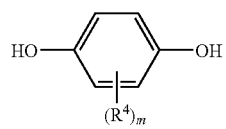
(s-1)

wherein $R^4$ and m have the same meaning as described above;

and the compound shown by the formula (s-2):

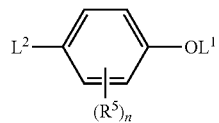
(s-2)

wherein $R^5$, n and $L^1$ have the same meaning as described above, $L^2$ represents a halogen atom (chlorine atom, bromine atom, iodine atom, and the like).

The reaction is carried out in the presence of a base usually in a solvent.

Examples of the solvents used for the reaction include ketones such as acetone, methylethylketone and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), carbonates of alkali metal or alkaline earth metal (sodium carbonate, potassium carbonate, cesium carbonete and so on); and organic bases such as triethylamine and so on.

The amount of the reagents to be used in the reaction is usually 1 to 3 moles of the compound shown by formula (s-2) and 1 to 3 moles of the base based on one mole of the compound of the formula (s-1). The reaction temperature is usually in the range of −78 to 150° C., and the reaction period is usually in the range of 0.1 to 24 hours.

The reaction may be carried out in the presence of a catalyst such as copper, copper (I) chloride and so on, if necessary.

The amount of the catalyst to be used in the reaction is 0.01 to 0.2 moles based on one mole of the compound shown by the formula (s-1).

After the reaction, the compound shown by the formula (tt-1) can be isolated, for example, by subjecting the reaction mixture to post-treatment, such as the reaction mixture is poured into water, extracted with an organic solvent, the organic layer is dried and concentrated and the like. The isolated compound shown by the formula (tt-1) can be purified by a technique such as chromatography, recrystallization and the like.

The compound shown by the formula (tt-1) can also be produced by the reaction of the compound shown by the formula (s-1) and the compound shown by the formula (s-4):

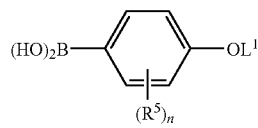

(s-4)

wherein $R^5$, n and $L^1$ have the same meaning as described above.

The reaction is carried out in the presence of copper acetate and a organic base, usually in a solvent.

Examples of the solvents used for the reaction include halogenated hydrocarbons such as dichloromethane, chloroform, 1,2-dichloroethane and so on.

Examples of the organic bases used for the reaction include pyridine derivatives such as pyridine and so on, tertiary amines such as triethylamine and so on.

The amount of the reagents to be used in the reaction is usually 1 to 3 moles of the compound of formula (s-4), 1 to 3 moles s of copper acetate and 1 mole to excess amount of the organic base based on one mole of the compound shown by the formula (s-1)

The reaction temperature is usually in the range of −78 to 150° C., and the reaction period is usually in the range of 0.1 to 24 hours.

The reaction may be carried out in the presence of a molecular seives, if necessary.

After the reaction, the compound shown by the formula (tt-1) can be isolated, for example, by subjecting the reaction mixture to post-treatment, such as the reaction mixture is poured into water, extracted with an organic solvent, the organic layer is dried and concentrated and the like. The isolated compound shown by the formula (tt-1) can be purified by a technique such as chromatography, recrystallization and the like.

The compound shown by the formula (t-2), which Q is a sulfur atom in the compound shown by the formula (t):

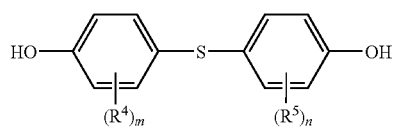

(t-2)

wherein $R^4$, $R^5$, m and n have the same meaning as described above; can be produced, for example, by the reaction of the compound shown by the formula (s-5):

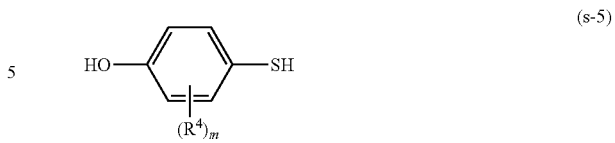

(s-5)

wherein $R^4$ and m have the same meaning as described above; and the compound shown by the formula (s-6):

(s-6)

wherein $R^5$, n and $L^2$ have the same meaning as described above.

The reaction is carried out in the presence of a base usually in a solvent.

Examples of the solvents used for the reaction include ketones such as acetone, methylethylketone and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; and the mixture thereof.

Examples of the bases used for the reaction include inorganic bases such as hydroxides of alkali metal or alkaline earth metal (sodium hydroxide, potassium hydroxide, calcium hydroxide and so on), carbonates of alkali metal or alkaline earth metal (sodium carbonate, potassium carbonate, cesium carbonete and so on) and so on.

The amount of the reagents to be used in the reaction is usually 1 to 3 moles of the compound of formula (s-6) and 1 to 3 moles of the base based on one mole of the compound shown by the formula (s-5).

The reaction temperature is usually in the range of −78 to 150° C., and the reaction period is usually in the range of 0.1 to 24 hours.

The reaction may be carried out in the presence of a catalyst such as copper, copper (I) chloride and so on, if necessary.

The amount of the catalyst to be used in the reaction is 0.01 to 0.2 moles based on one mole of the compound shown by the formula (s-5).

After the reaction, the compound shown by the formula (t-2) can be isolated, for example, by subjecting the reaction mixture to post-treatment, such as the reaction mixture is poured into water, extracted with an organic solvent, the organic layer is dried and concentrated and the like. The isolated compound shown by the formula (t-2) can be purified by a technique such as chromatography, recrystallization and the like.

The compound shown by the formula (t-2) can also be produced by deprotection of the protective group of the compound shown by the formula (tt-2):

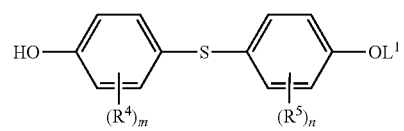

(tt-2)

wherein $R^4$, $R^5$, m, n and $L^1$ have the same meaning as described above.

The condition of depretection of the protecting group of the compound shown by the formula (tt-2) can be adopted known depretection condition for the each protecting group.

The condition of deprorection of the protecting group of the compound shown by the formula (tt-2) can be adopted known deprotection condition for each compound.

The compound shown by the formula. (tt-2) can be produced, for example, by the reaction of the compound shown by the formula (s-7):

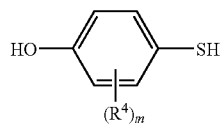

(s-7)

wherein $R^4$ and m have the same meaning as described above;

and the compound shown by the formula (s-2).

The reaction is carried out in the presence of a base usually in a solvent.

Examples of the solvents used for the reaction include ketones such as acetone, methylethylketone and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; dimethylsulfoxide; and the mixture thereof.

Examples of the bases used for the reaction include inorganic bases such as hydroxides of alkali metal or alkaline earth metal (sodium hydroxide, potassium hydroxide, calcium hydroxide and so on), carbonates of alkali metal or alkaline earth metal (sodium carbonate, potassium carbonate, cesium carbonete and so on); and organic bases such as triethylamine and so on.

The amount of the reagents to be used in the reaction is usually 1 to 3 moles of the compound shown by the formula (s-2) and 1 to 3 moles of the base based on one mole of the compound shown by the formula (s-7). The reaction temperature is usually in the range of −78 to 150° C., and the reaction period is usually in the range of 0.1 to 24 hours.

The reaction may be carried out in the presence of a catalyst such as copper, copper (I) chloride and so on, if necessary.

The amount of the catalyst to be used in the reaction is 0.01 to 0.2 moles based on one mole of the compound shown by the formula (s-7).

After the reaction, the compound shown by the formula (tt-2) can be isolated, for example, by subjecting the reaction mixture to post-treatment, such as the reaction mixture is poured into water, extracted with an organic solvent, the organic layer is dried and concentrated and the like. The isolated compound shown by the formula (tt-2) can be purified by a technique such as chromatography, recrystallization and the like.

The compound shown by the formula (t-3), which Q is a C1-C5 alkylidene group in the compound shown by the formula (t):

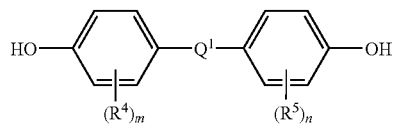

(t-3)

wherein $R^4$, $R^5$, m and n have the same meaning as described above, $Q^1$ represents a C1-C5 alkylidene group;

can be produced, for example, by the reaction of the compound shown by the formula (s-9):

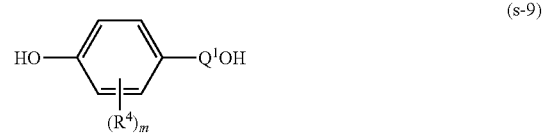

(s-9)

wherein $R^4$, m and $Q^2$ have the same meaning as described above;

and the compound shown by the formula (s-10):

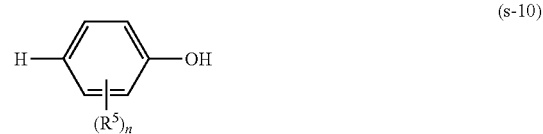

(s-10)

wherein $R^5$ and n have the same meaning as described above.

The reaction is carried out in the presence of an acid, in a solvent or without a solvent.

Examples of the solvents used for the reaction include ethers such as diethyl ether, tetrahydrofuran, 1,4-dioxane, 1,2-dimethoxyethane, 1,2-diethoxyethane and so on; halogenated hydrocarbons such as dichlorometane, chloroform, 1,2-dichloroethane and so on; and the mixture thereof.

Examples of the acids used for the reaction include sulfric acid, phosphoric acid, aluminium chloride, boron trifluoride diethyl etherate and so on.

The amount of the reagents to be used in the reaction is usually 1 to 3 moles of the compound shown by the formula (s-10) and 1 mole to excess amount of the base based on one mole shown by the compound of the formula (s-9).

The reaction temperature is usually in the range of −7.8 to 150° C., and the reaction period is usually in the range of 0.1 to 24 hours.

After the reaction, the compound shown by the formula (t-3) can be isolated, for example, by subjecting the reaction mixture to post-treatment, such as the reaction mixture is poured into water, extracted with an organic solvent, the organic layer is dried and concentrated and the like. The isolated compound shown by the formula (t-3) can be purified by a technique such as chromatography, recrystallization and the like.

The compounds of the present invention are exemplified below.

The pyrazole compound shown by the formula (I) to (XC).

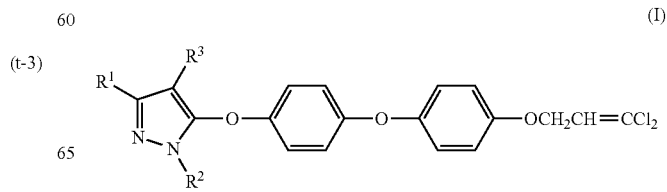

(I)

33

-continued (II) Pyrazole(R¹,R²,R³)—O—C₆H₄—O—C₆H₃(2-Cl)—OCH₂CH=CCl₂

(III) Pyrazole(R¹,R²,R³)—O—C₆H₄—O—C₆H₃(3-Cl)—OCH₂CH=CCl₂

(IV) Pyrazole(R¹,R²,R³)—O—C₆H₄—O—C₆H₂(2,6-diCl)—OCH₂CH=CCl₂

(V) Pyrazole(R¹,R²,R³)—O—C₆H₄—O—C₆H₂(3,5-diCl)—OCH₂CH=CCl₂

(VI) Pyrazole(R¹,R²,R³)—O—C₆H₃(3-Cl)—O—C₆H₄—OCH₂CH=CCl₂

(VII) Pyrazole(R¹,R²,R³)—O—C₆H₃(2-Cl)—O—C₆H₄—OCH₂CH=CCl₂

(VIII) Pyrazole(R¹,R²,R³)—O—C₆H₂(2,6-diCl)—O—C₆H₄—OCH₂CH=CCl₂

(IX) Pyrazole(R¹,R²,R³)—O—C₆H₄—O—C₆H₃(2-F)—OCH₂CH=CCl₂

34

-continued (X) Pyrazole(R¹,R²,R³)—O—C₆H₄—O—C₆H₃(2-Br)—OCH₂CH=CCl₂

(XI) Pyrazole(R¹,R²,R³)—O—C₆H₄—O—C₆H₃(2-CH₃)—OCH₂CH=CCl₂

(XII) Pyrazole(R¹,R²,R³)—O—C₆H₄—O—C₆H₃(2-CH₂CH₃)—OCH₂CH=CCl₂

(XIII) Pyrazole(R¹,R²,R³)—O—C₆H₄—O—C₆H₃(2-CH₂CH₂CH₃)—OCH₂CH=CCl₂

(XIV) Pyrazole(R¹,R²,R³)—O—C₆H₄—O—C₆H₃(2-CH(CH₃)₂)—OCH₂CH=CCl₂

(XV) Pyrazole(R¹,R²,R³)—O—C₆H₄—O—C₆H₃(2-OCH₃)—OCH₂CH=CCl₂

(XVI) Pyrazole(R¹,R²,R³)—O—C₆H₄—O—C₆H₃(2-OCH₂CH₃)—OCH₂CH=CCl₂

(XVII) Pyrazole(R¹,R²,R³)—O—C₆H₄—O—C₆H₃(2-OCH₂CH₂CH₃)—OCH₂CH=CCl₂

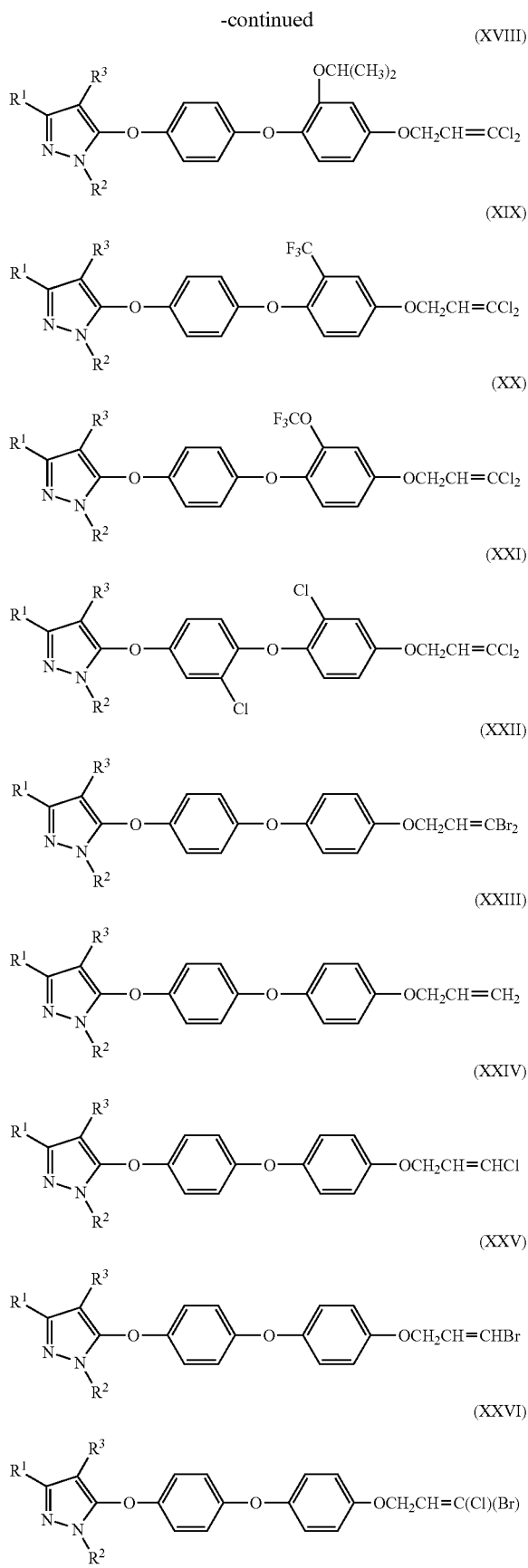
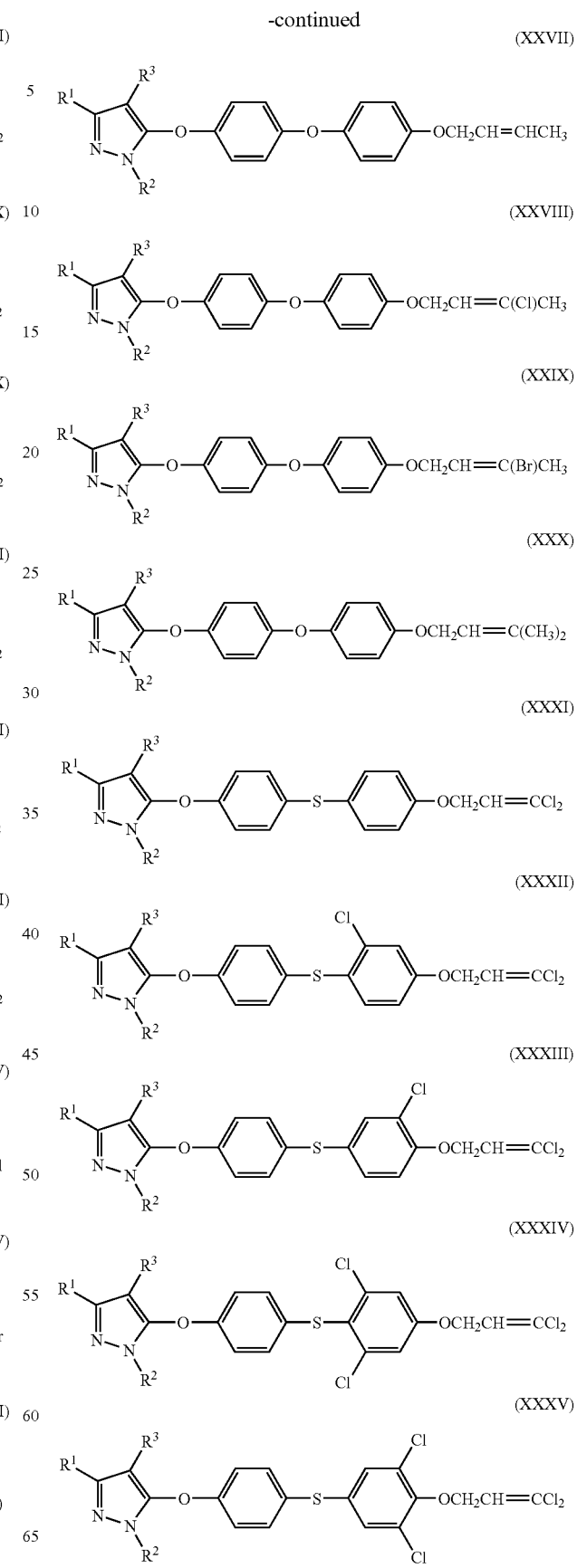

-continued (XXXVI)

(XXXVII)

(XXXVIII)

(XXXIX)

(XL)

(XLI)

(XLII)

(XLIII)

-continued (XLIV)

(XLV)

(XLVI)

(XLVII)

(XLVIII)

(XLIX)

(L)

(LI)

-continued
(LII) 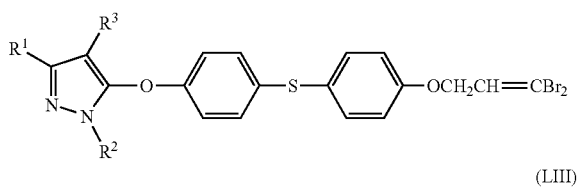
(LIII) 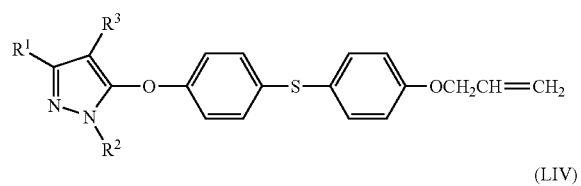
(LIV) 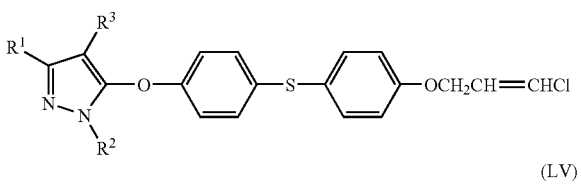
(LV) 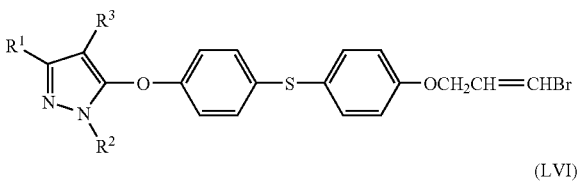
(LVI) 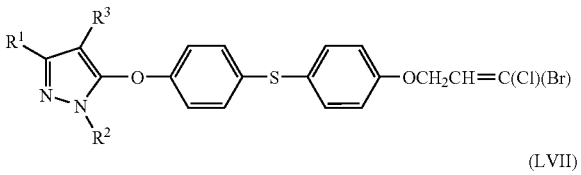
(LVII) 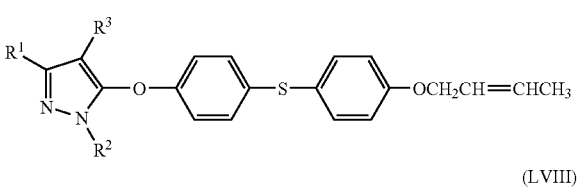
(LVIII) 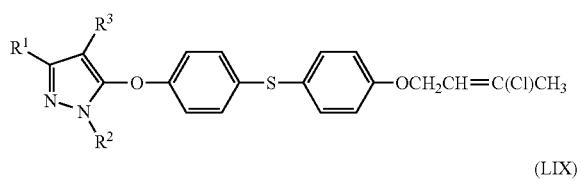
(LIX) 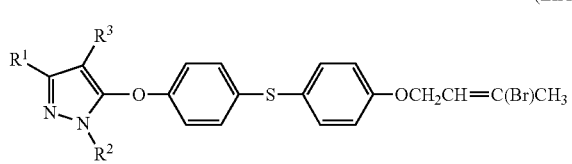
(LX) 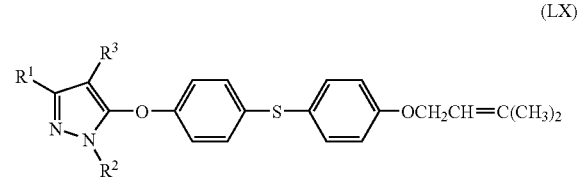
-continued
(LXI) 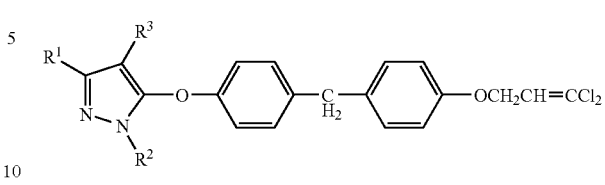
(LXII) 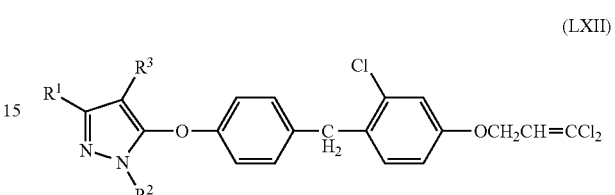
(LXIII) 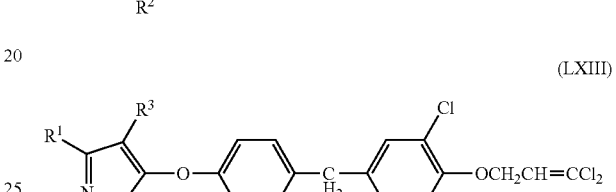
(LXIV) 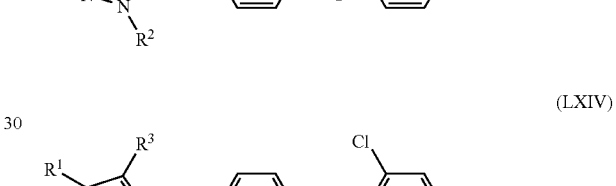
(LXV) 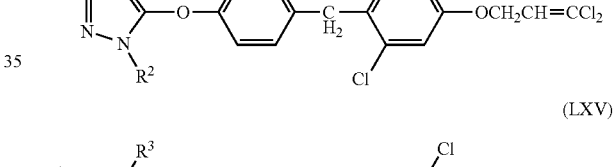
(LXVI) 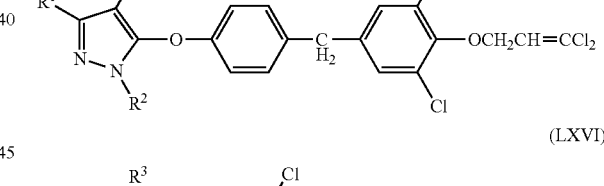
(LXVII) 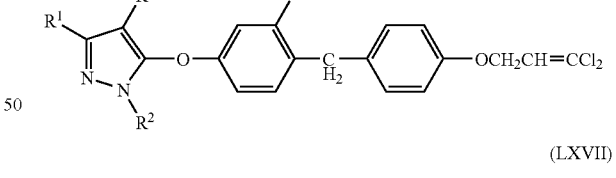
(LXVIII) 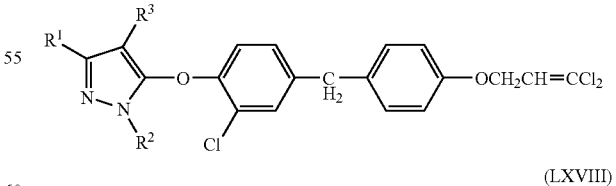
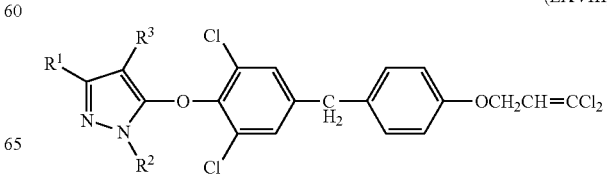

(LXIX), (LXX), (LXXI), (LXXII), (LXXIII), (LXXIV), (LXXV), (LXXVI), (LXXVII), (LXXVIII), (LXXIX), (LXXX), (LXXXI), (LXXXII), (LXXXIII), (LXXXIV)

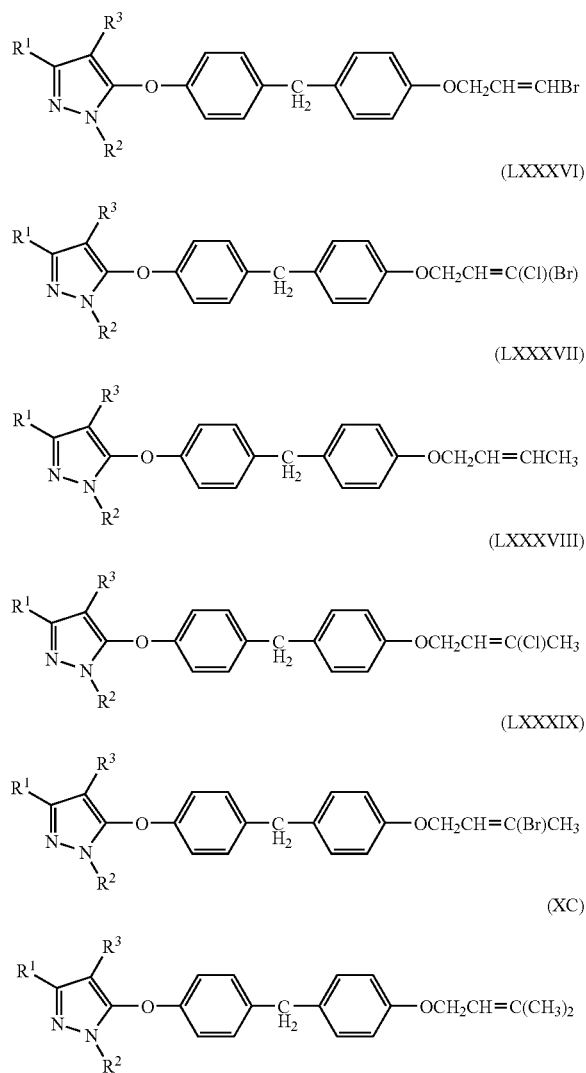

Each of $R^1$, $R^2$ and $R^3$ in the formula (I) to (XC) is any one of the combination described in Table 1 to 50.

TABLE 1

| $R^1$ | $R^2$ | $R^3$ |
|---|---|---|
| $CH_3$ | $CH_3$ | H |
| $CH_3$ | $CH_3$ | $CH_3$ |
| $CH_3$ | $CH_3$ | $CH_2CH_3$ |
| $CH_3$ | $CH_3$ | $CH_2CH_2CH_3$ |
| $CH_3$ | $CH_3$ | $CH(CH_3)_2$ |
| $CH_3$ | $CH_3$ | $CH_2CH_2CH_2CH_3$ |
| $CH_3$ | $CH_3$ | $CH(CH_3)CH_2CH_3$ |
| $CH_3$ | $CH_3$ | $CH_2CH(CH_3)_2$ |
| $CH_3$ | $CH_3$ | $CH_2CH_2CH_2CH_2CH_3$ |
| $CH_3$ | $CH_3$ | $CH_2CH_2CH(CH_3)_2$ |
| $CH_3$ | $CH_3$ | $CH(CH_3)CH_2CH_2CH_3$ |
| $CH_3$ | $CH_3$ | $CH_2CH(CH_3)CH_2CH_3$ |
| $CH_3$ | $CH_3$ | $CH(CH_3)CH(CH_3)_2$ |
| $CH_3$ | $CH_3$ | $CH_2CH_2CH_2CH_2CH_2CH_3$ |
| $CH_3$ | $CH_3$ | $CH_2F$ |
| $CH_3$ | $CH_3$ | $CF_3$ |
| $CH_3$ | $CH_3$ | $CH_2CH_2F$ |
| $CH_3$ | $CH_3$ | $CH_2CF_3$ |

TABLE 1-continued

| $R^1$ | $R^2$ | $R^3$ |
|---|---|---|
| $CH_3$ | $CH_3$ | $CH_2CH_2CH_2F$ |
| $CH_3$ | $CH_3$ | $CH_2CH_2CF_3$ |
| $CH_3$ | $CH_3$ | $CH_2CH_2CH_2CH_2F$ |
| $CH_3$ | $CH_3$ | $CH_2CH_2CH_2CF_3$ |
| $CH_3$ | $CH_3$ | $CH_2CH_2CH_2CH_2CF_3$ |
| $CH_3$ | $CH_3$ | $CH_2CH_2Cl$ |
| $CH_3$ | $CH_3$ | $CHClCH_2Cl$ |
| $CH_3$ | $CH_3$ | $CH_2CH_2Br$ |
| $CH_3$ | $CH_3$ | $CHBrCH_2Br$ |
| $CH_3$ | $CH_3$ | $CH_2CH_2CH_2Cl$ |
| $CH_3$ | $CH_3$ | $CH_2CHClCH_2Cl$ |
| $CH_3$ | $CH_3$ | $CH_2CH_2CH_2Br$ |
| $CH_3$ | $CH_3$ | $CH_2CHBrCH_2Br$ |
| $CH_3$ | $CH_3$ | $CH_2CH_2CH_2CH_2Cl$ |
| $CH_3$ | $CH_3$ | $CH_2CH_2CH_2CH_2Br$ |
| $CH_3$ | $CH_3$ | $CH_2CH_2CH_2CH_2CH_2Cl$ |
| $CH_3$ | $CH_3$ | $CH_2CH_2CH_2CH_2CH_2Br$ |

TABLE 2

| $R^1$ | $R^2$ | $R^3$ |
|---|---|---|
| $CH_3$ | $CH_3$ | $CH_2CH_2CH_2CH_2CH_2CH_2Cl$ |
| $CH_3$ | $CH_3$ | $CH_2CH_2CH_2CH_2CH_2CH_2Br$ |
| $CH_3$ | $CH_3$ | $CH=CH_2$ |
| $CH_3$ | $CH_3$ | $CH_2CH=CH_2$ |
| $CH_3$ | $CH_3$ | $CH=CHCH_3$ |
| $CH_3$ | $CH_3$ | $C(CH_3)=CH_2$ |
| $CH_3$ | $CH_3$ | $CH=CHCH_2CH_3$ |
| $CH_3$ | $CH_3$ | $CH_2CH=CHCH_3$ |
| $CH_3$ | $CH_3$ | $CH_2CH_2CH=CH_2$ |
| $CH_3$ | $CH_3$ | $C(CH_3)=CHCH_3$ |
| $CH_3$ | $CH_3$ | $CH(CH_3)CH=CH_2$ |
| $CH_3$ | $CH_3$ | $CH=C(CH_3)_2$ |
| $CH_3$ | $CH_3$ | $CH_2C(CH_3)=CH_2$ |
| $CH_3$ | $CH_3$ | $C(CH_3)_2=CH_2$ |
| $CH_3$ | $CH_3$ | $CH=CHCH_2CH_2CH_3$ |
| $CH_3$ | $CH_3$ | $C(CH_3)=CHCH_2CH_3$ |
| $CH_3$ | $CH_3$ | $CH(CH_3)CH=CHCH_3$ |
| $CH_3$ | $CH_3$ | $CH(CH_3)CH_2CH=CH_2$ |
| $CH_3$ | $CH_3$ | $CH=C(CH_3)CH_2CH_3$ |
| $CH_3$ | $CH_3$ | $CH_2C(CH_3)=CHCH_3$ |
| $CH_3$ | $CH_3$ | $CH_2CH(CH_3)CH=CH_2$ |
| $CH_3$ | $CH_3$ | $CH=CHCH(CH_3)_2$ |
| $CH_3$ | $CH_3$ | $CH_2CH=C(CH_3)_2$ |
| $CH_3$ | $CH_3$ | $CH_2CH_2C(CH_2)=CH_2$ |
| $CH_3$ | $CH_3$ | $CH_2CH=C(CH_3)_2$ |
| $CH_3$ | $CH_3$ | $CH=CHCH_2CH_2CH_2CH_3$ |
| $CH_3$ | $CH_3$ | $CH=CHCl$ |
| $CH_3$ | $CH_3$ | $CH=CCl_2$ |
| $CH_3$ | $CH_3$ | $CH=C(CH_3)Cl$ |
| $CH_3$ | $CH_3$ | $CH_2CH=CHCl$ |
| $CH_3$ | $CH_3$ | $CH_2CCl=CHCl$ |
| $CH_3$ | $CH_3$ | $CH_2CH=CCl_2$ |
| $CH_3$ | $CH_3$ | $CH=CHBr$ |
| $CH_3$ | $CH_3$ | $CH=CBr_2$ |
| $CH_3$ | $CH_3$ | $CH=C(CH_3)Br$ |

TABLE 3

| $R^1$ | $R^2$ | $R^3$ |
|---|---|---|
| $CH_3$ | $CH_3$ | $CH_2CH=CHBr$ |
| $CH_3$ | $CH_3$ | $CH_2CBr=CHBr$ |
| $CH_3$ | $CH_3$ | $CH_2CH=CBr_2$ |
| $CH_3$ | $CH_3$ | $CH_2CH=C(CH_3)Cl$ |
| $CH_3$ | $CH_3$ | $CH_2CH=C(CF_3)Cl$ |
| $CH_3$ | $CH_3$ | $CH_2CH=C(CH_3)Br$ |
| $CH_3$ | $CH_3$ | $CH_2CH=C(CF_3)Br$ |
| $CH_3$ | $CH_3$ | $CH=CHCF_3$ |
| $CH_3$ | $CH_3$ | $CH=CHCH_2CF_3$ |
| $CH_3$ | $CH_3$ | $CH_2CH=CHCH_2CF_3$ |

TABLE 3-continued

| R¹ | R² | R³ |
|---|---|---|
| CH₃ | CH₃ | C≡CH |
| CH₃ | CH₃ | C≡CCH₃ |
| CH₃ | CH₃ | CH₂C≡CH |
| CH₃ | CH₃ | C≡CCH₂CH₃ |
| CH₃ | CH₃ | CH₂C≡CCH₃ |
| CH₃ | CH₃ | CH₂CH₂C≡CH |
| CH₃ | CH₃ | CH(CH₃)C≡CH |
| CH₃ | CH₃ | C≡CCH₂CH₂CH₃ |
| CH₃ | CH₃ | CH₂C≡CCH₂CH₃ |
| CH₃ | CH₃ | CH₂CH₂C≡CCH₃ |
| CH₃ | CH₃ | CH₂CH₂CH₂C≡CH |
| CH₃ | CH₃ | CH₂CH₂CH₂C≡CCH₃ |
| CH₃ | CH₃ | C≡CCl |
| CH₃ | CH₃ | CH₂C≡CCl |
| CH₃ | CH₃ | CH₂CH₂C≡CCl |
| CH₃ | CH₃ | CH₂CH₂CH₂C≡CCl |
| CH₃ | CH₃ | C≡CBr |
| CH₃ | CH₃ | CH₂C≡CBr |
| CH₃ | CH₃ | CH₂CH₂C≡CBr |
| CH₃ | CH₃ | CH₂CH₂CH₂C≡CBr |
| CH₃ | CH₃ | CH₂CH₂CH₂CH₂C≡CCl |
| CH₃ | CH₃ | CH₂OH |
| CH₃ | CH₃ | CH₂CH₂OH |
| CH₃ | CH₃ | CH₂CH₂CH₂OH |
| CH₃ | CH₃ | CH₂CH₂CH₂CH₂OH |

TABLE 4

| R¹ | R² | R³ |
|---|---|---|
| CH₃ | CH₃ | CH₂CH₂CH₂CH₂CH₂OH |
| CH₃ | CH₃ | CH₂OCH₃ |
| CH₃ | CH₃ | CH₂OCH₂CH₃ |
| CH₃ | CH₃ | CH₂OCH₂CH₂CH₃ |
| CH₃ | CH₃ | CH₂OCH(CH₃)₂ |
| CH₃ | CH₃ | CH₂OCH₂CH₂CH₂CH₃ |
| CH₃ | CH₃ | CH₂OCH₂CH₂CH₂CH₂CH₃ |
| CH₃ | CH₃ | CH₂CH₂OCH₃ |
| CH₃ | CH₃ | CH₂CH₂OCH₂CH₃ |
| CH₃ | CH₃ | CH₂CH₂OCH₂CH₂CH₃ |
| CH₃ | CH₃ | CH₂CH₂OCH(CH₃)₂ |
| CH₃ | CH₃ | CH₂CH₂CH₂OCH₃ |
| CH₃ | CH₃ | C(=O)OCH₃ |
| CH₃ | CH₃ | C(=O)OCH₂CH₃ |
| CH₃ | CH₃ | C(=O)OCH₂CH₂CH₃ |
| CH₃ | CH₃ | C(=O)OCH(CH₃)₂ |
| CH₃ | CH₃ | C(=O)OCH₂CH₂CH₂CH₃ |
| CH₃ | CH₃ | C(=O)OCH₂CH=CH₂ |
| CH₃ | CH₃ | C(=O)OCH(CH₃)CH=CH₂ |
| CH₃ | CH₃ | C(=O)OCH(CH₃)C(CH₃)=CH₂ |
| CH₃ | CH₃ | C(=O)OCH₂CH=CHCH₃ |
| CH₃ | CH₃ | C(=O)OCH(CH₃)CH=CHCH₃ |
| CH₃ | CH₃ | C(=O)OCH₂CH=C(CH₃)₂ |
| CH₃ | CH₃ | C(=O)OCH₂CH=CHCl |
| CH₃ | CH₃ | C(=O)OCH₂CH=CCl₂ |
| CH₃ | CH₃ | C(=O)OCH₂CH=CCl(CH₃) |
| CH₃ | CH₃ | C(=O)OCH₂CH=CHBr |
| CH₃ | CH₃ | C(=O)OCH₂CH=CBr₂ |
| CH₃ | CH₃ | C(=O)OCH₂CH=CBr(CH₃) |

TABLE 5

| R¹ | R² | R³ |
|---|---|---|
| CH₃ | CH₂CH₃ | H |
| CH₃ | CH₂CH₃ | CH₃ |
| CH₃ | CH₂CH₃ | CH₂CH₃ |
| CH₃ | CH₂CH₃ | CH₂CH₂CH₃ |
| CH₃ | CH₂CH₃ | CH(CH₃)₂ |
| CH₃ | CH₂CH₃ | CH₂CH₂CH₂CH₃ |
| CH₃ | CH₂CH₃ | CH(CH₃)CH₂CH₃ |
| CH₃ | CH₂CH₃ | CH₂CH(CH₃)₂ |

TABLE 5-continued

| R¹ | R² | R³ |
|---|---|---|
| CH₃ | CH₂CH₃ | CH₂CH₂CH₂CH₂CH₃ |
| CH₃ | CH₂CH₃ | CH₂CH₂CH(CH₃)₂ |
| CH₃ | CH₂CH₃ | CH(CH₃)CH₂CH₂CH₃ |
| CH₃ | CH₂CH₃ | CH₂CH(CH₃)CH₂CH₃ |
| CH₃ | CH₂CH₃ | CH(CH₃)CH(CH₃)₂ |
| CH₃ | CH₂CH₃ | CH₂CH₂CH₂CH₂CH₂CH₃ |
| CH₃ | CH₂CH₃ | CH₂F |
| CH₃ | CH₂CH₃ | CF₃ |
| CH₃ | CH₂CH₃ | CH₂CH₂F |
| CH₃ | CH₂CH₃ | CH₂CF₃ |
| CH₃ | CH₂CH₃ | CH₂CH₂CH₂F |
| CH₃ | CH₂CH₃ | CH₂CH₂CF₃ |
| CH₃ | CH₂CH₃ | CH₂CH₂CH₂CH₂F |
| CH₃ | CH₂CH₃ | CH₂CH₂CH₂CF₃ |
| CH₃ | CH₂CH₃ | CH₂CH₂CH₂CH₂CF₃ |
| CH₃ | CH₂CH₃ | CH₂CH₂Cl |
| CH₃ | CH₂CH₃ | CHClCH₂Cl |
| CH₃ | CH₂CH₃ | CH₂CH₂Br |
| CH₃ | CH₂CH₃ | CHBrCH₂Br |
| CH₃ | CH₂CH₃ | CH₂CH₂CH₂Cl |
| CH₃ | CH₂CH₃ | CH₂CHClCH₂Cl |
| CH₃ | CH₂CH₃ | CH₂CH₂CH₂Br |
| CH₃ | CH₂CH₃ | CH₂CHBrCH₂Br |
| CH₃ | CH₂CH₃ | CH₂CH₂CH₂CH₂Cl |
| CH₃ | CH₂CH₃ | CH₂CH₂CH₂CH₂Br |
| CH₃ | CH₂CH₃ | CH₂CH₂CH₂CH₂CH₂Cl |
| CH₃ | CH₂CH₃ | CH₂CH₂CH₂CH₂CH₂Br |

TABLE 6

| R¹ | R² | R³ |
|---|---|---|
| CH₃ | CH₂CH₃ | CH₂CH₂CH₂CH₂CH₂CH₂Cl |
| CH₃ | CH₂CH₃ | CH₂CH₂CH₂CH₂CH₂CH₂Br |
| CH₃ | CH₂CH₃ | CH=CH₂ |
| CH₃ | CH₂CH₃ | CH₂CH=CH₂ |
| CH₃ | CH₂CH₃ | CH=CHCH₃ |
| CH₃ | CH₂CH₃ | C(CH₃)=CH₂ |
| CH₃ | CH₂CH₃ | CH=CHCH₂CH₃ |
| CH₃ | CH₂CH₃ | CH₂CH=CHCH₃ |
| CH₃ | CH₂CH₃ | CH₂CH₂CH=CH₂ |
| CH₃ | CH₂CH₃ | C(CH₃)=CHCH₃ |
| CH₃ | CH₂CH₃ | CH(CH₃)CH=CH₂ |
| CH₃ | CH₂CH₃ | CH=C(CH₃)₂ |
| CH₃ | CH₂CH₃ | CH₂C(CH₃)=CH₂ |
| CH₃ | CH₂CH₃ | C(CH₂CH₃)=CH₂ |
| CH₃ | CH₂CH₃ | CH=CHCH₂CH₂CH₃ |
| CH₃ | CH₂CH₃ | C(CH₃)=CHCH₂CH₃ |
| CH₃ | CH₂CH₃ | CH(CH₃)CH=CHCH₃ |
| CH₃ | CH₂CH₃ | CH(CH₃)CH₂CH=CH₂ |
| CH₃ | CH₂CH₃ | CH=C(CH₃)CH₂CH₃ |
| CH₃ | CH₂CH₃ | CH₂C(CH₃)=CHCH₃ |
| CH₃ | CH₂CH₃ | CH₂CH(CH₃)CH=CH₂ |
| CH₃ | CH₂CH₃ | CH=CHCH(CH₃)₂ |
| CH₃ | CH₂CH₃ | CH₂CH=C(CH₃)₂ |
| CH₃ | CH₂CH₃ | CH₂CH₂C(CH₂)=CH₂ |
| CH₃ | CH₂CH₃ | CH₂CH=C(CH₃)₂ |
| CH₃ | CH₂CH₃ | CH=CHCH₂CH₂CH₂CH₃ |
| CH₃ | CH₂CH₃ | CH=CHCl |
| CH₃ | CH₂CH₃ | CH=CCl₂ |
| CH₃ | CH₂CH₃ | CH=C(CH₃)Cl |
| CH₃ | CH₂CH₃ | CH₂CH=CHCl |
| CH₃ | CH₂CH₃ | CH₂CCl=CHCl |
| CH₃ | CH₂CH₃ | CH₂CH=CCl₂ |
| CH₃ | CH₂CH₃ | CH=CHBr |
| CH₃ | CH₂CH₃ | CH=CBr₂ |
| CH₃ | CH₂CH₃ | CH=C(CH₃)Br |

TABLE 7

| R¹ | R² | R³ |
|---|---|---|
| $CH_3$ | $CH_2CH_3$ | $CH_2CH=CHBr$ |
| $CH_3$ | $CH_2CH_3$ | $CH_2CBr=CHBr$ |
| $CH_3$ | $CH_2CH_3$ | $CH_2CH=CBr_2$ |
| $CH_3$ | $CH_2CH_3$ | $CH_2CH=C(CH_3)Cl$ |
| $CH_3$ | $CH_2CH_3$ | $CH_2CH=C(CF_3)Cl$ |
| $CH_3$ | $CH_2CH_3$ | $CH_2CH=C(CH_3)Br$ |
| $CH_3$ | $CH_2CH_3$ | $CH_2CH=C(CF_3)Br$ |
| $CH_3$ | $CH_2CH_3$ | $CH=CHCF_3$ |
| $CH_3$ | $CH_2CH_3$ | $CH=CHCH_2CF_3$ |
| $CH_3$ | $CH_2CH_3$ | $CH_2CH=CHCH_2CF_3$ |
| $CH_3$ | $CH_2CH_3$ | $C\equiv CH$ |
| $CH_3$ | $CH_2CH_3$ | $C\equiv CCH_3$ |
| $CH_3$ | $CH_2CH_3$ | $CH_2C\equiv CH$ |
| $CH_3$ | $CH_2CH_3$ | $C\equiv CCH_2CH_3$ |
| $CH_3$ | $CH_2CH_3$ | $CH_2C\equiv CCH_3$ |
| $CH_3$ | $CH_2CH_3$ | $CH_2CH_2C\equiv CH$ |
| $CH_3$ | $CH_2CH_3$ | $CH(CH_3)C\equiv CH$ |
| $CH_3$ | $CH_2CH_3$ | $C\equiv CCH_2CH_2CH_3$ |
| $CH_3$ | $CH_2CH_3$ | $CH_2C\equiv CCH_2CH_3$ |
| $CH_3$ | $CH_2CH_3$ | $CH_2CH_2C\equiv CCH_3$ |
| $CH_3$ | $CH_2CH_3$ | $CH_2CH_2CH_2C\equiv CH$ |
| $CH_3$ | $CH_2CH_3$ | $CH_2CH_2CH_2C\equiv CCH_3$ |
| $CH_3$ | $CH_2CH_3$ | $C\equiv CCl$ |
| $CH_3$ | $CH_2CH_3$ | $CH_2C\equiv CCl$ |
| $CH_3$ | $CH_2CH_3$ | $CH_2CH_2C\equiv CCl$ |
| $CH_3$ | $CH_2CH_3$ | $CH_2CH_2CH_2C\equiv CCl$ |
| $CH_3$ | $CH_2CH_3$ | $C\equiv CBr$ |
| $CH_3$ | $CH_2CH_3$ | $CH_2C\equiv CBr$ |
| $CH_3$ | $CH_2CH_3$ | $CH_2CH_2C\equiv CBr$ |
| $CH_3$ | $CH_2CH_3$ | $CH_2CH_2CH_2C\equiv CBr$ |
| $CH_3$ | $CH_2CH_3$ | $CH_2CH_2CH_2CH_2C\equiv CCl$ |
| $CH_3$ | $CH_2CH_3$ | $CH_2OH$ |
| $CH_3$ | $CH_2CH_3$ | $CH_2CH_2OH$ |
| $CH_3$ | $CH_2CH_3$ | $CH_2CH_2CH_2OH$ |
| $CH_3$ | $CH_2CH_3$ | $CH_2CH_2CH_2CH_2OH$ |

TABLE 8

| R¹ | R² | R³ |
|---|---|---|
| $CH_3$ | $CH_2CH_3$ | $CH_2CH_2CH_2CH_2CH_2OH$ |
| $CH_3$ | $CH_2CH_3$ | $CH_2OCH_3$ |
| $CH_3$ | $CH_2CH_3$ | $CH_2OCH_2CH_3$ |
| $CH_3$ | $CH_2CH_3$ | $CH_2OCH_2CH_2CH_3$ |
| $CH_3$ | $CH_2CH_3$ | $CH_2OCH(CH_3)_2$ |
| $CH_3$ | $CH_2CH_3$ | $CH_2OCH_2CH_2CH_2CH_3$ |
| $CH_3$ | $CH_2CH_3$ | $CH_2OCH_2CH_2CH_2CH_2CH_3$ |
| $CH_3$ | $CH_2CH_3$ | $CH_2CH_2OCH_3$ |
| $CH_3$ | $CH_2CH_3$ | $CH_2CH_2OCH_2CH_3$ |
| $CH_3$ | $CH_2CH_3$ | $CH_2CH_2OCH_2CH_2CH_3$ |
| $CH_3$ | $CH_2CH_3$ | $CH_2CH_2OCH(CH_3)_2$ |
| $CH_3$ | $CH_2CH_3$ | $CH_2CH_2CH_2OCH_3$ |
| $CH_3$ | $CH_2CH_3$ | $C(=O)OCH_3$ |
| $CH_3$ | $CH_2CH_3$ | $C(=O)OCH_2CH_3$ |
| $CH_3$ | $CH_2CH_3$ | $C(=O)OCH_2CH_2CH_3$ |
| $CH_3$ | $CH_2CH_3$ | $C(=O)OCH(CH_3)_2$ |
| $CH_3$ | $CH_2CH_3$ | $C(=O)OCH_2CH_2CH_2CH_2$ |
| $CH_3$ | $CH_2CH_3$ | $C(=O)OCH_2CH=CH_2$ |
| $CH_3$ | $CH_2CH_3$ | $C(=O)OCH(CH_3)CH=CH_2$ |
| $CH_3$ | $CH_2CH_3$ | $C(=O)OCH(CH_3)C(CH_3)=CH_2$ |
| $CH_3$ | $CH_2CH_3$ | $C(=O)OCH_2CH=CHCH_3$ |
| $CH_3$ | $CH_2CH_3$ | $C(=O)OCH(CH_3)CH=CHCH_3$ |
| $CH_3$ | $CH_2CH_3$ | $C(=O)OCH_2CH=C(CH_3)_2$ |
| $CH_3$ | $CH_2CH_3$ | $C(=O)OCH_2CH=CHCl$ |
| $CH_3$ | $CH_2CH_3$ | $C(=O)OCH_2CH=CCl_2$ |
| $CH_3$ | $CH_2CH_3$ | $C(=O)OCH_2CH=CCl(CH_3)$ |
| $CH_3$ | $CH_2CH_3$ | $C(=O)OCH_2CH=CHBr$ |
| $CH_3$ | $CH_2CH_3$ | $C(=O)OCH_2CH=CBr_2$ |
| $CH_3$ | $CH_2CH_3$ | $C(=O)OCH_2CH=CBr(CH_3)$ |

TABLE 9

| R¹ | R² | R³ |
|---|---|---|
| $CH_3$ | $CH(CH_3)_2$ | $H$ |
| $CH_3$ | $CH(CH_3)_2$ | $CH_3$ |
| $CH_3$ | $CH(CH_3)_2$ | $CH_2CH_3$ |
| $CH_3$ | $CH(CH_3)_2$ | $CH_2CH_2CH_3$ |
| $CH_3$ | $CH(CH_3)_2$ | $CH(CH_3)_2$ |
| $CH_3$ | $CH(CH_3)_2$ | $CH_2CH_2CH_2CH_3$ |
| $CH_3$ | $CH(CH_3)_2$ | $CH(CH_3)CH_2CH_3$ |
| $CH_3$ | $CH(CH_3)_2$ | $CH_2CH(CH_3)_2$ |
| $CH_3$ | $CH(CH_3)_2$ | $CH_2CH_2CH_2CH_2CH_3$ |
| $CH_3$ | $CH(CH_3)_2$ | $CH_2CH_2CH(CH_3)_2$ |
| $CH_3$ | $CH(CH_3)_2$ | $CH(CH_3)CH_2CH_2CH_3$ |
| $CH_3$ | $CH(CH_3)_2$ | $CH_2CH(CH_3)CH_2CH_3$ |
| $CH_3$ | $CH(CH_3)_2$ | $CH(CH_3)CH(CH_3)_2$ |
| $CH_3$ | $CH(CH_3)_2$ | $CH_2CH_2CH_2CH_2CH_2CH_3$ |
| $CH_3$ | $CH(CH_3)_2$ | $CH_2F$ |
| $CH_3$ | $CH(CH_3)_2$ | $CF_3$ |
| $CH_3$ | $CH(CH_3)_2$ | $CH_2CH_2F$ |
| $CH_3$ | $CH(CH_3)_2$ | $CH_2CF_3$ |
| $CH_3$ | $CH(CH_3)_2$ | $CH_2CH_2CH_2F$ |
| $CH_3$ | $CH(CH_3)_2$ | $CH_2CH_2CF_3$ |
| $CH_3$ | $CH(CH_3)_2$ | $CH_2CH_2CH_2CH_2F$ |
| $CH_3$ | $CH(CH_3)_2$ | $CH_2CH_2CH_2CF_3$ |
| $CH_3$ | $CH(CH_3)_2$ | $CH_2CH_2CH_2CH_2CF_3$ |
| $CH_3$ | $CH(CH_3)_2$ | $CH_2CH_2Cl$ |
| $CH_3$ | $CH(CH_3)_2$ | $CHClCH_2Cl$ |
| $CH_3$ | $CH(CH_3)_2$ | $CH_2CH_2Br$ |
| $CH_3$ | $CH(CH_3)_2$ | $CHBrCH_2Br$ |
| $CH_3$ | $CH(CH_3)_2$ | $CH_2CH_2CH_2Cl$ |
| $CH_3$ | $CH(CH_3)_2$ | $CH_2CHClCH_2Cl$ |
| $CH_3$ | $CH(CH_3)_2$ | $CH_2CH_2CH_2Br$ |
| $CH_3$ | $CH(CH_3)_2$ | $CH_2CHBrCH_2Br$ |
| $CH_3$ | $CH(CH_3)_2$ | $CH_2CH_2CH_2CH_2Cl$ |
| $CH_3$ | $CH(CH_3)_2$ | $CH_2CH_2CH_2CH_2Br$ |
| $CH_3$ | $CH(CH_3)_2$ | $CH_2CH_2CH_2CH_2CH_2Cl$ |
| $CH_3$ | $CH(CH_3)_2$ | $CH_2CH_2CH_2CH_2CH_2Br$ |

TABLE 10

| R¹ | R² | R³ |
|---|---|---|
| $CH_3$ | $CH(CH_3)_2$ | $CH_2CH_2CH_2CH_2CH_2CH_2Cl$ |
| $CH_3$ | $CH(CH_3)_2$ | $CH_2CH_2CH_2CH_2CH_2CH_2Br$ |
| $CH_3$ | $CH(CH_3)_2$ | $CH=CH_2$ |
| $CH_3$ | $CH(CH_3)_2$ | $CH_2CH=CH_2$ |
| $CH_3$ | $CH(CH_3)_2$ | $CH=CHCH_3$ |
| $CH_3$ | $CH(CH_3)_2$ | $C(CH_3)=CH_2$ |
| $CH_3$ | $CH(CH_3)_2$ | $CH=CHCH_2CH_3$ |
| $CH_3$ | $CH(CH_3)_2$ | $CH_2CH=CHCH_3$ |
| $CH_3$ | $CH(CH_3)_2$ | $CH_2CH_2CH=CH_2$ |
| $CH_3$ | $CH(CH_3)_2$ | $C(CH_3)=CHCH_3$ |
| $CH_3$ | $CH(CH_3)_2$ | $CH(CH_3)CH=CH_2$ |
| $CH_3$ | $CH(CH_3)_2$ | $CH=C(CH_3)_2$ |
| $CH_3$ | $CH(CH_3)_2$ | $CH_2C(CH_3)=CH_2$ |
| $CH_3$ | $CH(CH_3)_2$ | $C(CH_2CH_3)=CH_2$ |
| $CH_3$ | $CH(CH_3)_2$ | $CH=CHCH_2CH_3$ |
| $CH_3$ | $CH(CH_3)_2$ | $C(CH_3)=CHCH_2CH_3$ |
| $CH_3$ | $CH(CH_3)_2$ | $CH(CH_3)CH=CHCH_3$ |
| $CH_3$ | $CH(CH_3)_2$ | $CH(CH_3)CH_2CH=CH_2$ |
| $CH_3$ | $CH(CH_3)_2$ | $CH=C(CH_3)CH_2CH_3$ |
| $CH_3$ | $CH(CH_3)_2$ | $CH_2C(CH_3)=CHCH_3$ |
| $CH_3$ | $CH(CH_3)_2$ | $CH_2CH(CH_3)CH=CH_2$ |
| $CH_3$ | $CH(CH_3)_2$ | $CH=CHCH(CH_3)_2$ |
| $CH_3$ | $CH(CH_3)_2$ | $CH_2CH=C(CH_3)_2$ |
| $CH_3$ | $CH(CH_3)_2$ | $CH_2CH_2C(CH_2)=CH_2$ |
| $CH_3$ | $CH(CH_3)_2$ | $CH_2CH=C(CH_3)_2$ |
| $CH_3$ | $CH(CH_3)_2$ | $CH=CHCH_2CH_2CH_3$ |
| $CH_3$ | $CH(CH_3)_2$ | $CH=CHCl$ |
| $CH_3$ | $CH(CH_3)_2$ | $CH=CCl_2$ |
| $CH_3$ | $CH(CH_3)_2$ | $CH=C(CH_3)Cl$ |
| $CH_3$ | $CH(CH_3)_2$ | $CH_2CH=CHCl$ |
| $CH_3$ | $CH(CH_3)_2$ | $CH_2CCl=CHCl$ |
| $CH_3$ | $CH(CH_3)_2$ | $CH_2CH=CCl_2$ |
| $CH_3$ | $CH(CH_3)_2$ | $CH=CHBr$ |
| $CH_3$ | $CH(CH_3)_2$ | $CH=CBr_2$ |
| $CH_3$ | $CH(CH_3)_2$ | $CH=C(CH_3)Br$ |

TABLE 11

| R¹ | R² | R³ |
|---|---|---|
| CH₃ | CH(CH₃)₂ | CH₂CH=CHBr |
| CH₃ | CH(CH₃)₂ | CH₂CBr=CHBr |
| CH₃ | CH(CH₃)₂ | CH₂CH=CBr₂ |
| CH₃ | CH(CH₃)₂ | CH₂CH=C(CH₃)Cl |
| CH₃ | CH(CH₃)₂ | CH₂CH=C(CF₃)Cl |
| CH₃ | CH(CH₃)₂ | CH₂CH=C(CH₃)Br |
| CH₃ | CH(CH₃)₂ | CH₂CH=C(CF₃)Br |
| CH₃ | CH(CH₃)₂ | CH=CHCF₃ |
| CH₃ | CH(CH₃)₂ | CH=CHCH₂CF₃ |
| CH₃ | CH(CH₃)₂ | CH₂CH=CHCH₂CF₃ |
| CH₃ | CH(CH₃)₂ | C≡CH |
| CH₃ | CH(CH₃)₂ | C≡CCH₃ |
| CH₃ | CH(CH₃)₂ | CH₂C≡CH |
| CH₃ | CH(CH₃)₂ | C≡CCH₂CH₃ |
| CH₃ | CH(CH₃)₂ | CH₂C≡CCH₃ |
| CH₃ | CH(CH₃)₂ | CH₂CH₂C≡CH |
| CH₃ | CH(CH₃)₂ | CH(CH₃)C≡CH |
| CH₃ | CH(CH₃)₂ | C≡CCH₂CH₂CH₃ |
| CH₃ | CH(CH₃)₂ | CH₂C≡CCH₂CH₃ |
| CH₃ | CH(CH₃)₂ | CH₂CH₂C≡CCH₃ |
| CH₃ | CH(CH₃)₂ | CH₂CH₂CH₂C≡CH |
| CH₃ | CH(CH₃)₂ | CH₂CH₂CH₂C≡CCH₃ |
| CH₃ | CH(CH₃)₂ | C≡CCl |
| CH₃ | CH(CH₃)₂ | CH₂C≡CCl |
| CH₃ | CH(CH₃)₂ | CH₂C≡CCl |
| CH₃ | CH(CH₃)₂ | CH₂CH₂CH₂C≡CCl |
| CH₃ | CH(CH₃)₂ | C≡CBr |
| CH₃ | CH(CH₃)₂ | CH₂C≡CBr |
| CH₃ | CH(CH₃)₂ | CH₂CH₂C≡CBr |
| CH₃ | CH(CH₃)₂ | CH₂CH₂CH₂C≡CBr |
| CH₃ | CH(CH₃)₂ | CH₂CH₂CH₂CH₂C≡CCl |
| CH₃ | CH(CH₃)₂ | CH₂OH |
| CH₃ | CH(CH₃)₂ | CH₂CH₂OH |
| CH₃ | CH(CH₃)₂ | CH₂CH₂CH₂OH |
| CH₃ | CH(CH₃)₂ | CH₂CH₂CH₂CH₂OH |

TABLE 12

| R¹ | R² | R³ |
|---|---|---|
| CH₃ | CH(CH₃)₂ | CH₂CH₂CH₂CH₂CH₂OH |
| CH₃ | CH(CH₃)₂ | CH₂OCH₃ |
| CH₃ | CH(CH₃)₂ | CH₂OCH₂CH₃ |
| CH₃ | CH(CH₃)₂ | CH₂OCH₂CH₂CH₃ |
| CH₃ | CH(CH₃)₂ | CH₂OCH(CH₃)₂ |
| CH₃ | CH(CH₃)₂ | CH₂OCH₂CH₂CH₂CH₃ |
| CH₃ | CH(CH₃)₂ | CH₂OCH₂CH₂CH₂CH₂CH₃ |
| CH₃ | CH(CH₃)₂ | CH₂CH₂OCH₃ |
| CH₃ | CH(CH₃)₂ | CH₂CH₂OCH₂CH₃ |
| CH₃ | CH(CH₃)₂ | CH₂CH₂OCH₂CH₂CH₃ |
| CH₃ | CH(CH₃)₂ | CH₂CH₂OCH(CH₃)₂ |
| CH₃ | CH(CH₃)₂ | CH₂CH₂CH₂OCH₃ |
| CH₃ | CH(CH₃)₂ | C(=O)OCH₃ |
| CH₃ | CH(CH₃)₂ | C(=O)OCH₂CH₃ |
| CH₃ | CH(CH₃)₂ | C(=O)OCH₂CH₂CH₃ |
| CH₃ | CH(CH₃)₂ | C(=O)OCH(CH₃)₂ |
| CH₃ | CH(CH₃)₂ | C(=O)OCH₂CH₂CH₂CH₃ |
| CH₃ | CH(CH₃)₂ | C(=O)OCH₂CH=CH₂ |
| CH₃ | CH(CH₃)₂ | C(=O)OCH(CH₃)CH=CH₂ |
| CH₃ | CH(CH₃)₂ | C(=O)OCH(CH₃)C(CH₃)=CH₂ |
| CH₃ | CH(CH₃)₂ | C(=O)OCH₂CH=CHCH₃ |
| CH₃ | CH(CH₃)₂ | C(=O)OCH(CH₃)CH=CHCH₃ |
| CH₃ | CH(CH₃)₂ | C(=O)OCH₂CH=C(CH₃)₂ |
| CH₃ | CH(CH₃)₂ | C(=O)OCH₂CH=CHCl |
| CH₃ | CH(CH₃)₂ | C(=O)OCH₂CH=CCl₂ |
| CH₃ | CH(CH₃)₂ | C(=O)OCH₂CH=CCl(CH₃) |
| CH₃ | CH(CH₃)₂ | C(=O)OCH₂CH=CHBr |
| CH₃ | CH(CH₃)₂ | C(=O)OCH₂CH=CBr₂ |
| CH₃ | CH(CH₃)₂ | C(=O)OCH₂CH=CBr(CH₃) |

TABLE 13

| R¹ | R² | R³ |
|---|---|---|
| CH₃ | C(CH₃)₃ | H |
| CH₃ | C(CH₃)₃ | CH₃ |
| CH₃ | C(CH₃)₃ | CH₂CH₃ |
| CH₃ | C(CH₃)₃ | CH₂CH₂CH₃ |
| CH₃ | C(CH₃)₃ | CH(CH₃)₂ |
| CH₃ | C(CH₃)₃ | CH₂CH₂CH₂CH₃ |
| CH₃ | C(CH₃)₃ | CH(CH₃)CH₂CH₃ |
| CH₃ | C(CH₃)₃ | CH₂CH(CH₃)₂ |
| CH₃ | C(CH₃)₃ | CH₂CH₂CH₂CH₂CH₃ |
| CH₃ | C(CH₃)₃ | CH₂CH₂CH(CH₃)₂ |
| CH₃ | C(CH₃)₃ | CH(CH₃)CH₂CH₂CH₃ |
| CH₃ | C(CH₃)₃ | CH(CH₃)CH₂CH₂CH₃ |
| CH₃ | C(CH₃)₃ | CH(CH₃)CH(CH₃)₂ |
| CH₃ | C(CH₃)₃ | CH₂CH₂CH₂CH₂CH₂CH₃ |
| CH₃ | C(CH₃)₃ | CH₂F |
| CH₃ | C(CH₃)₃ | CF₃ |
| CH₃ | C(CH₃)₃ | CH₂CH₂F |
| CH₃ | C(CH₃)₃ | CH₂CF₃ |
| CH₃ | C(CH₃)₃ | CH₂CH₂CH₂F |
| CH₃ | C(CH₃)₃ | CH₂CH₂CF₃ |
| CH₃ | C(CH₃)₃ | CH₂CH₂CH₂CH₂F |
| CH₃ | C(CH₃)₃ | CH₂CH₂CH₂CF₃ |
| CH₃ | C(CH₃)₃ | CH₂CH₂CH₂CH₂CF₃ |
| CH₃ | C(CH₃)₃ | CH₂CH₂Cl |
| CH₃ | C(CH₃)₃ | CHClCH₂Cl |
| CH₃ | C(CH₃)₃ | CH₂CH₂Br |
| CH₃ | C(CH₃)₃ | CHBrCH₂Br |
| CH₃ | C(CH₃)₃ | CH₂CH₂CH₂Cl |
| CH₃ | C(CH₃)₃ | CH₂CHClCH₂Cl |
| CH₃ | C(CH₃)₃ | CH₂CH₂CH₂Br |
| CH₃ | C(CH₃)₃ | CH₂CHBrCH₂Br |
| CH₃ | C(CH₃)₃ | CH₂CH₂CH₂CH₂Cl |
| CH₃ | C(CH₃)₃ | CH₂CH₂CH₂CH₂Br |
| CH₃ | C(CH₃)₃ | CH₂CH₂CH₂CH₂CH₂Cl |
| CH₃ | C(CH₃)₃ | CH₂CH₂CH₂CH₂CH₂Br |

TABLE 14

| R¹ | R² | R³ |
|---|---|---|
| CH₃ | C(CH₃)₃ | CH₂CH₂CH₂CH₂CH₂CH₂Cl |
| CH₃ | C(CH₃)₃ | CH₂CH₂CH₂CH₂CH₂CH₂Br |
| CH₃ | C(CH₃)₃ | CH=CH₂ |
| CH₃ | C(CH₃)₃ | CH₂CH=CH₂ |
| CH₃ | C(CH₃)₃ | CH=CHCH₃ |
| CH₃ | C(CH₃)₃ | C(CH₃)=CH₂ |
| CH₃ | C(CH₃)₃ | CH=CHCH₂CH₃ |
| CH₃ | C(CH₃)₃ | CH₂CH=CHCH₃ |
| CH₃ | C(CH₃)₃ | CH₂CH₂CH=CH₂ |
| CH₃ | C(CH₃)₃ | C(CH₃)=CHCH₃ |
| CH₃ | C(CH₃)₃ | CH(CH₃)CH=CH₂ |
| CH₃ | C(CH₃)₃ | CH=C(CH₃)₂ |
| CH₃ | C(CH₃)₃ | CH₂C(CH₃)=CH₂ |
| CH₃ | C(CH₃)₃ | C(CH₂CH₃)=CH₂ |
| CH₃ | C(CH₃)₃ | CH=CHCH₂CH₂CH₃ |
| CH₃ | C(CH₃)₃ | C(CH₃)=CHCH₂CH₃ |
| CH₃ | C(CH₃)₃ | CH(CH₃)CH=CHCH₃ |
| CH₃ | C(CH₃)₃ | CH(CH₃)CH₂CH=CH₂ |
| CH₃ | C(CH₃)₃ | CH=C(CH₃)CH₂CH₃ |
| CH₃ | C(CH₃)₃ | CH₂C(CH₃)=CHCH₃ |
| CH₃ | C(CH₃)₃ | CH₂CH(CH₃)CH=CH₂ |
| CH₃ | C(CH₃)₃ | CH=CHCH(CH₃)₂ |
| CH₃ | C(CH₃)₃ | CH₂CH=C(CH₃)₂ |
| CH₃ | C(CH₃)₃ | CH₂C(CH₂)C(CH₂)=CH₂ |
| CH₃ | C(CH₃)₃ | CH₂CH=C(CH₃)₂ |
| CH₃ | C(CH₃)₃ | CH=CHCH₂CH₂CH₂CH₃ |
| CH₃ | C(CH₃)₃ | CH=CHCl |
| CH₃ | C(CH₃)₃ | CH=CCl₂ |
| CH₃ | C(CH₃)₃ | CH=C(CH₃)Cl |
| CH₃ | C(CH₃)₃ | CH₂CH=CHCl |
| CH₃ | C(CH₃)₃ | CH₂CCl=CHCl |
| CH₃ | C(CH₃)₃ | CH₂CH=CCl₂ |
| CH₃ | C(CH₃)₃ | CH=CHBr |

TABLE 14-continued

| R¹ | R² | R³ |
|---|---|---|
| CH₃ | C(CH₃)₃ | CH=CBr₂ |
| CH₃ | C(CH₃)₃ | CH=C(CH₃)Br |

TABLE 15

| R¹ | R² | R³ |
|---|---|---|
| CH₃ | C(CH₃)₃ | CH₂CH=CHBr |
| CH₃ | C(CH₃)₃ | CH₂CBr=CHBr |
| CH₃ | C(CH₃)₃ | CH₂CH=CBr₂ |
| CH₃ | C(CH₃)₃ | CH₂CH=C(CH₃)Cl |
| CH₃ | C(CH₃)₃ | CH₂CH=C(CF₃)Cl |
| CH₃ | C(CH₃)₃ | CH₂CH=C(CH₃)Br |
| CH₃ | C(CH₃)₃ | CH₂CH=C(CF₃)Br |
| CH₃ | C(CH₃)₃ | CH=CHCF₃ |
| CH₃ | C(CH₃)₃ | CH=CHCH₂CF₃ |
| CH₃ | C(CH₃)₃ | CH₂CH=CHCH₂CF₃ |
| CH₃ | C(CH₃)₃ | C≡CH |
| CH₃ | C(CH₃)₃ | C≡CCH₃ |
| CH₃ | C(CH₃)₃ | CH₂C≡CH |
| CH₃ | C(CH₃)₃ | C≡CCH₂CH₃ |
| CH₃ | C(CH₃)₃ | CH₂C≡CCH₃ |
| CH₃ | C(CH₃)₃ | CH₂CH₂C≡CH |
| CH₃ | C(CH₃)₃ | CH(CH₃)C≡CH |
| CH₃ | C(CH₃)₃ | C≡CCH₂CH₃ |
| CH₃ | C(CH₃)₃ | CH₂C≡CCH₂CH₃ |
| CH₃ | C(CH₃)₃ | CH₂CH₂C≡CCH₃ |
| CH₃ | C(CH₃)₃ | CH₂CH₂CH₂C≡CH |
| CH₃ | C(CH₃)₃ | CH₂CH₂CH₂C≡CCH₃ |
| CH₃ | C(CH₃)₃ | C≡CCl |
| CH₃ | C(CH₃)₃ | CH₂C≡CCl |
| CH₃ | C(CH₃)₃ | CH₂CH₂C≡CCl |
| CH₃ | C(CH₃)₃ | CH₂CH₂CH₂C≡CCl |
| CH₃ | C(CH₃)₃ | C≡CBr |
| CH₃ | C(CH₃)₃ | CH₂C≡CBr |
| CH₃ | C(CH₃)₃ | CH₂CH₂C≡CBr |
| CH₃ | C(CH₃)₃ | CH₂CH₂CH₂C≡CBr |
| CH₃ | C(CH₃)₃ | CH₂CH₂CH₂CH₂C≡CCl |
| CH₃ | C(CH₃)₃ | CH₂OH |
| CH₃ | C(CH₃)₃ | CH₂CH₂OH |
| CH₃ | C(CH₃)₃ | CH₂CH₂CH₂OH |
| CH₃ | C(CH₃)₃ | CH₂CH₂CH₂CH₂OH |

TABLE 16

| R¹ | R² | R³ |
|---|---|---|
| CH₃ | C(CH₃)₃ | CH₂CH₂CH₂CH₂CH₂OH |
| CH₃ | C(CH₃)₃ | CH₂OCH₃ |
| CH₃ | C(CH₃)₃ | CH₂OCH₂CH₃ |
| CH₃ | C(CH₃)₃ | CH₂OCH₂CH₂CH₃ |
| CH₃ | C(CH₃)₃ | CH₂OCH(CH₃)₂ |
| CH₃ | C(CH₃)₃ | CH₂OCH₂CH₂CH₂CH₃ |
| CH₃ | C(CH₃)₃ | CH₂OCH₂CH₂CH₂CH₂CH₃ |
| CH₃ | C(CH₃)₃ | CH₂CH₂OCH₃ |
| CH₃ | C(CH₃)₃ | CH₂CH₂OCH₂CH₃ |
| CH₃ | C(CH₃)₃ | CH₂CH₂OCH₂CH₂CH₃ |
| CH₃ | C(CH₃)₃ | CH₂CH₂OCH(CH₃)₂ |
| CH₃ | C(CH₃)₃ | CH₂CH₂CH₂OCH₃ |
| CH₃ | C(CH₃)₃ | C(=O)OCH₃ |
| CH₃ | C(CH₃)₃ | C(=O)OCH₂CH₃ |
| CH₃ | C(CH₃)₃ | C(=O)OCH₂CH₂CH₃ |
| CH₃ | C(CH₃)₃ | C(=O)OCH(CH₃)₂ |
| CH₃ | C(CH₃)₃ | C(=O)OCH₂CH₂CH₂CH₃ |
| CH₃ | C(CH₃)₃ | C(=O)OCH₂CH=CH₂ |
| CH₃ | C(CH₃)₃ | C(=O)OCH(CH₃)CH=CH₂ |
| CH₃ | C(CH₃)₃ | C(=O)OCH(CH₃)C(CH₃)=CH₂ |
| CH₃ | C(CH₃)₃ | C(=O)OCH(CH₃)CH=CHCH₃ |
| CH₃ | C(CH₃)₃ | C(=O)OCH(CH₃)CH=CHCH₃ |
| CH₃ | C(CH₃)₃ | C(=O)OCH₂CH=C(CH₃)₂ |
| CH₃ | C(CH₃)₃ | C(=O)OCH₂CH=CHCl |
| CH₃ | C(CH₃)₃ | C(=O)OCH₂CH=CCl₂ |

TABLE 16-continued

| R¹ | R² | R³ |
|---|---|---|
| CH₃ | C(CH₃)₃ | C(=O)OCH₂CH=CCl(CH₃) |
| CH₃ | C(CH₃)₃ | C(=O)OCH₂CH=CHBr |
| CH₃ | C(CH₃)₃ | C(=O)OCH₂CH=CBr₂ |
| CH₃ | C(CH₃)₃ | C(=O)OCH₂CH=CBr(CH₃) |

TABLE 17

| R¹ | R² | R³ |
|---|---|---|
| CH₂CH₃ | CH₃ | H |
| CH₂CH₃ | CH₃ | CH₃ |
| CH₂CH₃ | CH₃ | CH₂CH₃ |
| CH₂CH₃ | CH₃ | CH₂CH₂CH₃ |
| CH₂CH₃ | CH₃ | CH(CH₃)₂ |
| CH₂CH₃ | CH₃ | CH₂CH₂CH₂CH₃ |
| CH₂CH₃ | CH₃ | CH(CH₃)CH₂CH₃ |
| CH₂CH₃ | CH₃ | CH₂CH(CH₃)₂ |
| CH₂CH₃ | CH₃ | CH₂CH₂CH₂CH₂CH₃ |
| CH₂CH₃ | CH₃ | CH₂CH₂CH(CH₃)₂ |
| CH₂CH₃ | CH₃ | CH(CH₃)CH₂CH₂CH₃ |
| CH₂CH₃ | CH₃ | CH₂CH(CH₃)CH₂CH₃ |
| CH₂CH₃ | CH₃ | CH(CH₃)CH(CH₃)₂ |
| CH₂CH₃ | CH₃ | CH₂CH₂CH₂CH₂CH₂CH₃ |
| CH₂CH₃ | CH₃ | CH₂F |
| CH₂CH₃ | CH₃ | CF₃ |
| CH₂CH₃ | CH₃ | CH₂CH₂F |
| CH₂CH₃ | CH₃ | CH₂CF₃ |
| CH₂CH₃ | CH₃ | CH₂CH₂CH₂F |
| CH₂CH₃ | CH₃ | CH₂CH₂CF₃ |
| CH₂CH₃ | CH₃ | CH₂CH₂CH₂CH₂F |
| CH₂CH₃ | CH₃ | CH₂CH₂CH₂CF₃ |
| CH₂CH₃ | CH₃ | CH₂CH₂CH₂CH₂CF₃ |
| CH₂CH₃ | CH₃ | CH₂CH₂Cl |
| CH₂CH₃ | CH₃ | CHClCH₂Cl |
| CH₂CH₃ | CH₃ | CH₂CH₂Br |
| CH₂CH₃ | CH₃ | CHBrCH₂Br |
| CH₂CH₃ | CH₃ | CH₂CH₂CH₂Cl |
| CH₂CH₃ | CH₃ | CH₂CHClCH₂Cl |
| CH₂CH₃ | CH₃ | CH₂CH₂CH₂Br |
| CH₂CH₃ | CH₃ | CH₂CHBrCH₂Br |
| CH₂CH₃ | CH₃ | CH₂CH₂CH₂CH₂Cl |
| CH₂CH₃ | CH₃ | CH₂CH₂CH₂CH₂Br |
| CH₂CH₃ | CH₃ | CH₂CH₂CH₂CH₂CH₂Cl |
| CH₂CH₃ | CH₃ | CH₂CH₂CH₂CH₂CH₂Br |

TABLE 18

| R¹ | R² | R³ |
|---|---|---|
| CH₂CH₃ | CH₃ | CH₂CH₂CH₂CH₂CH₂CH₂Cl |
| CH₂CH₃ | CH₃ | CH₂CH₂CH₂CH₂CH₂CH₂Br |
| CH₂CH₃ | CH₃ | CH=CH₂ |
| CH₂CH₃ | CH₃ | CH₂CH=CH₂ |
| CH₂CH₃ | CH₃ | CH=CHCH₃ |
| CH₂CH₃ | CH₃ | C(CH₃)=CH₂ |
| CH₂CH₃ | CH₃ | CH=CHCH₂CH₃ |
| CH₂CH₃ | CH₃ | CH₂CH=CHCH₃ |
| CH₂CH₃ | CH₃ | CH₂CH₂CH=CH₂ |
| CH₂CH₃ | CH₃ | C(CH₃)=CHCH₃ |
| CH₂CH₃ | CH₃ | CH(CH₃)CH=CH₂ |
| CH₂CH₃ | CH₃ | CH=C(CH₃)₂ |
| CH₂CH₃ | CH₃ | CH₂C(CH₃)=CH₂ |
| CH₂CH₃ | CH₃ | C(CH₃)₃=CH₂ |
| CH₂CH₃ | CH₃ | CH=CHCH₂CH₃ |
| CH₂CH₃ | CH₃ | C(CH₃)=CHCH₂CH₃ |
| CH₂CH₃ | CH₃ | CH(CH₃)CH=CHCH₃ |
| CH₂CH₃ | CH₃ | CH(CH₃)CH₂CH=CH₂ |
| CH₂CH₃ | CH₃ | CH=CH(CH₃)CH₂CH₃ |
| CH₂CH₃ | CH₃ | CH₂C(CH₃)=CHCH₃ |
| CH₂CH₃ | CH₃ | CH₂CH(CH₃)CH=CH₂ |
| CH₂CH₃ | CH₃ | CH=CHCH(CH₃)₂ |
| CH₂CH₃ | CH₃ | CH₂CH=C(CH₃)₂ |

TABLE 18-continued

| R$^1$ | R$^2$ | R$^3$ |
|---|---|---|
| CH$_2$CH$_3$ | CH$_3$ | CH$_2$CH$_2$C(CH$_2$)=CH$_2$ |
| CH$_2$CH$_3$ | CH$_3$ | CH$_2$CH=C(CH$_3$)$_2$ |
| CH$_2$CH$_3$ | CH$_3$ | CH=CHCH$_2$CH$_2$CH$_3$ |
| CH$_2$CH$_3$ | CH$_3$ | CH=CHCl |
| CH$_2$CH$_3$ | CH$_3$ | CH=CCl$_2$ |
| CH$_2$CH$_3$ | CH$_3$ | CH=C(CH$_3$)Cl |
| CH$_2$CH$_3$ | CH$_3$ | CH$_2$CH=CHCl |
| CH$_2$CH$_3$ | CH$_3$ | CH$_2$CCl=CHCl |
| CH$_2$CH$_3$ | CH$_3$ | CH$_2$CH=CCl$_2$ |
| CH$_2$CH$_3$ | CH$_3$ | CH=CHBr |
| CH$_2$CH$_3$ | CH$_3$ | CH=CBr$_2$ |
| CH$_2$CH$_3$ | CH$_3$ | CH=C(CH$_3$)Br |

TABLE 19

| R$^1$ | R$^2$ | R$^3$ |
|---|---|---|
| CH$_2$CH$_3$ | CH$_3$ | CH$_2$CH=CHBr |
| CH$_2$CH$_3$ | CH$_3$ | CH$_2$CBr=CHBr |
| CH$_2$CH$_3$ | CH$_3$ | CH$_2$CH=CBr$_2$ |
| CH$_2$CH$_3$ | CH$_3$ | CH$_2$CH=C(CH$_3$)Cl |
| CH$_2$CH$_3$ | CH$_3$ | CH$_2$CH=C(CF$_3$)Cl |
| CH$_2$CH$_3$ | CH$_3$ | CH$_2$CH=C(CH$_3$)Br |
| CH$_2$CH$_3$ | CH$_3$ | CH$_2$CH=C(CF$_3$)Br |
| CH$_2$CH$_3$ | CH$_3$ | CH=CHCF$_3$ |
| CH$_2$CH$_3$ | CH$_3$ | CH=CHCH$_2$CF$_3$ |
| CH$_2$CH$_3$ | CH$_3$ | CH$_2$CH=CHCH$_2$CF$_3$ |
| CH$_2$CH$_3$ | CH$_3$ | C≡CH |
| CH$_2$CH$_3$ | CH$_3$ | C≡CCH$_3$ |
| CH$_2$CH$_3$ | CH$_3$ | CH$_2$C≡CH |
| CH$_2$CH$_3$ | CH$_3$ | C≡CCH$_2$CH$_3$ |
| CH$_2$CH$_3$ | CH$_3$ | CH$_2$C≡CCH$_3$ |
| CH$_2$CH$_3$ | CH$_3$ | CH$_2$CH$_2$C≡CH |
| CH$_2$CH$_3$ | CH$_3$ | CH(CH$_3$)C≡CH |
| CH$_2$CH$_3$ | CH$_3$ | C≡CCH$_2$CH$_2$CH$_3$ |
| CH$_2$CH$_3$ | CH$_3$ | CH$_2$C≡CCH$_2$CH$_3$ |
| CH$_2$CH$_3$ | CH$_3$ | CH$_2$CH$_2$C≡CCH$_3$ |
| CH$_2$CH$_3$ | CH$_3$ | CH$_2$CH$_2$CH$_2$C≡CH |
| CH$_2$CH$_3$ | CH$_3$ | CH$_2$CH$_2$CH$_2$C≡CCH$_3$ |
| CH$_2$CH$_3$ | CH$_3$ | C≡CCl |
| CH$_2$CH$_3$ | CH$_3$ | CH$_2$C≡CCl |
| CH$_2$CH$_3$ | CH$_3$ | CH$_2$CH$_2$C≡CCl |
| CH$_2$CH$_3$ | CH$_3$ | CH$_2$CH$_2$CH$_2$C≡CCl |
| CH$_2$CH$_3$ | CH$_3$ | C≡CBr |
| CH$_2$CH$_3$ | CH$_3$ | CH$_2$C≡CBr |
| CH$_2$CH$_3$ | CH$_3$ | CH$_2$CH$_2$C≡CBr |
| CH$_2$CH$_3$ | CH$_3$ | CH$_2$CH$_2$CH$_2$C≡CBr |
| CH$_2$CH$_3$ | CH$_3$ | CH$_2$CH$_2$CH$_2$CH$_2$C≡CCl |
| CH$_2$CH$_3$ | CH$_3$ | CH$_2$OH |
| CH$_2$CH$_3$ | CH$_3$ | CH$_2$CH$_2$OH |
| CH$_2$CH$_3$ | CH$_3$ | CH$_2$CH$_2$CH$_2$OH |
| CH$_2$CH$_3$ | CH$_3$ | CH$_2$CH$_2$CH$_2$CH$_2$OH |

TABLE 20

| R$^1$ | R$^2$ | R$^3$ |
|---|---|---|
| CH$_2$CH$_3$ | CH$_3$ | CH$_2$CH$_2$CH$_2$CH$_2$CH$_2$OH |
| CH$_2$CH$_3$ | CH$_3$ | CH$_2$OCH$_3$ |
| CH$_2$CH$_3$ | CH$_3$ | CH$_2$OCH$_2$CH$_3$ |
| CH$_2$CH$_3$ | CH$_3$ | CH$_2$OCH$_2$CH$_2$CH$_3$ |
| CH$_2$CH$_3$ | CH$_3$ | CH$_2$OCH(CH$_3$)$_2$ |
| CH$_2$CH$_3$ | CH$_3$ | CH$_2$OCH$_2$CH$_2$CH$_2$CH$_3$ |
| CH$_2$CH$_3$ | CH$_3$ | CH$_2$OCH$_2$CH$_2$CH$_2$CH$_2$CH$_3$ |
| CH$_2$CH$_3$ | CH$_3$ | CH$_2$CH$_2$OCH$_3$ |
| CH$_2$CH$_3$ | CH$_3$ | CH$_2$CH$_2$OCH$_2$CH$_3$ |
| CH$_2$CH$_3$ | CH$_3$ | CH$_2$CH$_2$OCH$_2$CH$_2$CH$_3$ |
| CH$_2$CH$_3$ | CH$_3$ | CH$_2$CH$_2$OCH(CH$_3$)$_2$ |
| CH$_2$CH$_3$ | CH$_3$ | CH$_2$CH$_2$CH$_2$OCH$_3$ |
| CH$_2$CH$_3$ | CH$_3$ | C(=O)OCH$_3$ |
| CH$_2$CH$_3$ | CH$_3$ | C(=O)OCH$_2$CH$_3$ |
| CH$_2$CH$_3$ | CH$_3$ | C(=O)OCH$_2$CH$_2$CH$_3$ |

TABLE 20-continued

| R$^1$ | R$^2$ | R$^3$ |
|---|---|---|
| CH$_2$CH$_3$ | CH$_3$ | C(=O)OCH(CH$_3$)$_2$ |
| CH$_2$CH$_3$ | CH$_3$ | C(=O)OCH$_2$CH$_2$CH$_2$CH$_3$ |
| CH$_2$CH$_3$ | CH$_3$ | C(=O)OCH$_2$CH=CH$_2$ |
| CH$_2$CH$_3$ | CH$_3$ | C(=O)OCH(CH$_3$)CH=CH$_2$ |
| CH$_2$CH$_3$ | CH$_3$ | C(=O)OCH(CH$_3$)C(CH$_3$)=CH$_2$ |
| CH$_2$CH$_3$ | CH$_3$ | C(=O)OCH$_2$CH=CHCH$_3$ |
| CH$_2$CH$_3$ | CH$_3$ | C(=O)OCH(CH$_3$)CH=CHCH$_3$ |
| CH$_2$CH$_3$ | CH$_3$ | C(=O)OCH$_2$CH=C(CH$_3$)$_2$ |
| CH$_2$CH$_3$ | CH$_3$ | C(=O)OCH$_2$CH=CHCl |
| CH$_2$CH$_3$ | CH$_3$ | C(=O)OCH$_2$CH=CCl$_2$ |
| CH$_2$CH$_3$ | CH$_3$ | C(=O)OCH$_2$CH=CCl(CH$_3$) |
| CH$_2$CH$_3$ | CH$_3$ | C(=O)OCH$_2$CH=CHBr |
| CH$_2$CH$_3$ | CH$_3$ | C(=O)OCH$_2$CH=CBr$_2$ |
| CH$_2$CH$_3$ | CH$_3$ | C(=O)OCH$_2$CH=CBr(CH$_3$) |

TABLE 21

| R$^1$ | R$^2$ | R$^3$ |
|---|---|---|
| CH$_2$CH$_3$ | CH$_2$CH$_3$ | H |
| CH$_2$CH$_3$ | CH$_2$CH$_3$ | CH$_3$ |
| CH$_2$CH$_3$ | CH$_2$CH$_3$ | CH$_2$CH$_3$ |
| CH$_2$CH$_3$ | CH$_2$CH$_3$ | CH$_2$CH$_2$CH$_3$ |
| CH$_2$CH$_3$ | CH$_2$CH$_3$ | CH(CH$_3$)$_2$ |
| CH$_2$CH$_3$ | CH$_2$CH$_3$ | CH$_2$CH$_2$CH$_2$CH$_3$ |
| CH$_2$CH$_3$ | CH$_2$CH$_3$ | CH(CH$_3$)CH$_2$CH$_3$ |
| CH$_2$CH$_3$ | CH$_2$CH$_3$ | CH$_2$CH(CH$_3$)$_2$ |
| CH$_2$CH$_3$ | CH$_2$CH$_3$ | CH$_2$CH$_2$CH$_2$CH$_2$CH$_3$ |
| CH$_2$CH$_3$ | CH$_2$CH$_3$ | CH$_2$CH$_2$CH(CH$_3$)$_2$ |
| CH$_2$CH$_3$ | CH$_2$CH$_3$ | CH(CH$_3$)CH$_2$CH$_2$CH$_3$ |
| CH$_2$CH$_3$ | CH$_2$CH$_3$ | CH$_2$CH(CH$_3$)CH$_2$CH$_3$ |
| CH$_2$CH$_3$ | CH$_2$CH$_3$ | CH(CH$_3$)CH(CH$_3$)$_2$ |
| CH$_2$CH$_3$ | CH$_2$CH$_3$ | CH$_2$CH$_2$CH$_2$CH$_2$CH$_2$CH$_3$ |
| CH$_2$CH$_3$ | CH$_2$CH$_3$ | CH$_2$F |
| CH$_2$CH$_3$ | CH$_2$CH$_3$ | CF$_3$ |
| CH$_2$CH$_3$ | CH$_2$CH$_3$ | CH$_2$CH$_2$F |
| CH$_2$CH$_3$ | CH$_2$CH$_3$ | CH$_2$CF$_3$ |
| CH$_2$CH$_3$ | CH$_2$CH$_3$ | CH$_2$CH$_2$CH$_2$F |
| CH$_2$CH$_3$ | CH$_2$CH$_3$ | CH$_2$CH$_2$CF$_3$ |
| CH$_2$CH$_3$ | CH$_2$CH$_3$ | CH$_2$CH$_2$CH$_2$CF$_3$ |
| CH$_2$CH$_3$ | CH$_2$CH$_3$ | CH$_2$CH$_2$CH$_2$CH$_2$CF$_3$ |
| CH$_2$CH$_3$ | CH$_2$CH$_3$ | CH$_2$CH$_2$Cl |
| CH$_2$CH$_3$ | CH$_2$CH$_3$ | CHClCH$_2$Cl |
| CH$_2$CH$_3$ | CH$_2$CH$_3$ | CH$_2$CH$_2$Br |
| CH$_2$CH$_3$ | CH$_2$CH$_3$ | CHBrCH$_2$Br |
| CH$_2$CH$_3$ | CH$_2$CH$_3$ | CH$_2$CH$_2$CH$_2$Cl |
| CH$_2$CH$_3$ | CH$_2$CH$_3$ | CH$_2$CHClCH$_2$Cl |
| CH$_2$CH$_3$ | CH$_2$CH$_3$ | CH$_2$CH$_2$CH$_2$Br |
| CH$_2$CH$_3$ | CH$_2$CH$_3$ | CH$_2$CHBrCH$_2$Br |
| CH$_2$CH$_3$ | CH$_2$CH$_3$ | CH$_2$CH$_2$CH$_2$CH$_2$Cl |
| CH$_2$CH$_3$ | CH$_2$CH$_3$ | CH$_2$CH$_2$CH$_2$CH$_2$Br |
| CH$_2$CH$_3$ | CH$_2$CH$_3$ | CH$_2$CH$_2$CH$_2$CH$_2$CH$_2$Cl |
| CH$_2$CH$_3$ | CH$_2$CH$_3$ | CH$_2$CH$_2$CH$_2$CH$_2$CH$_2$Br |

TABLE 22

| R$^1$ | R$^2$ | R$^3$ |
|---|---|---|
| CH$_2$CH$_3$ | CH$_2$CH$_3$ | CH$_2$CH$_2$CH$_2$CH$_2$CH$_2$Cl |
| CH$_2$CH$_3$ | CH$_2$CH$_3$ | CH$_2$CH$_2$CH$_2$CH$_2$CH$_2$Br |
| CH$_2$CH$_3$ | CH$_2$CH$_3$ | CH=CH$_2$ |
| CH$_2$CH$_3$ | CH$_2$CH$_3$ | CH$_2$CH=CH$_2$ |
| CH$_2$CH$_3$ | CH$_2$CH$_3$ | CH=CHCH$_3$ |
| CH$_2$CH$_3$ | CH$_2$CH$_3$ | C(CH$_3$)=CH$_2$ |
| CH$_2$CH$_3$ | CH$_2$CH$_3$ | CH=CHCH$_2$CH$_3$ |
| CH$_2$CH$_3$ | CH$_2$CH$_3$ | CH$_2$CH=CHCH$_3$ |
| CH$_2$CH$_3$ | CH$_2$CH$_3$ | CH$_2$CH$_2$CH=CH$_2$ |
| CH$_2$CH$_3$ | CH$_2$CH$_3$ | C(CH$_3$)=CHCH$_3$ |
| CH$_2$CH$_3$ | CH$_2$CH$_3$ | CH(CH$_3$)CH=CH$_2$ |
| CH$_2$CH$_3$ | CH$_2$CH$_3$ | CH=C(CH$_3$)$_2$ |
| CH$_2$CH$_3$ | CH$_2$CH$_3$ | CH$_2$C(CH$_3$)=CH$_2$ |

TABLE 22-continued

| R¹ | R² | R³ |
|---|---|---|
| CH₂CH₃ | CH₂CH₃ | C(CH₂CH₃)=CH₂ |
| CH₂CH₃ | CH₂CH₃ | CH=CHCH₂CH₂CH₃ |
| CH₂CH₃ | CH₂CH₃ | C(CH₃)=CHCH₂CH₃ |
| CH₂CH₃ | CH₂CH₃ | CH(CH₃)CH=CHCH₃ |
| CH₂CH₃ | CH₂CH₃ | CH(CH₃)CH₂CH=CH₂ |
| CH₂CH₃ | CH₂CH₃ | CH=C(CH₃)CH₂CH₃ |
| CH₂CH₃ | CH₂CH₃ | CH₂C(CH₃)=CHCH₃ |
| CH₂CH₃ | CH₂CH₃ | CH₂CH(CH₃)CH=CH₂ |
| CH₂CH₃ | CH₂CH₃ | CH=CHCH(CH₃)₂ |
| CH₂CH₃ | CH₂CH₃ | CH₂CH=C(CH₃)₂ |
| CH₂CH₃ | CH₂CH₃ | CH₂CH₂C(CH₂)=CH₂ |
| CH₂CH₃ | CH₂CH₃ | CH₂CH=C(CH₃)₂ |
| CH₂CH₃ | CH₂CH₃ | CH=CHCH₂CH₂CH₂CH₃ |
| CH₂CH₃ | CH₂CH₃ | CH=CHCl |
| CH₂CH₃ | CH₂CH₃ | CH=CCl₂ |
| CH₂CH₃ | CH₂CH₃ | CH=C(CH₃)Cl |
| CH₂CH₃ | CH₂CH₃ | CH₂CH=CHCl |
| CH₂CH₃ | CH₂CH₃ | CH₂CCl=CHCl |
| CH₂CH₃ | CH₂CH₃ | CH₂CH=CCl₂ |
| CH₂CH₃ | CH₂CH₃ | CH=CHBr |
| CH₂CH₃ | CH₂CH₃ | CH=CBr₂ |
| CH₂CH₃ | CH₂CH₃ | CH=C(CH₃)Br |

TABLE 23

| R¹ | R² | R³ |
|---|---|---|
| CH₂CH₃ | CH₂CH₃ | CH₂CH=CHBr |
| CH₂CH₃ | CH₂CH₃ | CH₂CBr=CHBr |
| CH₂CH₃ | CH₂CH₃ | CH₂CH=CBr₂ |
| CH₂CH₃ | CH₂CH₃ | CH₂CH=C(CH₃)Cl |
| CH₂CH₃ | CH₂CH₃ | CH₂CH=C(CF₃)Cl |
| CH₂CH₃ | CH₂CH₃ | CH₂CH=C(CH₃)Br |
| CH₂CH₃ | CH₂CH₃ | CH₂CH=C(CF₃)Br |
| CH₂CH₃ | CH₂CH₃ | CH=CHCF₃ |
| CH₂CH₃ | CH₂CH₃ | CH=CHCH₂CF₃ |
| CH₂CH₃ | CH₂CH₃ | CH₂CH=CHCH₂CF₃ |
| CH₂CH₃ | CH₂CH₃ | C≡CH |
| CH₂CH₃ | CH₂CH₃ | C≡CCH₃ |
| CH₂CH₃ | CH₂CH₃ | CH₂C≡CH |
| CH₂CH₃ | CH₂CH₃ | C≡CCH₂CH₃ |
| CH₂CH₃ | CH₂CH₃ | CH₂C≡CCH₃ |
| CH₂CH₃ | CH₂CH₃ | CH₂CH₂C≡CH |
| CH₂CH₃ | CH₂CH₃ | CH(CH₃)C≡CH |
| CH₂CH₃ | CH₂CH₃ | C≡CCH₂CH₂CH₃ |
| CH₂CH₃ | CH₂CH₃ | CH₂C≡CCH₂CH₃ |
| CH₂CH₃ | CH₂CH₃ | CH₂CH₂C≡CCH₃ |
| CH₂CH₃ | CH₂CH₃ | CH₂CH₂CH₂C≡CH |
| CH₂CH₃ | CH₂CH₃ | CH₂CH₂CH₂C≡CCH₃ |
| CH₂CH₃ | CH₂CH₃ | C≡CCl |
| CH₂CH₃ | CH₂CH₃ | CH₂C≡CCl |
| CH₂CH₃ | CH₂CH₃ | CH₂CH₂C≡CCl |
| CH₂CH₃ | CH₂CH₃ | CH₂CH₂CH₂C≡CCl |
| CH₂CH₃ | CH₂CH₃ | C≡CBr |
| CH₂CH₃ | CH₂CH₃ | CH₂C≡CBr |
| CH₂CH₃ | CH₂CH₃ | CH₂CH₂C≡CBr |
| CH₂CH₃ | CH₂CH₃ | CH₂CH₂CH₂C≡CBr |
| CH₂CH₃ | CH₂CH₃ | CH₂CH₂CH₂CH₂C≡CCl |
| CH₂CH₃ | CH₂CH₃ | CH₂OH |
| CH₂CH₃ | CH₂CH₃ | CH₂CH₂OH |
| CH₂CH₃ | CH₂CH₃ | CH₂CH₂CH₂OH |
| CH₂CH₃ | CH₂CH₃ | CH₂CH₂CH₂CH₂OH |

TABLE 24

| R¹ | R² | R³ |
|---|---|---|
| CH₂CH₃ | CH₂CH₃ | CH₂CH₂CH₂CH₂CH₂OH |
| CH₂CH₃ | CH₂CH₃ | CH₂OCH₃ |
| CH₂CH₃ | CH₂CH₃ | CH₂OCH₂CH₃ |
| CH₂CH₃ | CH₂CH₃ | CH₂OCH₂CH₂CH₃ |
| CH₂CH₃ | CH₂CH₃ | CH₂OCH(CH₃)₂ |

TABLE 24-continued

| R¹ | R² | R³ |
|---|---|---|
| CH₂CH₃ | CH₂CH₃ | CH₂OCH₂CH₂CH₂CH₃ |
| CH₂CH₃ | CH₂CH₃ | CH₂OCH₂CH₂CH₂CH₂CH₃ |
| CH₂CH₃ | CH₂CH₃ | CH₂CH₂OCH₃ |
| CH₂CH₃ | CH₂CH₃ | CH₂CH₂OCH₂CH₃ |
| CH₂CH₃ | CH₂CH₃ | CH₂CH₂OCH₂CH₂CH₃ |
| CH₂CH₃ | CH₂CH₃ | CH₂CH₂OCH(CH₃)₂ |
| CH₂CH₃ | CH₂CH₃ | CH₂CH₂CH₂OCH₃ |
| CH₂CH₃ | CH₂CH₃ | C(=O)OCH₃ |
| CH₂CH₃ | CH₂CH₃ | C(=O)OCH₂CH₃ |
| CH₂CH₃ | CH₂CH₃ | C(=O)OCH₂CH₂CH₃ |
| CH₂CH₃ | CH₂CH₃ | C(=O)OCH(CH₃)₂ |
| CH₂CH₃ | CH₂CH₃ | C(=O)OCH₂CH₂CH₂CH₃ |
| CH₂CH₃ | CH₂CH₃ | C(=O)OCH₂CH=CH₂ |
| CH₂CH₃ | CH₂CH₃ | C(=O)OCH(CH₃)CH=CH₂ |
| CH₂CH₃ | CH₂CH₃ | C(=O)OCH(CH₃)C(CH₃)=CH₂ |
| CH₂CH₃ | CH₂CH₃ | C(=O)OCH₂CH=CHCH₃ |
| CH₂CH₃ | CH₂CH₃ | C(=O)OCH(CH₃)CH=CHCH₃ |
| CH₂CH₃ | CH₂CH₃ | C(=O)OCH₂CH=C(CH₃)₂ |
| CH₂CH₃ | CH₂CH₃ | C(=O)OCH₂CH=CHCl |
| CH₂CH₃ | CH₂CH₃ | C(=O)OCH₂CH=CCl₂ |
| CH₂CH₃ | CH₂CH₃ | C(=O)OCH₂CH=CCl(CH₃) |
| CH₂CH₃ | CH₂CH₃ | C(=O)OCH₂CH=CHBr |
| CH₂CH₃ | CH₂CH₃ | C(=O)OCH₂CH=CBr₂ |
| CH₂CH₃ | CH₂CH₃ | C(=O)OCH₂CH=CBr(CH₃) |

TABLE 25

| R¹ | R² | R³ |
|---|---|---|
| CH₂CH₃ | CH(CH₃)₂ | H |
| CH₂CH₃ | CH(CH₃)₂ | CH₃ |
| CH₂CH₃ | CH(CH₃)₂ | CH₂CH₃ |
| CH₂CH₃ | CH(CH₃)₂ | CH₂CH₂CH₃ |
| CH₂CH₃ | CH(CH₃)₂ | CH(CH₃)₂ |
| CH₂CH₃ | CH(CH₃)₂ | CH₂CH₂CH₂CH₃ |
| CH₂CH₃ | CH(CH₃)₂ | CH(CH₃)CH₂CH₃ |
| CH₂CH₃ | CH(CH₃)₂ | CH₂CH(CH₃)₂ |
| CH₂CH₃ | CH(CH₃)₂ | CH₂CH₂CH₂CH₂CH₃ |
| CH₂CH₃ | CH(CH₃)₂ | CH₂CH₂CH(CH₃)₂ |
| CH₂CH₃ | CH(CH₃)₂ | CH(CH₃)CH₂CH₂CH₃ |
| CH₂CH₃ | CH(CH₃)₂ | CH₂CH(CH₃)CH₂CH₃ |
| CH₂CH₃ | CH(CH₃)₂ | CH(CH₃)CH(CH₃)₂ |
| CH₂CH₃ | CH(CH₃)₂ | CH₂CH₂CH₂CH₂CH₂CH₃ |
| CH₂CH₃ | CH(CH₃)₂ | CH₂F |
| CH₂CH₃ | CH(CH₃)₂ | CF₃ |
| CH₂CH₃ | CH(CH₃)₂ | CH₂CH₂F |
| CH₂CH₃ | CH(CH₃)₂ | CH₂CF₃ |
| CH₂CH₃ | CH(CH₃)₂ | CH₂CH₂CH₂F |
| CH₂CH₃ | CH(CH₃)₂ | CH₂CH₂CF₃ |
| CH₂CH₃ | CH(CH₃)₂ | CH₂CH₂CH₂CH₂F |
| CH₂CH₃ | CH(CH₃)₂ | CH₂CH₂CH₂CF₃ |
| CH₂CH₃ | CH(CH₃)₂ | CH₂CH₂CH₂CH₂CF₃ |
| CH₂CH₃ | CH(CH₃)₂ | CH₂CH₂Cl |
| CH₂CH₃ | CH(CH₃)₂ | CHClCH₂Cl |
| CH₂CH₃ | CH(CH₃)₂ | CH₂CH₂Br |
| CH₂CH₃ | CH(CH₃)₂ | CHBrCH₂Br |
| CH₂CH₃ | CH(CH₃)₂ | CH₂CH₂CH₂Cl |
| CH₂CH₃ | CH(CH₃)₂ | CH₂CHClCH₂Cl |
| CH₂CH₃ | CH(CH₃)₂ | CH₂CH₂CH₂Br |
| CH₂CH₃ | CH(CH₃)₂ | CH₂CHBrCH₂Br |
| CH₂CH₃ | CH(CH₃)₂ | CH₂CH₂CH₂CH₂Cl |
| CH₂CH₃ | CH(CH₃)₂ | CH₂CH₂CH₂CH₂Br |
| CH₂CH₃ | CH(CH₃)₂ | CH₂CH₂CH₂CH₂CH₂Cl |
| CH₂CH₃ | CH(CH₃)₂ | CH₂CH₂CH₂CH₂CH₂Br |

TABLE 26

| R¹ | R² | R³ |
|---|---|---|
| CH₂CH₃ | CH(CH₃)₂ | CH₂CH₂CH₂CH₂CH₂CH₂Cl |
| CH₂CH₃ | CH(CH₃)₂ | CH₂CH₂CH₂CH₂CH₂CH₂Br |
| CH₂CH₃ | CH(CH₃)₂ | CH=CH₂ |

TABLE 26-continued

| R¹ | R² | R³ |
|---|---|---|
| CH₂CH₃ | CH(CH₃)₂ | CH₂CH=CH₂ |
| CH₂CH₃ | CH(CH₃)₂ | CH=CHCH₃ |
| CH₂CH₃ | CH(CH₃)₂ | C(CH₃)=CH₂ |
| CH₂CH₃ | CH(CH₃)₂ | CH=CHCH₂CH₃ |
| CH₂CH₃ | CH(CH₃)₂ | CH₂CH=CHCH₃ |
| CH₂CH₃ | CH(CH₃)₂ | CH₂CH₂CH=CH₂ |
| CH₂CH₃ | CH(CH₃)₂ | C(CH₃)=CHCH₃ |
| CH₂CH₃ | CH(CH₃)₂ | CH(CH₃)CH=CH₂ |
| CH₂CH₃ | CH(CH₃)₂ | CH=C(CH₃)₂ |
| CH₂CH₃ | CH(CH₃)₂ | CH₂C(CH₃)=CH₂ |
| CH₂CH₃ | CH(CH₃)₂ | C(CH₂CH₃)=CH₂ |
| CH₂CH₃ | CH(CH₃)₂ | CH=CHCH₂CH₂CH₃ |
| CH₂CH₃ | CH(CH₃)₂ | C(CH₃)=CHCH₂CH₃ |
| CH₂CH₃ | CH(CH₃)₂ | CH(CH₃)CH=CHCH₃ |
| CH₂CH₃ | CH(CH₃)₂ | CH(CH₃)CH₂CH=CH₂ |
| CH₂CH₃ | CH(CH₃)₂ | CH=C(CH₃)CH₂CH₃ |
| CH₂CH₃ | CH(CH₃)₂ | CH₂C(CH₃)=CHCH₃ |
| CH₂CH₃ | CH(CH₃)₂ | CH₂CH(CH₃)CH=CH₂ |
| CH₂CH₃ | CH(CH₃)₂ | CH=CHCH(CH₃)₂ |
| CH₂CH₃ | CH(CH₃)₂ | CH₂CH=C(CH₃)₂ |
| CH₂CH₃ | CH(CH₃)₂ | CH₂CH₂C(CH₂)=CH₂ |
| CH₂CH₃ | CH(CH₃)₂ | CH₂CH=C(CH₃)₂ |
| CH₂CH₃ | CH(CH₃)₂ | CH=CHCH₂CH₂CH₃ |
| CH₂CH₃ | CH(CH₃)₂ | CH=CHCl |
| CH₂CH₃ | CH(CH₃)₂ | CH=CCl₂ |
| CH₂CH₃ | CH(CH₃)₂ | CH=C(CH₃)Cl |
| CH₂CH₃ | CH(CH₃)₂ | CH₂CH=CHCl |
| CH₂CH₃ | CH(CH₃)₂ | CH₂CCl=CHCl |
| CH₂CH₃ | CH(CH₃)₂ | CH₂CH=CCl₂ |
| CH₂CH₃ | CH(CH₃)₂ | CH=CHBr |
| CH₂CH₃ | CH(CH₃)₂ | CH=CBr₂ |
| CH₂CH₃ | CH(CH₃)₂ | CH=C(CH₃)Br |

TABLE 27

| R¹ | R² | R³ |
|---|---|---|
| CH₂CH₃ | CH(CH₃)₂ | CH₂CH=CHBr |
| CH₂CH₃ | CH(CH₃)₂ | CH₂CBr=CHBr |
| CH₂CH₃ | CH(CH₃)₂ | CH₂CH=CBr₂ |
| CH₂CH₃ | CH(CH₃)₂ | CH₂CH=C(CH₃)Cl |
| CH₂CH₃ | CH(CH₃)₂ | CH₂CH=C(CF₃)Cl |
| CH₂CH₃ | CH(CH₃)₂ | CH₂CH=C(CH₃)Br |
| CH₂CH₃ | CH(CH₃)₂ | CH₂CH=C(CF₃)Br |
| CH₂CH₃ | CH(CH₃)₂ | CH=CHCF₃ |
| CH₂CH₃ | CH(CH₃)₂ | CH=CHCH₂CF₃ |
| CH₂CH₃ | CH(CH₃)₂ | CH₂CH=CHCH₂CF₃ |
| CH₂CH₃ | CH(CH₃)₂ | C≡CH |
| CH₂CH₃ | CH(CH₃)₂ | C≡CCH₃ |
| CH₂CH₃ | CH(CH₃)₂ | CH₂C≡CH |
| CH₂CH₃ | CH(CH₃)₂ | C≡CCH₂CH₃ |
| CH₂CH₃ | CH(CH₃)₂ | CH₂C≡CCH₃ |
| CH₂CH₃ | CH(CH₃)₂ | CH₂CH₂C≡CH |
| CH₂CH₃ | CH(CH₃)₂ | CH(CH₃)C≡CH |
| CH₂CH₃ | CH(CH₃)₂ | C≡CCH₂CH₂CH₃ |
| CH₂CH₃ | CH(CH₃)₂ | CH₂C≡CCH₂CH₃ |
| CH₂CH₃ | CH(CH₃)₂ | CH₂CH₂C≡CCH₃ |
| CH₂CH₃ | CH(CH₃)₂ | CH₂CH₂CH₂C≡CH |
| CH₂CH₃ | CH(CH₃)₂ | CH₂CH₂CH₂C≡CCH₃ |
| CH₂CH₃ | CH(CH₃)₂ | C≡CCl |
| CH₂CH₃ | CH(CH₃)₂ | CH₂C≡CCl |
| CH₂CH₃ | CH(CH₃)₂ | CH₂CH₂C≡CCl |
| CH₂CH₃ | CH(CH₃)₂ | CH₂CH₂CH₂C≡CCl |
| CH₂CH₃ | CH(CH₃)₂ | C≡CBr |
| CH₂CH₃ | CH(CH₃)₂ | CH₂C≡CBr |
| CH₂CH₃ | CH(CH₃)₂ | CH₂CH₂C≡CBr |
| CH₂CH₃ | CH(CH₃)₂ | CH₂CH₂CH₂C≡CBr |
| CH₂CH₃ | CH(CH₃)₂ | CH₂CH₂CH₂CH₂C≡CCl |
| CH₂CH₃ | CH(CH₃)₂ | CH₂OH |
| CH₂CH₃ | CH(CH₃)₂ | CH₂CH₂OH |
| CH₂CH₃ | CH(CH₃)₂ | CH₂CH₂CH₂OH |
| CH₂CH₃ | CH(CH₃)₂ | CH₂CH₂CH₂CH₂OH |

TABLE 28

| R¹ | R² | R³ |
|---|---|---|
| CH₂CH₃ | CH(CH₃)₂ | CH₂CH₂CH₂CH₂CH₂OH |
| CH₂CH₃ | CH(CH₃)₂ | CH₂OCH₃ |
| CH₂CH₃ | CH(CH₃)₂ | CH₂OCH₂CH₃ |
| CH₂CH₃ | CH(CH₃)₂ | CH₂OCH₂CH₂CH₃ |
| CH₂CH₃ | CH(CH₃)₂ | CH₂OCH(CH₃)₂ |
| CH₂CH₃ | CH(CH₃)₂ | CH₂OCH₂CH₂CH₂CH₃ |
| CH₂CH₃ | CH(CH₃)₂ | CH₂OCH₂CH₂CH₂CH₂CH₃ |
| CH₂CH₃ | CH(CH₃)₂ | CH₂CH₂OCH₃ |
| CH₂CH₃ | CH(CH₃)₂ | CH₂CH₂OCH₂CH₃ |
| CH₂CH₃ | CH(CH₃)₂ | CH₂CH₂OCH₂CH₂CH₃ |
| CH₂CH₃ | CH(CH₃)₂ | CH₂CH₂OCH(CH₃)₂ |
| CH₂CH₃ | CH(CH₃)₂ | CH₂CH₂CH₂OCH₃ |
| CH₂CH₃ | CH(CH₃)₂ | C(=O)OCH₃ |
| CH₂CH₃ | CH(CH₃)₂ | C(=O)OCH₂CH₃ |
| CH₂CH₃ | CH(CH₃)₂ | C(=O)OCH₂CH₂CH₃ |
| CH₂CH₃ | CH(CH₃)₂ | C(=O)OCH(CH₃)₂ |
| CH₂CH₃ | CH(CH₃)₂ | C(=O)OCH₂CH₂CH₂CH₃ |
| CH₂CH₃ | CH(CH₃)₂ | C(=O)OCH₂CH=CH₂ |
| CH₂CH₃ | CH(CH₃)₂ | C(=O)OCH(CH₃)CH=CH₂ |
| CH₂CH₃ | CH(CH₃)₂ | C(=O)OCH(CH₃)C(CH₃)=CH₂ |
| CH₂CH₃ | CH(CH₃)₂ | C(=O)OCH₂CH=CHCH₃ |
| CH₂CH₃ | CH(CH₃)₂ | C(=O)OCH(CH₃)CH=CHCH₃ |
| CH₂CH₃ | CH(CH₃)₂ | C(=O)OCH₂CH=C(CH₃)₂ |
| CH₂CH₃ | CH(CH₃)₂ | C(=O)OCH₂CH=CHCl |
| CH₂CH₃ | CH(CH₃)₂ | C(=O)OCH₂CH=CCl₂ |
| CH₂CH₃ | CH(CH₃)₂ | C(=O)OCH₂CH=CCl(CH₃) |
| CH₂CH₃ | CH(CH₃)₂ | C(=O)OCH₂CH=CHBr |
| CH₂CH₃ | CH(CH₃)₂ | C(=O)OCH₂CH=CBr₂ |
| CH₂CH₃ | CH(CH₃)₂ | C(=O)OCH₂CH=CBr(CH₃) |

TABLE 29

| R¹ | R² | R³ |
|---|---|---|
| CH₂CH₃ | C(CH₃)₃ | H |
| CH₂CH₃ | C(CH₃)₃ | CH₃ |
| CH₂CH₃ | C(CH₃)₃ | CH₂CH₃ |
| CH₂CH₃ | C(CH₃)₃ | CH₂CH₂CH₃ |
| CH₂CH₃ | C(CH₃)₃ | CH(CH₃)₂ |
| CH₂CH₃ | C(CH₃)₃ | CH₂CH₂CH₂CH₃ |
| CH₂CH₃ | C(CH₃)₃ | CH(CH₃)CH₂CH₃ |
| CH₂CH₃ | C(CH₃)₃ | CH₂CH(CH₃)₂ |
| CH₂CH₃ | C(CH₃)₃ | CH₂CH₂CH₂CH₂CH₃ |
| CH₂CH₃ | C(CH₃)₃ | CH₂CH₂CH(CH₃)₂ |
| CH₂CH₃ | C(CH₃)₃ | CH(CH₃)CH₂CH₂CH₃ |
| CH₂CH₃ | C(CH₃)₃ | CH₂CH(CH₃)CH₂CH₃ |
| CH₂CH₃ | C(CH₃)₃ | CH(CH₃)CH(CH₃)₂ |
| CH₂CH₃ | C(CH₃)₃ | CH₂CH₂CH₂CH₂CH₂CH₃ |
| CH₂CH₃ | C(CH₃)₃ | CH₂F |
| CH₂CH₃ | C(CH₃)₃ | CF₃ |
| CH₂CH₃ | C(CH₃)₃ | CH₂CH₂F |
| CH₂CH₃ | C(CH₃)₃ | CH₂CF₃ |
| CH₂CH₃ | C(CH₃)₃ | CH₂CH₂CH₂F |
| CH₂CH₃ | C(CH₃)₃ | CH₂CH₂CF₃ |
| CH₂CH₃ | C(CH₃)₃ | CH₂CH₂CH₂CH₂F |
| CH₂CH₃ | C(CH₃)₃ | CH₂CH₂CH₂CF₃ |
| CH₂CH₃ | C(CH₃)₃ | CH₂CH₂CH₂CH₂CF₃ |
| CH₂CH₃ | C(CH₃)₃ | CH₂CH₂Cl |
| CH₂CH₃ | C(CH₃)₃ | CHClCH₂Cl |
| CH₂CH₃ | C(CH₃)₃ | CH₂CH₂Br |
| CH₂CH₃ | C(CH₃)₃ | CHBrCH₂Br |
| CH₂CH₃ | C(CH₃)₃ | CH₂CH₂CH₂Cl |
| CH₂CH₃ | C(CH₃)₃ | CH₂CHClCH₂Cl |
| CH₂CH₃ | C(CH₃)₃ | CH₂CH₂CH₂Br |
| CH₂CH₃ | C(CH₃)₃ | CH₂CHBrCH₂Br |
| CH₂CH₃ | C(CH₃)₃ | CH₂CH₂CH₂CH₂Cl |
| CH₂CH₃ | C(CH₃)₃ | CH₂CH₂CH₂CH₂Br |
| CH₂CH₃ | C(CH₃)₃ | CH₂CH₂CH₂CH₂CH₂Cl |
| CH₂CH₃ | C(CH₃)₃ | CH₂CH₂CH₂CH₂CH₂Br |

TABLE 30

| R¹ | R² | R³ |
|---|---|---|
| CH₂CH₃ | C(CH₃)₃ | CH₂CH₂CH₂CH₂CH₂CH₂Cl |
| CH₂CH₃ | C(CH₃)₃ | CH₂CH₂CH₂CH₂CH₂CH₂Br |
| CH₂CH₃ | C(CH₃)₃ | CH=CH₂ |
| CH₂CH₃ | C(CH₃)₃ | CH₂CH=CH₂ |
| CH₂CH₃ | C(CH₃)₃ | CH=CHCH₃ |
| CH₂CH₃ | C(CH₃)₃ | C(CH₃)=CH₂ |
| CH₂CH₃ | C(CH₃)₃ | CH=CHCH₂CH₃ |
| CH₂CH₃ | C(CH₃)₃ | CH₂CH=CHCH₃ |
| CH₂CH₃ | C(CH₃)₃ | CH₂CH₂CH=CH₂ |
| CH₂CH₃ | C(CH₃)₃ | C(CH₃)=CHCH₃ |
| CH₂CH₃ | C(CH₃)₃ | CH(CH₃)CH=CH₂ |
| CH₂CH₃ | C(CH₃)₃ | CH=C(CH₃)₂ |
| CH₂CH₃ | C(CH₃)₃ | CH₂C(CH₃)=CH₂ |
| CH₂CH₃ | C(CH₃)₃ | C(CH₂CH₃)=CH₂ |
| CH₂CH₃ | C(CH₃)₃ | CH=CHCH₂CH₂CH₃ |
| CH₂CH₃ | C(CH₃)₃ | C(CH₃)=CHCH₂CH₃ |
| CH₂CH₃ | C(CH₃)₃ | CH(CH₃)CH=CHCH₃ |
| CH₂CH₃ | C(CH₃)₃ | CH(CH₃)CH₂CH=CH₂ |
| CH₂CH₃ | C(CH₃)₃ | CH=C(CH₃)CH₂CH₃ |
| CH₂CH₃ | C(CH₃)₃ | CH₂C(CH₃)=CHCH₃ |
| CH₂CH₃ | C(CH₃)₃ | CH₂CH(CH₃)CH=CH₂ |
| CH₂CH₃ | C(CH₃)₃ | CH=CHCH(CH₃)₂ |
| CH₂CH₃ | C(CH₃)₃ | CH₂CH=C(CH₃)₂ |
| CH₂CH₃ | C(CH₃)₃ | CH₂CH₂C(CH₂)=CH₂ |
| CH₂CH₃ | C(CH₃)₃ | CH₂CH=C(CH₃)₂ |
| CH₂CH₃ | C(CH₃)₃ | CH=CHCH₂CH₂CH₂CH₃ |
| CH₂CH₃ | C(CH₃)₃ | CH=CHCl |
| CH₂CH₃ | C(CH₃)₃ | CH=CCl₂ |
| CH₂CH₃ | C(CH₃)₃ | CH=C(CH₃)Cl |
| CH₂CH₃ | C(CH₃)₃ | CH₂CH=CHCl |
| CH₂CH₃ | C(CH₃)₃ | CH₂CCl=CHCl |
| CH₂CH₃ | C(CH₃)₃ | CH₂CH=CCl₂ |
| CH₂CH₃ | C(CH₃)₃ | CH=CHBr |
| CH₂CH₃ | C(CH₃)₃ | CH=CBr₂ |
| CH₂CH₃ | C(CH₃)₃ | CH=C(CH₃)Br |

TABLE 31

| R¹ | R² | R³ |
|---|---|---|
| CH₂CH₃ | C(CH₃)₃ | CH₂CH=CHBr |
| CH₂CH₃ | C(CH₃)₃ | CH₂CBr=CHBr |
| CH₂CH₃ | C(CH₃)₃ | CH₂CH=CBr₂ |
| CH₂CH₃ | C(CH₃)₃ | CH₂CH=C(CH₃)Cl |
| CH₂CH₃ | C(CH₃)₃ | CH₂CH=C(CF₃)Cl |
| CH₂CH₃ | C(CH₃)₃ | CH₂CH=C(CH₃)Br |
| CH₂CH₃ | C(CH₃)₃ | CH₂CH=C(CF₃)Br |
| CH₂CH₃ | C(CH₃)₃ | CH=CHCF₃ |
| CH₂CH₃ | C(CH₃)₃ | CH=CHCH₂CF₃ |
| CH₂CH₃ | C(CH₃)₃ | CH₂CH=CHCH₂CF₃ |
| CH₂CH₃ | C(CH₃)₃ | C≡CH |
| CH₂CH₃ | C(CH₃)₃ | C≡CCH₃ |
| CH₂CH₃ | C(CH₃)₃ | CH₂C≡CH |
| CH₂CH₃ | C(CH₃)₃ | C≡CCH₂CH₃ |
| CH₂CH₃ | C(CH₃)₃ | CH₂C≡CCH₃ |
| CH₂CH₃ | C(CH₃)₃ | CH₂CH₂C≡CH |
| CH₂CH₃ | C(CH₃)₃ | CH(CH₃)C≡CH |
| CH₂CH₃ | C(CH₃)₃ | C≡CCH₂CH₂CH₃ |
| CH₂CH₃ | C(CH₃)₃ | CH₂C≡CCH₂CH₃ |
| CH₂CH₃ | C(CH₃)₃ | CH₂CH₂C≡CCH₃ |
| CH₂CH₃ | C(CH₃)₃ | CH₂CH₂CH₂C≡CH |
| CH₂CH₃ | C(CH₃)₃ | CH₂CH₂CH₂C≡CCH₃ |
| CH₂CH₃ | C(CH₃)₃ | C≡CCl |
| CH₂CH₃ | C(CH₃)₃ | CH₂C≡CCl |
| CH₂CH₃ | C(CH₃)₃ | CH₂CH₂C≡CCl |
| CH₂CH₃ | C(CH₃)₃ | C≡CBr |
| CH₂CH₃ | C(CH₃)₃ | CH₂C≡CBr |
| CH₂CH₃ | C(CH₃)₃ | CH₂CH₂C≡CBr |
| CH₂CH₃ | C(CH₃)₃ | CH₂CH₂CH₂CH₂C≡CCl |
| CH₂CH₃ | C(CH₃)₃ | CH₂OH |
| CH₂CH₃ | C(CH₃)₃ | CH₂CH₂OH |

TABLE 31-continued

| R¹ | R² | R³ |
|---|---|---|
| CH₂CH₃ | C(CH₃)₃ | CH₂CH₂CH₂OH |
| CH₂CH₃ | C(CH₃)₃ | CH₂CH₂CH₂CH₂OH |

TABLE 32

| R¹ | R² | R³ |
|---|---|---|
| CH₂CH₃ | C(CH₃)₃ | CH₂CH₂CH₂CH₂CH₂OH |
| CH₂CH₃ | C(CH₃)₃ | CH₂OCH₃ |
| CH₂CH₃ | C(CH₃)₃ | CH₂OCH₂CH₃ |
| CH₂CH₃ | C(CH₃)₃ | CH₂OCH₂CH₂CH₃ |
| CH₂CH₃ | C(CH₃)₃ | CH₂OCH(CH₃)₂ |
| CH₂CH₃ | C(CH₃)₃ | CH₂OCH₂CH₂CH₂CH₃ |
| CH₂CH₃ | C(CH₃)₃ | CH₂OCH₂CH₂CH₂CH₂CH₃ |
| CH₂CH₃ | C(CH₃)₃ | CH₂CH₂OCH₃ |
| CH₂CH₃ | C(CH₃)₃ | CH₂CH₂OCH₂CH₃ |
| CH₂CH₃ | C(CH₃)₃ | CH₂CH₂OCH₂CH₂CH₃ |
| CH₂CH₃ | C(CH₃)₃ | CH₂CH₂OCH(CH₃)₂ |
| CH₂CH₃ | C(CH₃)₃ | CH₂CH₂CH₂OCH₃ |
| CH₂CH₃ | C(CH₃)₃ | C(=O)OCH₃ |
| CH₂CH₃ | C(CH₃)₃ | C(=O)OCH₂CH₃ |
| CH₂CH₃ | C(CH₃)₃ | C(=O)OCH₂CH₂CH₃ |
| CH₂CH₃ | C(CH₃)₃ | C(=O)OCH(CH₃)₂ |
| CH₂CH₃ | C(CH₃)₃ | C(=O)OCH₂CH₂CH₂CH₃ |
| CH₂CH₃ | C(CH₃)₃ | C(=O)OCH₂CH=CH₂ |
| CH₂CH₃ | C(CH₃)₃ | C(=O)OCH(CH₃)CH=CH₂ |
| CH₂CH₃ | C(CH₃)₃ | C(=O)OCH(CH₃)C(CH₃)=CH₂ |
| CH₂CH₃ | C(CH₃)₃ | C(=O)OCH₂CH=CHCH₃ |
| CH₂CH₃ | C(CH₃)₃ | C(=O)OCH(CH₃)CH=CHCH₃ |
| CH₂CH₃ | C(CH₃)₃ | C(=O)OCH₂CH=C(CH₃)₂ |
| CH₂CH₃ | C(CH₃)₃ | C(=O)OCH₂CH=CHCl |
| CH₂CH₃ | C(CH₃)₃ | C(=O)OCH₂CH=CCl₂ |
| CH₂CH₃ | C(CH₃)₃ | C(=O)OCH₂CH=CCl(CH₃) |
| CH₂CH₃ | C(CH₃)₃ | C(=O)OCH₂CH=CHBr |
| CH₂CH₃ | C(CH₃)₃ | C(=O)OCH₂CH=CBr₂ |
| CH₂CH₃ | C(CH₃)₃ | C(=O)OCH₂CH=CBr(CH₃) |

TABLE 33

| R¹ | R² | R³ |
|---|---|---|
| CF₃ | CH₃ | H |
| CF₃ | CH₃ | CH₃ |
| CF₃ | CH₃ | CH₂CH₃ |
| CF₃ | CH₃ | CH₂CH₂CH₃ |
| CF₃ | CH₃ | CH(CH₃)₂ |
| CF₃ | CH₃ | CH₂CH₂CH₂CH₃ |
| CF₃ | CH₃ | CH(CH₃)CH₂CH₃ |
| CF₃ | CH₃ | CH₂CH(CH₃)₂ |
| CF₃ | CH₃ | CH₂CH₂CH₂CH₂CH₃ |
| CF₃ | CH₃ | CH₂CH₂CH(CH₃)₂ |
| CF₃ | CH₃ | CH(CH₃)CH₂CH₂CH₃ |
| CF₃ | CH₃ | CH₂CH(CH₃)CH₂CH₃ |
| CF₃ | CH₃ | CH(CH₃)CH(CH₃)₂ |
| CF₃ | CH₃ | CH₂CH₂CH₂CH₂CH₂CH₃ |
| CF₃ | CH₃ | CH₂F |
| CF₃ | CH₃ | CF₃ |
| CF₃ | CH₃ | CH₂CH₂F |
| CF₃ | CH₃ | CH₂CF₃ |
| CF₃ | CH₃ | CH₂CH₂CH₂F |
| CF₃ | CH₃ | CH₂CH₂CF₃ |
| CF₃ | CH₃ | CH₂CH₂CH₂CH₂F |
| CF₃ | CH₃ | CH₂CH₂CH₂CF₃ |
| CF₃ | CH₃ | CH₂CH₂CH₂CH₂CF₃ |
| CF₃ | CH₃ | CH₂CH₂Cl |
| CF₃ | CH₃ | CHClCH₂Cl |
| CF₃ | CH₃ | CH₂CH₂Br |
| CF₃ | CH₃ | CHBrCH₂Br |
| CF₃ | CH₃ | CH₂CH₂CH₂Cl |
| CF₃ | CH₃ | CH₂CHClCH₂Cl |
| CF₃ | CH₃ | CH₂CH₂CH₂Br |
| CF₃ | CH₃ | CH₂CHBrCH₂Br |

TABLE 33-continued

| R¹ | R² | R³ |
|---|---|---|
| CF₃ | CH₃ | CH₂CH₂CH₂CH₂Cl |
| CF₃ | CH₃ | CH₂CH₂CH₂CH₂Br |
| CF₃ | CH₃ | CH₂CH₂CH₂CH₂CH₂Cl |
| CF₃ | CH₃ | CH₂CH₂CH₂CH₂CH₂Br |

TABLE 34

| R¹ | R² | R³ |
|---|---|---|
| CF₃ | CH₃ | CH₂CH₂CH₂CH₂CH₂CH₂Cl |
| CF₃ | CH₃ | CH₂CH₂CH₂CH₂CH₂CH₂Br |
| CF₃ | CH₃ | CH=CH₂ |
| CF₃ | CH₃ | CH₂CH=CH₂ |
| CF₃ | CH₃ | CH=CHCH₃ |
| CF₃ | CH₃ | C(CH₃)=CH₂ |
| CF₃ | CH₃ | CH=CHCH₂CH₃ |
| CF₃ | CH₃ | CH₂CH=CHCH₃ |
| CF₃ | CH₃ | CH₂CH₂CH=CH₂ |
| CF₃ | CH₃ | C(CH₃)=CHCH₃ |
| CF₃ | CH₃ | CH(CH₃)CH=CH₂ |
| CF₃ | CH₃ | CH=C(CH₃)₂ |
| CF₃ | CH₃ | CH₂C(CH₃)=CH₂ |
| CF₃ | CH₃ | C(CH₂CH₃)=CH₂ |
| CF₃ | CH₃ | CH=CHCH₂CH₂CH₃ |
| CF₃ | CH₃ | C(CH₃)=CHCH₂CH₃ |
| CF₃ | CH₃ | CH(CH₃)CH=CHCH₃ |
| CF₃ | CH₃ | CH(CH₃)CH₂CH=CH₂ |
| CF₃ | CH₃ | CH=C(CH₃)CH₂CH₃ |
| CF₃ | CH₃ | CH₂C(CH₃)=CHCH₃ |
| CF₃ | CH₃ | CH₂CH(CH₃)CH=CH₂ |
| CF₃ | CH₃ | CH=CHCH(CH₃)₂ |
| CF₃ | CH₃ | CH₂CH=C(CH₃)₂ |
| CF₃ | CH₃ | CH₂CH₂C(CH₃)=CH₂ |
| CF₃ | CH₃ | CH₂CH=C(CH₃)₂ |
| CF₃ | CH₃ | CH=CHCH₂CH₂CH₂CH₃ |
| CF₃ | CH₃ | CH=CHCl |
| CF₃ | CH₃ | CH=CCl₂ |
| CF₃ | CH₃ | CH=C(CH₃)Cl |
| CF₃ | CH₃ | CH₂CH=CHCl |
| CF₃ | CH₃ | CH₂CCl=CHCl |
| CF₃ | CH₃ | CH₂CH=CCl₂ |
| CF₃ | CH₃ | CH=CHBr |
| CF₃ | CH₃ | CH=CBr₂ |
| CF₃ | CH₃ | CH=C(CH₃)Br |

TABLE 35

| R¹ | R² | R³ |
|---|---|---|
| CF₃ | CH₃ | CH₂CH=CHBr |
| CF₃ | CH₃ | CH₂CBr=CHBr |
| CF₃ | CH₃ | CH₂CH=CBr₂ |
| CF₃ | CH₃ | CH₂CH=C(CH₃)Cl |
| CF₃ | CH₃ | CH₂CH=C(CF₃)Cl |
| CF₃ | CH₃ | CH₂CH=C(CH₃)Br |
| CF₃ | CH₃ | CH₂CH=C(CF₃)Br |
| CF₃ | CH₃ | CH=CHCF₃ |
| CF₃ | CH₃ | CH=CHCH₂CF₃ |
| CF₃ | CH₃ | CH₂CH=CHCH₂CF₃ |
| CF₃ | CH₃ | C≡CH |
| CF₃ | CH₃ | C≡CCH₃ |
| CF₃ | CH₃ | CH₂C≡CH |
| CF₃ | CH₃ | C≡CCH₂CH₃ |
| CF₃ | CH₃ | CH₂C≡CCH₃ |
| CF₃ | CH₃ | CH₂CH₂C≡CH |
| CF₃ | CH₃ | CH(CH₃)C≡CH |
| CF₃ | CH₃ | C≡CCH₂CH₂CH₃ |
| CF₃ | CH₃ | CH₂C≡CCH₂CH₃ |
| CF₃ | CH₃ | CH₂CH₂C≡CCH₃ |
| CF₃ | CH₃ | CH₂CH₂CH₂C≡CH |
| CF₃ | CH₃ | CH₂CH₂CH₂C≡CCH₃ |
| CF₃ | CH₃ | C≡CCl |

TABLE 35-continued

| R¹ | R² | R³ |
|---|---|---|
| CF₃ | CH₃ | CH₂C≡CCl |
| CF₃ | CH₃ | CH₂CH₂C≡CCl |
| CF₃ | CH₃ | CH₂CH₂CH₂C≡CCl |
| CF₃ | CH₃ | C≡CBr |
| CF₃ | CH₃ | CH₂C≡CBr |
| CF₃ | CH₃ | CH₂CH₂C≡CBr |
| CF₃ | CH₃ | CH₂CH₂CH₂C≡CBr |
| CF₃ | CH₃ | CH₂CH₂CH₂CH₂C≡CCl |
| CF₃ | CH₃ | CH₂OH |
| CF₃ | CH₃ | CH₂CH₂OH |
| CF₃ | CH₃ | CH₂CH₂CH₂OH |
| CF₃ | CH₃ | CH₂CH₂CH₂CH₂OH |

TABLE 36

| R¹ | R² | R³ |
|---|---|---|
| CF₃ | CH₃ | CH₂CH₂CH₂CH₂CH₂OH |
| CF₃ | CH₃ | CH₂OCH₃ |
| CF₃ | CH₃ | CH₂OCH₂CH₃ |
| CF₃ | CH₃ | CH₂OCH₂CH₂CH₃ |
| CF₃ | CH₃ | CH₂OCH(CH₃)₂ |
| CF₃ | CH₃ | CH₂OCH₂CH₂CH₂CH₃ |
| CF₃ | CH₃ | CH₂OCH₂CH₂CH₂CH₂CH₃ |
| CF₃ | CH₃ | CH₂CH₂OCH₃ |
| CF₃ | CH₃ | CH₂CH₂OCH₂CH₃ |
| CF₃ | CH₃ | CH₂CH₂OCH₂CH₂CH₃ |
| CF₃ | CH₃ | CH₂CH₂OCH(CH₃)₂ |
| CF₃ | CH₃ | CH₂CH₂CH₂OCH₃ |
| CF₃ | CH₃ | C(=O)OCH₃ |
| CF₃ | CH₃ | C(=O)OCH₂CH₃ |
| CF₃ | CH₃ | C(=O)OCH₂CH₂CH₃ |
| CF₃ | CH₃ | C(=O)OCH(CH₃)₂ |
| CF₃ | CH₃ | C(=O)OCH₂CH₂CH₂CH₃ |
| CF₃ | CH₃ | C(=O)OCH₂CH=CH₂ |
| CF₃ | CH₃ | C(=O)OCH(CH₃)CH=CH₂ |
| CF₃ | CH₃ | C(=O)OCH(CH₃)C(CH₃)=CH₂ |
| CF₃ | CH₃ | C(=O)OCH₂CH=CHCH₃ |
| CF₃ | CH₃ | C(=O)OCH(CH₃)CH=CHCH₃ |
| CF₃ | CH₃ | C(=O)OCH₂CH=C(CH₃)₂ |
| CF₃ | CH₃ | C(=O)OCH₂CH=CHCl |
| CF₃ | CH₃ | C(=O)OCH₂CH=CCl₂ |
| CF₃ | CH₃ | C(=O)OCH₂CH=CCl(CH₃) |
| CF₃ | CH₃ | C(=O)OCH₂CH=CHBr |
| CF₃ | CH₃ | C(=O)OCH₂CH=CBr₂ |
| CF₃ | CH₃ | C(=O)OCH₂CH=CBr(CH₃) |

TABLE 37

| R¹ | R² | R³ |
|---|---|---|
| CF₃ | CH₂CH₃ | H |
| CF₃ | CH₂CH₃ | CH₃ |
| CF₃ | CH₂CH₃ | CH₂CH₃ |
| CF₃ | CH₂CH₃ | CH₂CH₂CH₃ |
| CF₃ | CH₂CH₃ | CH(CH₃)₂ |
| CF₃ | CH₂CH₃ | CH₂CH₂CH₂CH₃ |
| CF₃ | CH₂CH₃ | CH(CH₃)CH₂CH₃ |
| CF₃ | CH₂CH₃ | CH₂CH(CH₃)₂ |
| CF₃ | CH₂CH₃ | CH₂CH₂CH₂CH₂CH₃ |
| CF₃ | CH₂CH₃ | CH₂CH₂CH(CH₃)₂ |
| CF₃ | CH₂CH₃ | CH(CH₃)CH₂CH₂CH₃ |
| CF₃ | CH₂CH₃ | CH₂CH(CH₃)CH₂CH₃ |
| CF₃ | CH₂CH₃ | CH(CH₃)CH(CH₃)₂ |
| CF₃ | CH₂CH₃ | CH₂CH₂CH₂CH₂CH₂CH₃ |
| CF₃ | CH₂CH₃ | CH₂F |
| CF₃ | CH₂CH₃ | CF₃ |
| CF₃ | CH₂CH₃ | CH₂CH₂F |
| CF₃ | CH₂CH₃ | CH₂CF₃ |
| CF₃ | CH₂CH₃ | CH₂CH₂CH₂F |
| CF₃ | CH₂CH₃ | CH₂CH₂CF₃ |
| CF₃ | CH₂CH₃ | CH₂CH₂CH₂CH₂F |

TABLE 37-continued

| R¹ | R² | R³ |
|---|---|---|
| CF₃ | CH₂CH₃ | CH₂CH₂CH₂CF₃ |
| CF₃ | CH₂CH₃ | CH₂CH₂CH₂CH₂CF₃ |
| CF₃ | CH₂CH₃ | CH₂CH₂Cl |
| CF₃ | CH₂CH₃ | CHClCH₂Cl |
| CF₃ | CH₂CH₃ | CH₂CH₂Br |
| CF₃ | CH₂CH₃ | CHBrCH₂Br |
| CF₃ | CH₂CH₃ | CH₂CH₂CH₂Cl |
| CF₃ | CH₂CH₃ | CH₂CHClCH₂Cl |
| CF₃ | CH₂CH₃ | CH₂CH₂CH₂Br |
| CF₃ | CH₂CH₃ | CH₂CHBrCH₂Br |
| CF₃ | CH₂CH₃ | CH₂CH₂CH₂CH₂Cl |
| CF₃ | CH₂CH₃ | CH₂CH₂CH₂CH₂Br |
| CF₃ | CH₂CH₃ | CH₂CH₂CH₂CH₂CH₂Cl |
| CF₃ | CH₂CH₃ | CH₂CH₂CH₂CH₂CH₂Br |

TABLE 38

| R¹ | R² | R³ |
|---|---|---|
| CF₃ | CH₂CH₃ | CH₂CH₂CH₂CH₂CH₂Cl |
| CF₃ | CH₂CH₃ | CH₂CH₂CH₂CH₂CH₂Br |
| CF₃ | CH₂CH₃ | CH=CH₂ |
| CF₃ | CH₂CH₃ | CH₂CH=CH₂ |
| CF₃ | CH₂CH₃ | CH=CHCH₃ |
| CF₃ | CH₂CH₃ | C(CH₃)=CH₂ |
| CF₃ | CH₂CH₃ | CH=CHCH₂CH₃ |
| CF₃ | CH₂CH₃ | CH₂CH=CHCH₃ |
| CF₃ | CH₂CH₃ | CH₂CH₂CH=CH₂ |
| CF₃ | CH₂CH₃ | C(CH₃)=CHCH₃ |
| CF₃ | CH₂CH₃ | CH(CH₃)CH=CH₂ |
| CF₃ | CH₂CH₃ | CH=C(CH₃)₂ |
| CF₃ | CH₂CH₃ | CH₂C(CH₃)=CH₂ |
| CF₃ | CH₂CH₃ | C(CH₂CH₃)=CH₂ |
| CF₃ | CH₂CH₃ | CH=CHCH₂CH₂CH₃ |
| CF₃ | CH₂CH₃ | C(CH₃)=CHCH₂CH₃ |
| CF₃ | CH₂CH₃ | CH(CH₃)CH=CHCH₃ |
| CF₃ | CH₂CH₃ | CH(CH₃)CH₂CH=CH₂ |
| CF₃ | CH₂CH₃ | CH=C(CH₃)CH₂CH₃ |
| CF₃ | CH₂CH₃ | CH₂C(CH₃)=CHCH₃ |
| CF₃ | CH₂CH₃ | CH₂CH(CH₃)CH=CH₂ |
| CF₃ | CH₂CH₃ | CH=CHCH(CH₃)₂ |
| CF₃ | CH₂CH₃ | CH₂CH=C(CH₃)₂ |
| CF₃ | CH₂CH₃ | CH₂CH₂C(CH₂)=CH₂ |
| CF₃ | CH₂CH₃ | CH₂CH=C(CH₃)₂ |
| CF₃ | CH₂CH₃ | CH=CHCH₂CH₂CH₂CH₃ |
| CF₃ | CH₂CH₃ | CH=CHCl |
| CF₃ | CH₂CH₃ | CH=CCl₂ |
| CF₃ | CH₂CH₃ | CH=C(CH₃)Cl |
| CF₃ | CH₂CH₃ | CH₂CH=CHCl |
| CF₃ | CH₂CH₃ | CH₂CCl=CHCl |
| CF₃ | CH₂CH₃ | CH₂CH=CCl₂ |
| CF₃ | CH₂CH₃ | CH=CHBr |
| CF₃ | CH₂CH₃ | CH=CBr₂ |
| CF₃ | CH₂CH₃ | CH=C(CH₃)Br |

TABLE 39

| R¹ | R² | R³ |
|---|---|---|
| CF₃ | CH₂CH₃ | CH₂CH=CHBr |
| CF₃ | CH₂CH₃ | CH₂CBr=CHBr |
| CF₃ | CH₂CH₃ | CH₂CH=CBr₂ |
| CF₃ | CH₂CH₃ | CH₂CH=C(CH₃)Cl |
| CF₃ | CH₂CH₃ | CH₂CH=C(CF₃)Cl |
| CF₃ | CH₂CH₃ | CH₂CH=C(CH₃)Br |
| CF₃ | CH₂CH₃ | CH₂CH=C(CF₃)Br |
| CF₃ | CH₂CH₃ | CH=CHCF₃ |
| CF₃ | CH₂CH₃ | CH=CHCH₂CF₃ |
| CF₃ | CH₂CH₃ | CH₂CH=CHCH₂CF₃ |
| CF₃ | CH₂CH₃ | C≡CH |
| CF₃ | CH₂CH₃ | C≡CCH₃ |
| CF₃ | CH₂CH₃ | CH₂C≡CH |

TABLE 39-continued

| R¹ | R² | R³ |
|---|---|---|
| CF₃ | CH₂CH₃ | C≡CCH₂CH₃ |
| CF₃ | CH₂CH₃ | CH₂C≡CCH₃ |
| CF₃ | CH₂CH₃ | CH₂CH₂C≡CH |
| CF₃ | CH₂CH₃ | CH(CH₃)C≡CH |
| CF₃ | CH₂CH₃ | C≡CCH₂CH₂CH₃ |
| CF₃ | CH₂CH₃ | CH₂C≡CCH₂CH₃ |
| CF₃ | CH₂CH₃ | CH₂CH₂C≡CCH₃ |
| CF₃ | CH₂CH₃ | CH₂CH₂CH₂C≡CH |
| CF₃ | CH₂CH₃ | CH₂CH₂CH₂C≡CCH₃ |
| CF₃ | CH₂CH₃ | C≡CCl |
| CF₃ | CH₂CH₃ | CH₂C≡CCl |
| CF₃ | CH₂CH₃ | CH₂CH₂C≡CCl |
| CF₃ | CH₂CH₃ | CH₂CH₂CH₂C≡CCl |
| CF₃ | CH₂CH₃ | C≡CBr |
| CF₃ | CH₂CH₃ | CH₂C≡CBr |
| CF₃ | CH₂CH₃ | CH₂CH₂C≡CBr |
| CF₃ | CH₂CH₃ | CH₂CH₂CH₂C≡CBr |
| CF₃ | CH₂CH₃ | CH₂CH₂CH₂CH₂C≡CCl |
| CF₃ | CH₂CH₃ | CH₂OH |
| CF₃ | CH₂CH₃ | CH₂CH₂OH |
| CF₃ | CH₂CH₃ | CH₂CH₂CH₂OH |
| CF₃ | CH₂CH₃ | CH₂CH₂CH₂CH₂OH |

TABLE 40

| R¹ | R² | R³ |
|---|---|---|
| CF₃ | CH₂CH₃ | CH₂CH₂CH₂CH₂CH₂OH |
| CF₃ | CH₂CH₃ | CH₂OCH₃ |
| CF₃ | CH₂CH₃ | CH₂OCH₂CH₃ |
| CF₃ | CH₂CH₃ | CH₂OCH₂CH₂CH₃ |
| CF₃ | CH₂CH₃ | CH₂OCH(CH₃)₂ |
| CF₃ | CH₂CH₃ | CH₂OCH₂CH₂CH₂CH₃ |
| CF₃ | CH₂CH₃ | CH₂OCH₂CH₂CH₂CH₂CH₃ |
| CF₃ | CH₂CH₃ | CH₂CH₂OCH₃ |
| CF₃ | CH₂CH₃ | CH₂CH₂OCH₂CH₃ |
| CF₃ | CH₂CH₃ | CH₂CH₂OCH₂CH₂CH₃ |
| CF₃ | CH₂CH₃ | CH₂CH₂OCH(CH₃)₂ |
| CF₃ | CH₂CH₃ | CH₂CH₂CH₂OCH₃ |
| CF₃ | CH₂CH₃ | C(=O)OCH₃ |
| CF₃ | CH₂CH₃ | C(=O)OCH₂CH₃ |
| CF₃ | CH₂CH₃ | C(=O)OCH₂CH₂CH₃ |
| CF₃ | CH₂CH₃ | C(=O)OCH(CH₃)₂ |
| CF₃ | CH₂CH₃ | C(=O)OCH₂CH₂CH₂CH₃ |
| CF₃ | CH₂CH₃ | C(=O)OCH₂CH=CH₂ |
| CF₃ | CH₂CH₃ | C(=O)OCH(CH₃)CH=CH₂ |
| CF₃ | CH₂CH₃ | C(=O)OCH(CH₃)C(CH₃)=CH₂ |
| CF₃ | CH₂CH₃ | C(=O)OCH₂CH=CHCH₃ |
| CF₃ | CH₂CH₃ | C(=O)OCH(CH₃)CH=CHCH₃ |
| CF₃ | CH₂CH₃ | C(=O)OCH₂CH=C(CH₃)₂ |
| CF₃ | CH₂CH₃ | C(=O)OCH₂CH=CHCl |
| CF₃ | CH₂CH₃ | C(=O)OCH₂CH=CCl(CH₃) |
| CF₃ | CH₂CH₃ | C(=O)OCH₂CH=CHBr |
| CF₃ | CH₂CH₃ | C(=O)OCH₂CH=CBr₂ |
| CF₃ | CH₂CH₃ | C(=O)OCH₂CH=CBr(CH₃) |

TABLE 41

| R¹ | R² | R³ |
|---|---|---|
| CF₃ | CH(CH₃)₂ | H |
| CF₃ | CH(CH₃)₂ | CH₃ |
| CF₃ | CH(CH₃)₂ | CH₂CH₃ |
| CF₃ | CH(CH₃)₂ | CH₂CH₂CH₃ |
| CF₃ | CH(CH₃)₂ | CH(CH₃)₂ |
| CF₃ | CH(CH₃)₂ | CH₂CH₂CH₂CH₃ |
| CF₃ | CH(CH₃)₂ | CH(CH₃)CH₂CH₃ |
| CF₃ | CH(CH₃)₂ | CH₂CH(CH₃)₂ |
| CF₃ | CH(CH₃)₂ | CH₂CH₂CH₂CH₂CH₃ |
| CF₃ | CH(CH₃)₂ | CH₂CH₂CH(CH₃)₂ |
| CF₃ | CH(CH₃)₂ | CH(CH₃)CH₂CH₂CH₃ |

TABLE 41-continued

| R¹ | R² | R³ |
|---|---|---|
| CF₃ | CH(CH₃)₂ | CH₂CH(CH₃)CH₂CH₃ |
| CF₃ | CH(CH₃)₂ | CH(CH₃)CH(CH₃)₂ |
| CF₃ | CH(CH₃)₂ | CH₂CH₂CH₂CH₂CH₂CH₃ |
| CF₃ | CH(CH₃)₂ | CH₂F |
| CF₃ | CH(CH₃)₂ | CF₃ |
| CF₃ | CH(CH₃)₂ | CH₂CH₂F |
| CF₃ | CH(CH₃)₂ | CH₂CF₃ |
| CF₃ | CH(CH₃)₂ | CH₂CH₂CH₂F |
| CF₃ | CH(CH₃)₂ | CH₂CH₂CF₃ |
| CF₃ | CH(CH₃)₂ | CH₂CH₂CH₂CH₂F |
| CF₃ | CH(CH₃)₂ | CH₂CH₂CH₂CF₃ |
| CF₃ | CH(CH₃)₂ | CH₂CH₂CH₂CH₂CF₃ |
| CF₃ | CH(CH₃)₂ | CH₂CH₂Cl |
| CF₃ | CH(CH₃)₂ | CHClCH₂Cl |
| CF₃ | CH(CH₃)₂ | CH₂CH₂Br |
| CF₃ | CH(CH₃)₂ | CHBrCH₂Br |
| CF₃ | CH(CH₃)₂ | CH₂CH₂CH₂Cl |
| CF₃ | CH(CH₃)₂ | CH₂CHClCH₂Cl |
| CF₃ | CH(CH₃)₂ | CH₂CH₂CH₂Br |
| CF₃ | CH(CH₃)₂ | CH₂CHBrCH₂Br |
| CF₃ | CH(CH₃)₂ | CH₂CH₂CH₂CH₂Cl |
| CF₃ | CH(CH₃)₂ | CH₂CH₂CH₂CH₂Br |
| CF₃ | CH(CH₃)₂ | CH₂CH₂CH₂CH₂CH₂Cl |
| CF₃ | CH(CH₃)₂ | CH₂CH₂CH₂CH₂CH₂Br |

TABLE 42

| R¹ | R² | R³ |
|---|---|---|
| CF₃ | CH(CH₃)₂ | CH₂CH₂CH₂CH₂CH₂CH₂Cl |
| CF₃ | CH(CH₃)₂ | CH₂CH₂CH₂CH₂CH₂CH₂Br |
| CF₃ | CH(CH₃)₂ | CH=CH₂ |
| CF₃ | CH(CH₃)₂ | CH₂CH=CH₂ |
| CF₃ | CH(CH₃)₂ | CH=CHCH₃ |
| CF₃ | CH(CH₃)₂ | C(CH₃)=CH₂ |
| CF₃ | CH(CH₃)₂ | CH=CHCH₂CH₃ |
| CF₃ | CH(CH₃)₂ | CH₂CH=CHCH₃ |
| CF₃ | CH(CH₃)₂ | CH₂CH₂CH=CH₂ |
| CF₃ | CH(CH₃)₂ | C(CH₃)=CHCH₃ |
| CF₃ | CH(CH₃)₂ | CH(CH₃)CH=CH₂ |
| CF₃ | CH(CH₃)₂ | CH=C(CH₃)₂ |
| CF₃ | CH(CH₃)₂ | CH₂C(CH₃)=CH₂ |
| CF₃ | CH(CH₃)₂ | C(CH₂CH₃)=CH₂ |
| CF₃ | CH(CH₃)₂ | CH=CHCH₂CH₂CH₃ |
| CF₃ | CH(CH₃)₂ | C(CH₃)=CHCH₂CH₃ |
| CF₃ | CH(CH₃)₂ | CH(CH₃)CH=CHCH₃ |
| CF₃ | CH(CH₃)₂ | CH(CH₃)CH₂CH=CH₂ |
| CF₃ | CH(CH₃)₂ | CH=C(CH₃)CH₂CH₃ |
| CF₃ | CH(CH₃)₂ | CH₂C(CH₃)=CHCH₃ |
| CF₃ | CH(CH₃)₂ | CH₂CH(CH₃)CH=CH₂ |
| CF₃ | CH(CH₃)₂ | CH=CHCH(CH₃)₂ |
| CF₃ | CH(CH₃)₂ | CH₂CH=C(CH₃)₂ |
| CF₃ | CH(CH₃)₂ | CH₂CH₂C(CH₂)=CH₂ |
| CF₃ | CH(CH₃)₂ | CH₂CH=C(CH₃)₂ |
| CF₃ | CH(CH₃)₂ | CH=CHCH₂CH₂CH₂CH₃ |
| CF₃ | CH(CH₃)₂ | CH=CHCl |
| CF₃ | CH(CH₃)₂ | CH=CCl₂ |
| CF₃ | CH(CH₃)₂ | CH=C(CH₃)Cl |
| CF₃ | CH(CH₃)₂ | CH₂CH=CHCl |
| CF₃ | CH(CH₃)₂ | CH₂CCl=CHCl |
| CF₃ | CH(CH₃)₂ | CH₂CH=CCl₂ |
| CF₃ | CH(CH₃)₂ | CH=CHBr |
| CF₃ | CH(CH₃)₂ | CH=CBr₂ |
| CF₃ | CH(CH₃)₂ | CH=C(CH₃)Br |

TABLE 43

| R¹ | R² | R³ |
|---|---|---|
| CF₃ | CH(CH₃)₂ | CH₂CH=CHBr |
| CF₃ | CH(CH₃)₂ | CH₂CBr=CHBr |
| CF₃ | CH(CH₃)₂ | CH₂CH=CBr₂ |

TABLE 43-continued

| R¹ | R² | R³ |
|---|---|---|
| CF₃ | CH(CH₃)₂ | CH₂CH=C(CH₃)Cl |
| CF₃ | CH(CH₃)₂ | CH₂CH=C(CF₃)Cl |
| CF₃ | CH(CH₃)₂ | CH₂CH=C(CH₃)Br |
| CF₃ | CH(CH₃)₂ | CH₂CH=C(CF₃)Br |
| CF₃ | CH(CH₃)₂ | CH=CHCF₃ |
| CF₃ | CH(CH₃)₂ | CH=CHCH₂CF₃ |
| CF₃ | CH(CH₃)₂ | CH₂CH=CHCH₂CF₃ |
| CF₃ | CH(CH₃)₂ | C≡CH |
| CF₃ | CH(CH₃)₂ | C≡CCH₃ |
| CF₃ | CH(CH₃)₂ | CH₂C≡CH |
| CF₃ | CH(CH₃)₂ | C≡CCH₂CH₃ |
| CF₃ | CH(CH₃)₂ | CH₂C≡CCH₃ |
| CF₃ | CH(CH₃)₂ | CH₂CH₂C≡CH |
| CF₃ | CH(CH₃)₂ | CH(CH₃)C≡CH |
| CF₃ | CH(CH₃)₂ | C≡CCH₂CH₂CH₃ |
| CF₃ | CH(CH₃)₂ | CH₂C≡CCH₂CH₃ |
| CF₃ | CH(CH₃)₂ | CH₂CH₂C≡CCH₃ |
| CF₃ | CH(CH₃)₂ | CH₂CH₂CH₂C≡CH |
| CF₃ | CH(CH₃)₂ | CH₂CH₂CH₂C≡CCH₃ |
| CF₃ | CH(CH₃)₂ | C≡CCl |
| CF₃ | CH(CH₃)₂ | CH₂C≡CCl |
| CF₃ | CH(CH₃)₂ | CH₂CH₂C≡CCl |
| CF₃ | CH(CH₃)₂ | CH₂CH₂CH₂C≡CCl |
| CF₃ | CH(CH₃)₂ | C≡CBr |
| CF₃ | CH(CH₃)₂ | CH₂C≡CBr |
| CF₃ | CH(CH₃)₂ | CH₂CH₂C≡CBr |
| CF₃ | CH(CH₃)₂ | CH₂CH₂CH₂C≡CBr |
| CF₃ | CH(CH₃)₂ | CH₂CH₂CH₂CH₂C≡CCl |
| CF₃ | CH(CH₃)₂ | CH₂OH |
| CF₃ | CH(CH₃)₂ | CH₂CH₂OH |
| CF₃ | CH(CH₃)₂ | CH₂CH₂CH₂OH |
| CF₃ | CH(CH₃)₂ | CH₂CH₂CH₂CH₂OH |

TABLE 44

| R¹ | R² | R³ |
|---|---|---|
| CF₃ | CH(CH₃)₂ | CH₂CH₂CH₂CH₂CH₂OH |
| CF₃ | CH(CH₃)₂ | CH₂OCH₃ |
| CF₃ | CH(CH₃)₂ | CH₂OCH₂CH₃ |
| CF₃ | CH(CH₃)₂ | CH₂OCH₂CH₂CH₃ |
| CF₃ | CH(CH₃)₂ | CH₂OCH(CH₃)₂ |
| CF₃ | CH(CH₃)₂ | CH₂OCH₂CH₂CH₂CH₃ |
| CF₃ | CH(CH₃)₂ | CH₂OCH₂CH₂CH₂CH₂CH₃ |
| CF₃ | CH(CH₃)₂ | CH₂CH₂OCH₃ |
| CF₃ | CH(CH₃)₂ | CH₂CH₂OCH₂CH₃ |
| CF₃ | CH(CH₃)₂ | CH₂CH₂OCH₂CH₂CH₃ |
| CF₃ | CH(CH₃)₂ | CH₂CH₂OCH(CH₃)₂ |
| CF₃ | CH(CH₃)₂ | CH₂CH₂CH₂OCH₃ |
| CF₃ | CH(CH₃)₂ | C(=O)OCH₃ |
| CF₃ | CH(CH₃)₂ | C(=O)OCH₂CH₃ |
| CF₃ | CH(CH₃)₂ | C(=O)OCH₂CH₂CH₃ |
| CF₃ | CH(CH₃)₂ | C(=O)OCH(CH₃)₂ |
| CF₃ | CH(CH₃)₂ | C(=O)OCH₂CH₂CH₂CH₃ |
| CF₃ | CH(CH₃)₂ | C(=O)OCH₂CH=CH₂ |
| CF₃ | CH(CH₃)₂ | C(=O)OCH(CH₃)CH=CH₂ |
| CF₃ | CH(CH₃)₂ | C(=O)OCH(CH₃)C(CH₃)=CH₂ |
| CF₃ | CH(CH₃)₂ | C(=O)OCH₂CH=CHCH₃ |
| CF₃ | CH(CH₃)₂ | C(=O)OCH(CH₃)CH=CHCH₃ |
| CF₃ | CH(CH₃)₂ | C(=O)OCH₂CH=C(CH₃)₂ |
| CF₃ | CH(CH₃)₂ | C(=O)OCH₂CH=CHCl |
| CF₃ | CH(CH₃)₂ | C(=O)OCH₂CH=CCl₂ |
| CF₃ | CH(CH₃)₂ | C(=O)OCH₂CH=CCl(CH₃) |
| CF₃ | CH(CH₃)₂ | C(=O)OCH₂CH=CHBr |
| CF₃ | CH(CH₃)₂ | C(=O)OCH₂CH=CBr₂ |
| CF₃ | CH(CH₃)₂ | C(=O)OCH₂CH=CBr(CH₃) |

TABLE 45

| R¹ | R² | R³ |
|---|---|---|
| CF₃ | C(CH₃)₃ | H |
| CF₃ | C(CH₃)₃ | CH₃ |
| CF₃ | C(CH₃)₃ | CH₂CH₃ |
| CF₃ | C(CH₃)₃ | CH₂CH₂CH₃ |
| CF₃ | C(CH₃)₃ | CH(CH₃)₂ |
| CF₃ | C(CH₃)₃ | CH₂CH₂CH₂CH₃ |
| CF₃ | C(CH₃)₃ | CH(CH₃)CH₂CH₃ |
| CF₃ | C(CH₃)₃ | CH₂CH(CH₃)₂ |
| CF₃ | C(CH₃)₃ | CH₂CH₂CH₂CH₂CH₃ |
| CF₃ | C(CH₃)₃ | CH₂CH₂CH(CH₃)₂ |
| CF₃ | C(CH₃)₃ | CH(CH₃)CH₂CH₂CH₃ |
| CF₃ | C(CH₃)₃ | CH₂CH(CH₃)CH₂CH₃ |
| CF₃ | C(CH₃)₃ | CH(CH₃)CH(CH₃)₂ |
| CF₃ | C(CH₃)₃ | CH₂CH₂CH₂CH₂CH₂CH₃ |
| CF₃ | C(CH₃)₃ | CH₂F |
| CF₃ | C(CH₃)₃ | CF₃ |
| CF₃ | C(CH₃)₃ | CH₂CH₂F |
| CF₃ | C(CH₃)₃ | CH₂CF₃ |
| CF₃ | C(CH₃)₃ | CH₂CH₂CH₂F |
| CF₃ | C(CH₃)₃ | CH₂CH₂CF₃ |
| CF₃ | C(CH₃)₃ | CH₂CH₂CH₂CH₂F |
| CF₃ | C(CH₃)₃ | CH₂CH₂CH₂CF₃ |
| CF₃ | C(CH₃)₃ | CH₂CH₂CH₂CH₂CF₃ |
| CF₃ | C(CH₃)₃ | CH₂CH₂Cl |
| CF₃ | C(CH₃)₃ | CHClCH₂Cl |
| CF₃ | C(CH₃)₃ | CH₂CH₂Br |
| CF₃ | C(CH₃)₃ | CHBrCH₂Br |
| CF₃ | C(CH₃)₃ | CH₂CH₂CH₂Cl |
| CF₃ | C(CH₃)₃ | CH₂CHClCH₂Cl |
| CF₃ | C(CH₃)₃ | CH₂CH₂CH₂Br |
| CF₃ | C(CH₃)₃ | CH₂CHBrCH₂Br |
| CF₃ | C(CH₃)₃ | CH₂CH₂CH₂CH₂Cl |
| CF₃ | C(CH₃)₃ | CH₂CH₂CH₂CH₂Br |
| CF₃ | C(CH₃)₃ | CH₂CH₂CH₂CH₂CH₂Cl |
| CF₃ | C(CH₃)₃ | CH₂CH₂CH₂CH₂CH₂Br |

TABLE 46

| R¹ | R² | R³ |
|---|---|---|
| CF₃ | C(CH₃)₃ | CH₂CH₂CH₂CH₂CH₂CH₂Cl |
| CF₃ | C(CH₃)₃ | CH₂CH₂CH₂CH₂CH₂CH₂Br |
| CF₃ | C(CH₃)₃ | CH=CH₂ |
| CF₃ | C(CH₃)₃ | CH₂CH=CH₂ |
| CF₃ | C(CH₃)₃ | CH=CHCH₃ |
| CF₃ | C(CH₃)₃ | C(CH₃)=CH₂ |
| CF₃ | C(CH₃)₃ | CH=CHCH₂CH₃ |
| CF₃ | C(CH₃)₃ | CH₂CH=CHCH₃ |
| CF₃ | C(CH₃)₃ | CH₂CH₂CH=CH₂ |
| CF₃ | C(CH₃)₃ | C(CH₃)=CHCH₃ |
| CF₃ | C(CH₃)₃ | CH(CH₃)CH=CH₂ |
| CF₃ | C(CH₃)₃ | CH=C(CH₃)₂ |
| CF₃ | C(CH₃)₃ | CH₂C(CH₃)=CH₂ |
| CF₃ | C(CH₃)₃ | C(CH₂CH₃)=CH₂ |
| CF₃ | C(CH₃)₃ | CH=CHCH₂CH₂CH₃ |
| CF₃ | C(CH₃)₃ | C(CH₃)=CHCH₂CH₃ |
| CF₃ | C(CH₃)₃ | CH(CH₃)CH=CHCH₃ |
| CF₃ | C(CH₃)₃ | CH(CH₃)CH₂CH=CH₂ |
| CF₃ | C(CH₃)₃ | CH=C(CH₃)CH₂CH₃ |
| CF₃ | C(CH₃)₃ | CH₂C(CH₃)=CHCH₃ |
| CF₃ | C(CH₃)₃ | CH₂CH(CH₃)CH=CH₂ |
| CF₃ | C(CH₃)₃ | CH=CHCH(CH₃)₂ |
| CF₃ | C(CH₃)₃ | CH₂CH=C(CH₃)₂ |
| CF₃ | C(CH₃)₃ | CH₂CH₂C(CH₂)=CH₂ |
| CF₃ | C(CH₃)₃ | CH₂CH=C(CH₃)₂ |
| CF₃ | C(CH₃)₃ | CH=CHCH₂CH₂CH₃ |
| CF₃ | C(CH₃)₃ | CH=CHCl |
| CF₃ | C(CH₃)₃ | CH=CCl₂ |
| CF₃ | C(CH₃)₃ | CH=C(CH₃)Cl |
| CF₃ | C(CH₃)₃ | CH₂CH=CHCl |
| CF₃ | C(CH₃)₃ | CH₂CCl=CHCl |
| CF₃ | C(CH₃)₃ | CH₂CH=CCl₂ |
| CF₃ | C(CH₃)₃ | CH=CHBr |

TABLE 46-continued

| R¹ | R² | R³ |
|---|---|---|
| CF₃ | C(CH₃)₃ | CH=CBr₂ |
| CF₃ | C(CH₃)₃ | CH=C(CH₃)Br |

TABLE 47

| R¹ | R² | R³ |
|---|---|---|
| CF₃ | C(CH₃)₃ | CH₂CH=CHBr |
| CF₃ | C(CH₃)₃ | CH₂CBr=CHBr |
| CF₃ | C(CH₃)₃ | CH₂CH=CBr₂ |
| CF₃ | C(CH₃)₃ | CH₂CH=C(CH₃)Cl |
| CF₃ | C(CH₃)₃ | CH₂CH=C(CF₃)Cl |
| CF₃ | C(CH₃)₃ | CH₂CH=C(CH₃)Br |
| CF₃ | C(CH₃)₃ | CH₂CH=C(CF₃)Br |
| CF₃ | C(CH₃)₃ | CH=CHCF₃ |
| CF₃ | C(CH₃)₃ | CH=CHCH₂CF₃ |
| CF₃ | C(CH₃)₃ | CH₂CH=CHCH₂CF₃ |
| CF₃ | C(CH₃)₃ | C≡CH |
| CF₃ | C(CH₃)₃ | C≡CCH₃ |
| CF₃ | C(CH₃)₃ | CH₂C≡CH |
| CF₃ | C(CH₃)₃ | C≡CCH₂CH₃ |
| CF₃ | C(CH₃)₃ | CH₂C≡CCH₃ |
| CF₃ | C(CH₃)₃ | CH₂CH₂C≡CH |
| CF₃ | C(CH₃)₃ | CH(CH₃)C≡CH |
| CF₃ | C(CH₃)₃ | C≡CCH₂CH₂CH₃ |
| CF₃ | C(CH₃)₃ | CH₂C≡CCH₂CH₃ |
| CF₃ | C(CH₃)₃ | CH₂CH₂C≡CCH₃ |
| CF₃ | C(CH₃)₃ | CH₂CH₂CH₂C≡CH |
| CF₃ | C(CH₃)₃ | CH₂CH₂CH₂C≡CCH₃ |
| CF₃ | C(CH₃)₃ | C≡CCl |
| CF₃ | C(CH₃)₃ | CH₂C≡CCl |
| CF₃ | C(CH₃)₃ | CH₂CH₂C≡CCl |
| CF₃ | C(CH₃)₃ | CH₂CH₂CH₂C≡CCl |
| CF₃ | C(CH₃)₃ | C≡CBr |
| CF₃ | C(CH₃)₃ | CH₂C≡CBr |
| CF₃ | C(CH₃)₃ | CH₂CH₂C≡CBr |
| CF₃ | C(CH₃)₃ | CH₂CH₂CH₂C≡CBr |
| CF₃ | C(CH₃)₃ | CH₂CH₂CH₂C≡CCl |
| CF₃ | C(CH₃)₃ | CH₂OH |
| CF₃ | C(CH₃)₃ | CH₂CH₂OH |
| CF₃ | C(CH₃)₃ | CH₂CH₂CH₂OH |
| CF₃ | C(CH₃)₃ | CH₂CH₂CH₂CH₂OH |

TABLE 48

| R¹ | R² | R³ |
|---|---|---|
| CF₃ | C(CH₃)₃ | CH₂CH₂CH₂CH₂CH₂OH |
| CF₃ | C(CH₃)₃ | CH₂OCH₃ |
| CF₃ | C(CH₃)₃ | CH₂OCH₂CH₃ |
| CF₃ | C(CH₃)₃ | CH₂OCH₂CH₂CH₃ |
| CF₃ | C(CH₃)₃ | CH₂OCH(CH₃)₂ |
| CF₃ | C(CH₃)₃ | CH₂OCH₂CH₂CH₂CH₃ |
| CF₃ | C(CH₃)₃ | CH₂OCH₂CH₂CH₂CH₂CH₃ |
| CF₃ | C(CH₃)₃ | CH₂CH₂OCH₃ |
| CF₃ | C(CH₃)₃ | CH₂CH₂OCH₂CH₃ |
| CF₃ | C(CH₃)₃ | CH₂CH₂OCH₂CH₂CH₃ |
| CF₃ | C(CH₃)₃ | CH₂CH₂OCH(CH₃)₂ |
| CF₃ | C(CH₃)₃ | CH₂CH₂CH₂OCH₃ |
| CF₃ | C(CH₃)₃ | C(=O)OCH₃ |
| CF₃ | C(CH₃)₃ | C(=O)OCH₂CH₃ |
| CF₃ | C(CH₃)₃ | C(=O)OCH₂CH₂CH₃ |
| CF₃ | C(CH₃)₃ | C(=O)OCH(CH₃)₂ |
| CF₃ | C(CH₃)₃ | C(=O)OCH₂CH₂CH₂CH₃ |
| CF₃ | C(CH₃)₃ | C(=O)OCH₂CH=CH₂ |
| CF₃ | C(CH₃)₃ | C(=O)OCH(CH₃)CH=CH₂ |
| CF₃ | C(CH₃)₃ | C(=O)OCH(CH₃)C(CH₃)=CH₂ |
| CF₃ | C(CH₃)₃ | C(=O)OCH₂CH=CHCH₃ |
| CF₃ | C(CH₃)₃ | C(=O)OCH(CH₃)CH=CHCH₃ |
| CF₃ | C(CH₃)₃ | C(=O)OCH₂CH=C(CH₃)₂ |
| CF₃ | C(CH₃)₃ | C(=O)OCH₂CH=CHCl |
| CF₃ | C(CH₃)₃ | C(=O)OCH₂CH=CCl₂ |

TABLE 48-continued

| $R^1$ | $R^2$ | $R^3$ |
|---|---|---|
| $CF_3$ | $C(CH_3)_3$ | $C(=O)OCH_2CH=CCl(CH_3)$ |
| $CF_3$ | $C(CH_3)_3$ | $C(=O)OCH_2CH=CHBr$ |
| $CF_3$ | $C(CH_3)_3$ | $C(=O)OCH_2CH=CBr_2$ |
| $CF_3$ | $C(CH_3)_3$ | $C(=O)OCH_2CH=CBr(CH_3)$ |

TABLE 49

| $R^1$ | $R^2$ | $R^3$ |
|---|---|---|
| $CH_2CH_2CH_3$ | $CH_3$ | H |
| $CH_2CH_2CH_3$ | $CH_3$ | $CH_3$ |
| $CH_2CH_2CH_3$ | $CH_3$ | $CH_2CH_3$ |
| $CH_2CH_2CH_3$ | $CH_3$ | $CH_2CH_2CH_3$ |
| $CH_2CH_2CH_3$ | $CH_3$ | $CH=CH_2$ |
| $CH_2CH_2CH_3$ | $CH_3$ | $CH_2CH=CH_2$ |
| $CH_2CH_2CH_3$ | $CH_3$ | $CH=CHCH_3$ |
| $CH_2CH_2CH_3$ | $CH_3$ | $C(CH_3)=CH_2$ |
| $CH_2CH_2CH_3$ | $CH_3$ | $CH=CHBr$ |
| $CH_2CH_2CH_3$ | $CH_3$ | $CH=CCl_2$ |
| $CH_2CH_2CH_3$ | $CH_3$ | $CH=CHBr$ |
| $CH_2CH_2CH_3$ | $CH_3$ | $CH=CBr_2$ |
| $CH_2CH_2CH_3$ | $CH_3$ | $C\equiv CH$ |
| $CH_2CH_2CH_3$ | $CH_3$ | $C\equiv CCH_3$ |
| $CH_2CH_2CH_3$ | $CH_3$ | $CH_2C\equiv CH$ |
| $CH_2CH_2CH_3$ | $CH_3$ | $C\equiv CCl$ |
| $CH_2CH_2CH_3$ | $CH_3$ | $C\equiv CBr$ |
| $CH_2CH_2CH_3$ | $CH_3$ | $CH_2OH$ |
| $CH_2CH_2CH_3$ | $CH_3$ | $CH_2CH_2OH$ |
| $CH_2CH_2CH_3$ | $CH_3$ | $CH_2OCH_3$ |
| $CH_2CH_2CH_3$ | $CH_3$ | $CH_2OCH_2CH_3$ |
| $CH_2CH_2CH_3$ | $CH_3$ | $C(=O)OCH_3$ |
| $CH_2CH_2CH_3$ | $CH_3$ | $C(=O)OCH_2CH_3$ |
| $CH_2CH_2CH_3$ | $CH_3$ | $C(=O)OCH_2CH=CCl_2$ |
| $CH_2CH_2CH_3$ | $CH_3$ | $C(=O)OCH_2CH=CBr_2$ |

TABLE 50

| $R^1$ | $R^2$ | $R^3$ |
|---|---|---|
| $CH_2CH_2CH_2CH_3$ | $CH_3$ | H |
| $CH_2CH_2CH_2CH_3$ | $CH_3$ | $CH_3$ |
| $CH_2CH_2CH_2CH_3$ | $CH_3$ | $CH_2CH_3$ |
| $CH_2CH_2CH_2CH_3$ | $CH_3$ | $CH_2CH_2CH_3$ |
| $CH_2CH_2CH_2CH_3$ | $CH_3$ | $CH=CH_2$ |
| $CH_2CH_2CH_2CH_3$ | $CH_3$ | $CH_2CH=CH_2$ |
| $CH_2CH_2CH_2CH_3$ | $CH_3$ | $CH=CHCH_3$ |
| $CH_2CH_2CH_2CH_3$ | $CH_3$ | $C(CH_3)=CH_2$ |
| $CH_2CH_2CH_2CH_3$ | $CH_3$ | $CH=CHBr$ |
| $CH_2CH_2CH_2CH_3$ | $CH_3$ | $CH=CCl_2$ |
| $CH_2CH_2CH_2CH_3$ | $CH_3$ | $CH=CHBr$ |
| $CH_2CH_2CH_2CH_3$ | $CH_3$ | $CH=CBr_2$ |
| $CH_2CH_2CH_2CH_3$ | $CH_3$ | $C\equiv CH$ |
| $CH_2CH_2CH_2CH_3$ | $CH_3$ | $C\equiv CCH_3$ |
| $CH_2CH_2CH_2CH_3$ | $CH_3$ | $CH_2C\equiv CH$ |
| $CH_2CH_2CH_2CH_3$ | $CH_3$ | $C\equiv CCl$ |
| $CH_2CH_2CH_2CH_3$ | $CH_3$ | $C\equiv CBr$ |
| $CH_2CH_2CH_2CH_3$ | $CH_3$ | $CH_2OH$ |
| $CH_2CH_2CH_2CH_3$ | $CH_3$ | $CH_2CH_2OH$ |
| $CH_2CH_2CH_2CH_3$ | $CH_3$ | $CH_2OCH_3$ |
| $CH_2CH_2CH_2CH_3$ | $CH_3$ | $CH_2OCH_2CH_3$ |
| $CH_2CH_2CH_2CH_3$ | $CH_3$ | $C(=O)OCH_3$ |
| $CH_2CH_2CH_2CH_3$ | $CH_3$ | $C(=O)OCH_2CH_3$ |
| $CH_2CH_2CH_2CH_3$ | $CH_3$ | $C(=O)OCH_2CH=CCl_2$ |
| $CH_2CH_2CH_2CH_3$ | $CH_3$ | $C(=O)OCH_2CH=CBr_2$ |

The noxious arthropod pests against which the compound of the present invention has activity may include noxious insect pests and noxious acarina pests, and concreatly:

Hemiptera:
Delphacidae such as *Laodelphax striatellus, Nilaparvata lugens, Sogatella furcifera* and the like,
Deltocephalidae such as *Nephotettix cincticeps, Nephotettix virescens* and the like,
Aphididae such as *Aphis gossypii, Myzus persicae* and the like,
Pentatomidae such as *Nezara antennata, Riptortus clavetus* and the like,
Aleyrodidae such as *Trialeurodes vaporariorum, Bemisia argentifolli* and the like,
Coccidae such as *Aonidiella aurantii, Comstockaspis perniciosa, Unaspis citri, Ceroplastes rubens, Icerya purchasi* and the like,
Tingidae,
Psyllidae, and the like;

Lepidoptera:
Pyralidae such as *Chilo suppressalis, Cnaphalocrocis medinalis, Notarcha derogata, Plodia interpunctella* and the like,
Noctuidae such as *Spodoptera litura, Pseudaletia separata, Thoricoplusia* spp., *Heliothis* spp., *Helicoverpa* spp. and the like,
Pieridae such as *Pieris rapae* and the like,
Tortricidae such as *Adoxophyes* spp. (ex. *Adoxophyes orana fasciata*), *Grapholita molesta, Cydia pomonella* and the like,
Carposimidae such as *Carposina niponensis* and the like,
Lyonetiidae such as *Lyonetia* spp. and the like,
Lymantriidae such as *Lymantria* spp., *Euproctis* spp., and the like,
Yponomeutidae such as *Plutella xylostella* and the like,
Gelechiidae such as *Pectinophora gossypiella* and the like,
Arctiidae such as *Hyphantria cunea* and the like,
Tineidae such as *Tinea translucens, Tineola bisselliella* and the like;

Diptera:
Calicidae such as *Culex pipiens pallens, Culex tritaeniorhynchus, Culex quinquefasciatus* and the like,
*Aedes* spp. such as *Aedes aegypti, Aedes albopictus* and the like,
*Anopheles* such as *Anopheles sinensis* and the like,
Chironomidae,
Muscidae such as *Musca domestica, Muscina stabulans* and the like,
Calliphoridae,
Sarcophagidae,
Fanniidae,
Anthomyiidae such as *Delia platura, Delia antiqua* and the like,
Tephritidae,
Drosophilidae,
Psychodidae,
Tabanidae,
Simuliidae,
Stomoxyidae,
Agromyzidae, and the like;

Coleoptera:
*Diabrotica* spp. such as *Diabrotica virgifera virgifera, Diabrotica undecimpunctata howardi* and the like,
Scarabaeidae such as *Anomala cuprea, Anomala rufocuprea* and the like,
Curculionidae such as *Sitophilus zeamais, Lissorhoptrus oryzophilus, Callosobruchuys chienensis* and the like,
Tenebrionidae such as *Tenebrio molitor, Tribolium castaneum* and the like, Chrysomelidae such as *Oulema oryzae, Aulacophora femoralis, Phyllotreta striolata, Leptinotarsa decemlineata* and the like,
Anobiidae,
*Epilachna* spp. such as *Epilachna vigintioctopunctata* and the like,
Lyctidae,
Bostrychidae,
Cerambycidae,
*Paederus fuscipes*;

Blattodea:
*Blattella germanica, Periplaneta fuliginosa, Periplaneta americana, Periplaneta brunnea, Blatta orientalis* and the like;

Thysanoptera:
*Thrips palmi, Thrips tabaci, Frankliniella occidentalis* and the like;

Hymenoptera:
Formicidae such as *Monomorium pharaonis*, Vespidae, bethylid wasp, Tenthredinidae such as *Athalia japonica*, and the like;

Orthoptera:
Gryllotalpidae, Acrididae, and the like;

Aphaniptera:
*Ctenocephalides felis, Ctenocephalides canis, Pulex irritans, Xenopsylla cheopis*, and the like;

Anoplura:
*Pediculus humanus corporis, Phthiruspubis, Haema topinus eurysternus, Dalmalinia ovis*, and the like;

Isoptera:
*Reticulitermes speratus, Coptotermes formosanus*, and the like;

Acarina:
Tetranychidae such as *Tetranychus urticae, Panonychus citri, Oligonychus* spp., and the like,
Eriophyidae such as *Aculops pelekassi* and the like,
Tarsonemidae such as *Polyphagotarsonemus latus*, and the like,
Tenuipalpidae,
Tuckerellidae,
Ixodidae such as *Haemaphysalis longicornis, Haemaphysalis flava, Dermacentor taiwanicus, Ixodes ovatus, Ixodes persulcatus, Boophilus microplus, Rhipicephalus sanguineus*, and the like,
Acaridae such as *Tyrophagus putrescentiae*, and the like,
Epidermoptidae such as *Dermatophagoides farinae, Dermatophagoides ptrenyssnus*, and the like,
Cheyletidae such as *Cheyletus eruditus, Cheyletus malaccensis, Cheyletus moorei*, and the like,
Dermanyssidae.

The noxious arthropod controlling composition of the present invention contains the compound of the present invention and an inert carrier. Generally, it is a preparation obtained by mixing the compound of the present invention and an inert carrier such as a solid carrier, a liquid carrier, a gaseous carrier and/or bait for poison bait, and if necessary, adding a surfactant and other adjuvant for formulation. The formulation includes, for example, an emulsifiable concentrate, an oil solution, a dust, a granule, a wettable powder, a flowable, a microcapsule, an aerosol, a smoking pesticide, a poison bait, regious preparation and the like. These formulations can be converted to use into a poison bait, a sheet. In the noxious arthropod controlling composition of the present invention, the compound of the present invention is usually contained in an amount of 0.01% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea).

The liquid carrier for formulation includes, for example, water, alcohols (e.g., methanol, ethanol, isopropyl alcohol, butanol, hexanol, benzyl alcohol, ethylene glycol, propylene glycol, phenoxyethanol), ketones (e.g., acetone, methyl ethyl ketone, cyclohexanone), aromatic hydrocarbons (e.g., toluene, xylene, ethylbenzene, dodecylbenzene, phenylxylylethane, methylnaphthalene), aliphatic hydrocarbons (e.g., hexane, cyclohexane, kerosine, light oil), esters (e.g., ethyl acetate, butyl acetate, isopropyl mylistate, ethyl oleate, diisopropyl adipate, diisobutyl adipate, propyleneglycol monomethyl ether acetate), nitriles (e.g., acetonitrile, isobutyronitrile), ethers (e.g., diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol), acid amides (e.g., N,N-dimethylformamide, N,N-dimethylacetamide), halogenated hydrocarbons (e.g., dichloromethane, trichloroethane, tetrachlorocarbon), sulfoxides (e.g., dimethylsulfoxide), propylene carbonate, and vegetable oils (e.g., soy bean oil, cotton seed oil).

The gaseous carrier for formulation includes, for example, fluorocarbons, butane gas, liquefied petroleum gas (LPG), dimethyl ether, and carbon dioxide.

The surfactant for formulation includes, for example, nonionic surfactant, such as polyoxyethylene alkyl ether, polyoxyethylene alkylaryl ether, polyethyleneglycol fatty acid ester; anionic surfactant, such as alkylsulfonic acid salts, alkylbenzenesulfonic acid salts, alkylsurfic acid salts.

The other adjuvant for formulation includes, for example, binders, dispersants and stabilizers, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol).

The method for controlling noxious arthropod pests of the present invention is applying the compound of the present invention to pests directly and/or habitats of pests (e.g., plant, soil, indoor, in-body of animals, and so on). The compound of the present invention is usually used as an active ingredient of the noxious arthropod pests controlling composition.

When the noxious arthropod pests controlling composition of the present invention is used for a control of noxious arthropos pests in agriculture and forestry, the application amount is usually 0.01 to 10,000 g, preferablly 1 to 10,000 g, as an active ingredient per 10,000 m². In case of the noxious arthropod pests controlling compositions of the present invention are formulated to the emulsifiable concentrates, wettable powders and flowables, they are usually applied after dilution with water to have an active ingredient concentration of 0.01 to 10,000 ppm, while dusts and granules are usually applied as such. These preparations and the dilution of the preparation may be sprayed directly to the plant to be protected from pests. The pests living in a soil can be controlled by treating the soil with these preparations.

Furthermore, the reginous preparations of sheets or strip form can be applied by a method such as winding around plants, stretching in the vicinity of plants and laying on the soil surface at the plant bottom.

When the noxious arthropod pests controlling composition of the present invention is used for a control of noxious arthropod pests in indoor (e.g., fly, mesquite, cockroach), the application amount is usually 0.01 to 1,000 mg as the compound of the present invention per 1 $m^2$ in case of application for plane surface, and 0.01 to 500 mg as the compound of the present invention per 1 $m^3$ in case of application for open space.

In case of the noxious arthropod pests controlling composition of the present invention are formulated to the emulsifiable concentrate, wettable powders and flowables, they are usually applied after dilution with water to have an active ingredient concentration of 0.01 to 100,000 ppm, preferablly 0.1 to 1,000 ppm, while oil solutions, aerosols, smoking pesticides and poison baits are usually applied as such.

The noxious arthropod pests controlling composition of the present invention can contain other noxious arthropod pests controlling agents, nematocides, acaricides, fungicides, herbicides, plant growth regulators, synergists, fertilizers, soil conditioners, animal feeds, and the like.

The active ingredients of noxious arthropod pests controlling agents, nematocides, and/or acaricides include, for example, organophosphorus compounds such as Fenitrothion, Fenthion, Pyridaphenthion, Diazinon, Chlorpyriphos, Chlorpyriphos-methyl, Acephate, Methidathion, Disulfoton, DDVP, Sulprofos, Cyanophos, Dioxabenzofos, Dimethoate, Phenthoate, Malathion, Trichlorfon, Azinphosmethyl, Monocrotophos and Ethion; carbamate compounds such as BPMC, Benfuracarb, Propoxur, Carbosulfan, Carbaril, Methomyl, Ethiofencarb, Aldicarb, Oxamyl, Fenothiocarb, Thiodicarb, and Alanycarb; pyrethroid compounds such as Etofenprox, Fenvalerate, Esfenvalerate, Fenpropathrin, Cypermethrin, alfa-Cypermethrin, zeta-Cypermethrin, Permethrin, Cyhalothrin, lambda-Cyhalothrin, delta-Cyhalothrin, Cyfluthrin, beta-Cyfluthrin, Cycloprothrin, Fluvalinate, Flucythrinate, Bifenthrin, Acrinathrin, Traromethrin and Silafluofen; neonicotinoid compounds such as Acetamiprid, Nitenpyram, Thiamethoxiam, Thialoprid and Clothianidin; Nereistoxin derivatives such as Cartap, Thiocyclam, and Bensultap; chlorinated hydrocarbon compounds such as Endosul fan, gamma-BHC, and 1,1-bis(chlorophenyl)-2,2,2-trichloroethanol; benzoylphenylurea compounds such as Chlorfluazuron, Teflubenzuron, Fulphenoxron, and Lufenuron; phenylhydrazide compounds such as Tebufenozide, Chromafenozide, Methoxyfenozide and Halofenozide; formamidine derivatives such as Amitraz and Chlordimeform; thiourea derivatives such as Diafenthiuron; Buprofezin; Chlorfenapyr; Spinosad and derivatives thereof; Emamectin benzoate; Indoxacarb; Pymetrozine; phnylpyrazole derivatives; Bromopropylate; Tetradifon; Chinomethionat; Propargite; Fenbutatin oxide; Cyhexatin; Hexathiazox; Clofentezine; Pyridaben; Fenpyroximate; Tebufenpyrad; Pyrimidifen; Fenazaquin; Bifenazate; Acequinocyl; Spirodiclofen; Spiromesifen; polynactin complexes [e.g., tetranactin, dinactin, trinactin]; Milbemectin; Avermectin; Azadilactin; and Pyridalyl.

The present invention will be further illustrated by the following production examples, formulation examples, and test examples; however, the present invention is not limited to these examples.

The following describes the production examples for the present compounds.

PRODUCTION EXAMPLE 1

150 mg of the compound shown by the formula (i):

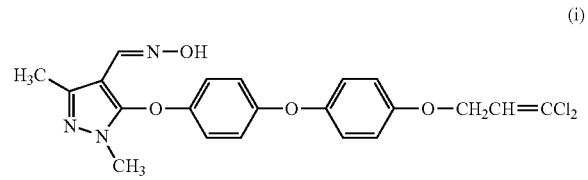

was dissolved in 5 ml of acetic anhydride, and the mixture was refluxed for one hour. After that, the reaction mixture which was cooled to room temperature was concentrated under reduced pressure, added water, and extracted with ethyl acetate. The organic layer was successively washed with water and saturated brine, dried over magnesium sulfate, and concentrated under reduced pressure. The residue was subjected to silica gel column chromatography to obtain 125 mg of the compound shown by the formula (1):

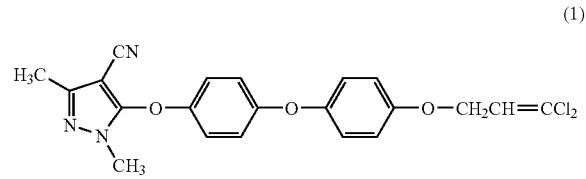

(hereinafter, referred as the present invention compound (1)).

$^1$H-NMR (CDCl$_3$, TMS) δ (ppm): 2.28 (3H, s), 3.71 (3H, s), 4.64 (2H, d), 6.16 (1H, t), 6.86-7.26 (8H, m)

PRODUCTION EXAMPLE 2

200 mg of the compound shown by the formula (ii):

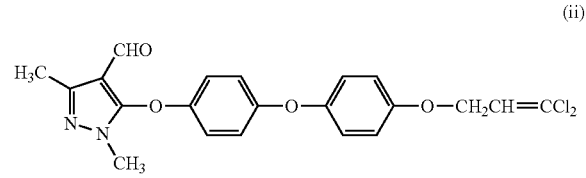

was dissolved in 3 ml of ethanol, 10 mg of sodium borohydride was added to the mixture, and the mixture was refluxed for one hour. After that, the reaction mixture which was cooled to room temperature was concentrated under reduced pressure, added water and 10% hydrochloric acid, and extracted with ethyl acetate. The organic layer was successively washed with water and saturated brine, dried over magnesium sulfate, and concentrated under reduced pressure. The residue was subjected to silica gel column chromatography to obtain 110 mg of the compound shown by the formula (2):

(2)

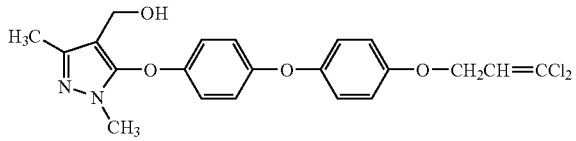

(hereinafter, referred as the present invention compound (2)).
¹H-NMR (CDCl₃, TMS) δ (ppm): 2.28 (3H, s), 3.60 (3H, s), 4.31 (2H, d), 4.63 (2H, d), 6.15 (1H, t), 6.84-6.95 (8H, m)

PRODUCTION EXAMPLE 3

200 mg of the compound shown by the formula (ii) was dissolved in 2 ml of methanol and 1 ml of trifluoroacetic acid, 350 mg of sodium borohydride was added to the mixture in ten portion s, and the mixture stirred at room temperature for one hour. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 150 mg of the compound shown by the formula (3):

(3)

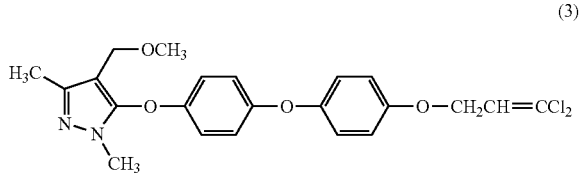

(hereinafter, referred as the present invention compound (3)).
¹H-NMR (CDCl₃, TMS) δ (ppm): 2.25 (3H, s), 3.20 (3H, s), 3.59 (3H, s), 4.06 (2H, s), 4.63 (2H, d), 6.16 (1H, t), 6.85-6.96 (8H, m)

PRODUCTION EXAMPLE 4

2.0 g of the compound shown by the formula (ii) was dissolved in 30 ml of ethanol, 260 mg of sodium borohydride was added to the mixture under ice-cooling, and the mixture was stirred for one hour. After that, dilute hydrochloric acid was added to the reaction mixture, stirred for 5 minutes, and concentrated under reduced pressure. Diluted hydrochloric acid was added to the residue, and extracted with ethyl acetate. The organic layer was successively washed with water and saturated brine, dried over magnesium sulfate, and concentrated under reduced pressure. The residue was subjected to silica gel column chromatography to obtain 340 mg of the compound shown by the formula (4):

(4)

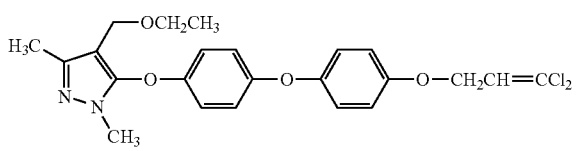

(hereinafter, referred as the present invention compound (4)).
¹H-NMR (CDCl₃, TMS) δ (ppm): 1.11 (3H, t), 2.24 (3H, s), 3.34 (2H, q), 3.59 (3H, s), 4.10 (2H, s), 4.63 (2H, d), 6.16 (1H, t), 6.84-6.95 (8H, m)

PRODUCTION EXAMPLE 5

100 mg of the compound shown by the formula (iii):

(iii)

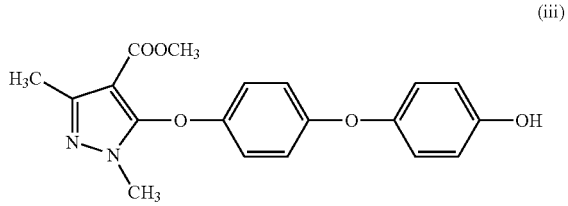

was dissolved in 2 ml of N,N-dimethylformamide, 60 mg of potassium carbonate and 60 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 120 mg of the compound shown by the formula (5):

(5)

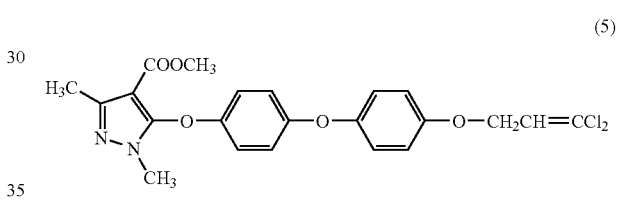

(hereinafter, referred as the present invention compound (5)).
¹H-NMR (CDCl₃, TMS) δ (ppm): 2.44 (3H, s), 3.63 (3H, s), 3.64 (3H, s), 4.63 (2H, d), 6.16 (1H, t), 6.83-6.95 (8H, m)

PRODUCTION EXAMPLE 6

110 mg of the compound shown by the formula (Iv):

(iv)

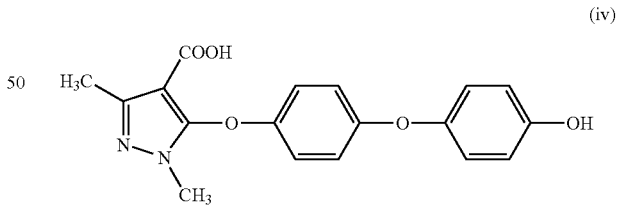

was dissolved in 2 ml of N,N-dimethylformamide, 110 mg of potassium carbonate and 70 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 100 mg of the compound shown by the formula (6):

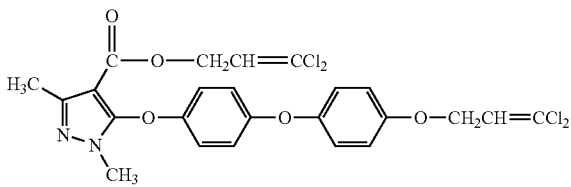
(6)

(hereinafter, referred as the present invention compound (6)).
$^1$H-NMR (CDCl$_{31}$, TMS) δ (ppm): 2.61 (3H, s), 3.71 (3H, s), 4.62 (2H, d), 4.64 (2H, d), 5.72 (1H, t), 6.16 (1H, t), 6.79-6.98 (8H, m)

PRODUCTION EXAMPLE 7

220 mg of the compound shown by the formula (v):

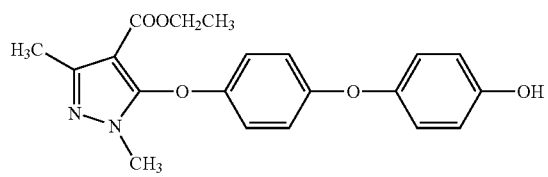
(v)

was dissolved in 2 ml of N,N-dimethylformamide, 100 mg of potassium carbonate and 100 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 260 mg of the compound shown by the formula (7):

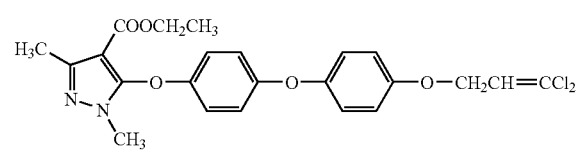
(7)

(hereinafter, referred as the present invention compound (7)).
$^1$H-NMR (CDCl$_3$, TMS)δ (ppm): 1.06 (3H, t), 2.45 (3H, s), 3.65 (3H, s), 4.09 (2H, q), 4.63 (2H, d), 6.16 (1H, s), 6.82-6.94 (8H, m)

PRODUCTION EXAMPLE 8

2.6 g of the compound shown by the formula (vi):

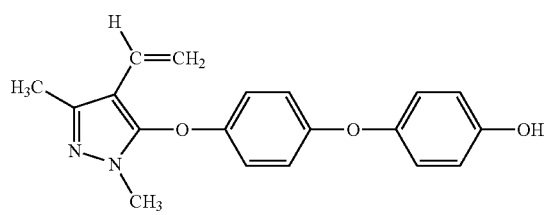
(vi)

was dissolved in 30 ml of N,N-dimethylformamide, 1.4 g of potassium carbonate and 1.4 g of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 3.5 g of the compound shown by the formula (8):

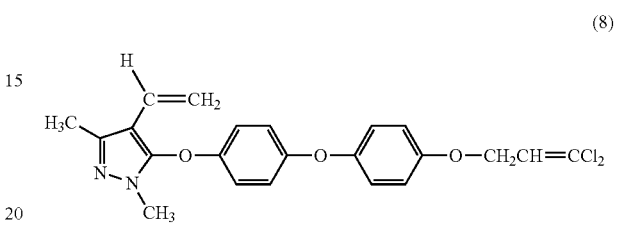
(8)

(hereinafter, referred as the present invention compound (8))
$^1$H-NMR (CDCl$_3$, TMS) δ (ppm): 2.31 (3H, s), 3.58 (3H, s), 4.63 (2H, d), 5.01 (1H, dd), 5.27 (1H, dd), 6.16 (1H, t), 6.32 (1H, dd), 6.83-6.95 (8H, m)

PRODUCTION EXAMPLE 9

130 mg of the compound shown by the formula (vii):

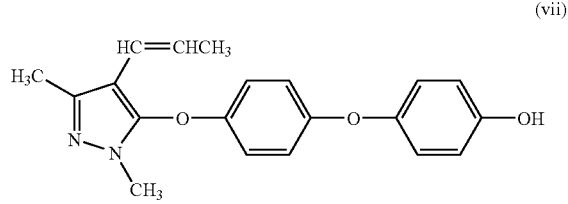
(vii)

was dissolved in 1 ml of N,N-dimethylformamide, 60 mg of potassium carbonate and 60 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 120 mg of the compound shown by the formula (9):

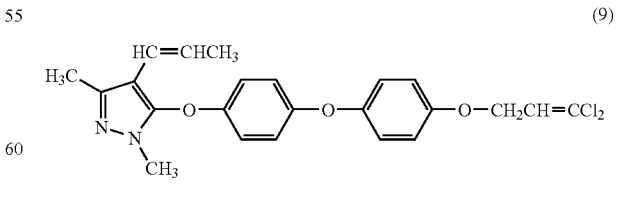
(9)

as a mixture of geometric isomers (hereinafter, referred as the present invention compound (9)).
$^1$H-NMR (CDCl$_3$, TMS) δ (ppm): 1.63 (1.5H, dd), 1.74 (1.5H, dd), 2.17 (1.5H, s), 2.28 (1.5H, s), 3.56 (1.5H, s), 3.62

(1.5H, s), 4.63 (1H, d), 4.63 (1H, d), 5.57 (0.5H, m), 5.78 (0.5H, m), 5.86 (0.5H, m), 5.98 (0.5H, m), 6.15 (1H, t), 6.79-6.95 (8H, m)

PRODUCTION EXAMPLE 10

By using 170 mg of the compound shown by the formula (viii):

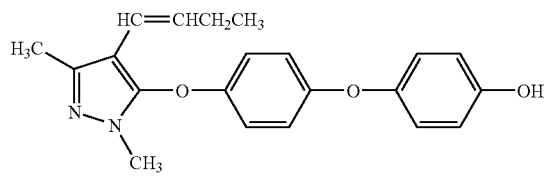

instead of the compound shown by the formula (vii), and 70 mg of potassium carbonate and 80 mg of 1,1,3-trichloropropene, according to the similar method described in Production Example 9 was obtained 160 mg of the compound shown by the formula (10):

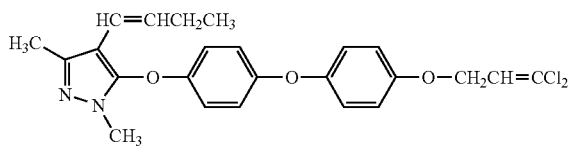

as a mixture of geometric isomers (hereinafter, referred as the present invention compound (10)).

$^1$H-NMR (CDCl$_3$, TMS) δ (ppm): 0.92 (3H, m), 2.05 (2H, m), 2.17 (2.1H, s), 2.28 (0.9H, s), 3.57 (0.9H, s), 3.61 (2.1H, s), 4.63 (2H, d), 5.45 (0.7H, m), 5.78 (1H, m), 5.95 (0.3H, m), 6.15 (1H, t), 6.78-6.94 (8H, m)

PRODUCTION EXAMPLE 11

By using 110 mg of the compound shown by the formula (1x):

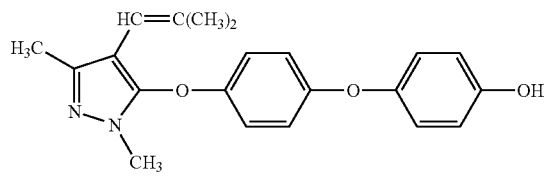

instead of the compound shown by the formula (vii), and 50 mg of potassium carbonate and 60 mg of 1,1,3-trichloropropene, according to the similar method described in Production Example 9 was obtained 90 mg of the compound shown by the formula (11):

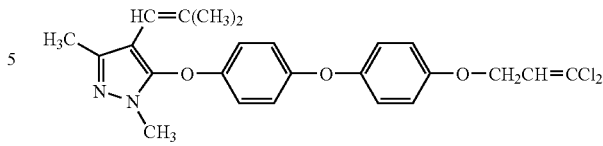

(hereinafter, referred as the present invention compound (11)).

$^1$H-NMR (CDCl$_3$, TMS) δ (ppm): 1.60 (3H, d), 1.72 (3H, d), 2.14 (3H, s), 3.61 (3H, s), 4.63 (2H, d), 5.59 (1H, m), 6.15 (1H, t), 6.78-6.94 (8H, m)

PRODUCTION EXAMPLE 12

By using 140 mg of the compound shown by the formula (x):

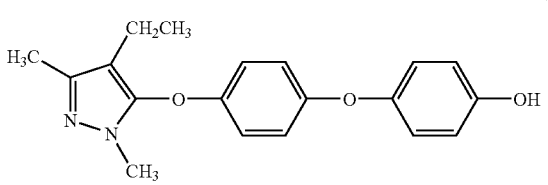

instead of the compound shown by the formula (vii), and 70 mg of potassium carbonate and 70 mg of 1,1,3-trichloropropene, according to the similar method described in Production Example 9 was obtained 160 mg of the compound shown by the formula (12):

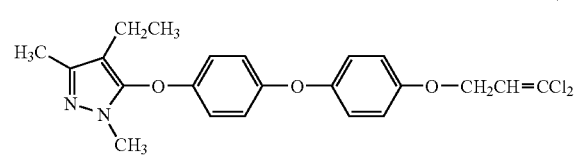

(hereinafter, referred as the present invention compound (12)).

$^1$H-NMR (CDCl$_3$, TMS) (ppm): 0.99 (3H, t), 2.20 (3H, s), 2.22 (2H, q), 3.56 (3H, s), 4.64 (2H, d), 6.16 (1H, t), 6.82-6.95 (8H, m)

PRODUCTION EXAMPLE 13

By using 180 mg of the compound shown by the formula (xi):

instead of the compound shown by the formula (vii), and 90 mg of potassium carbonate and 100 mg of 1,1,3-trichloropropene, according to the similar method described in Production Example 9 was obtained 210 mg of the compound shown by the formula (13):

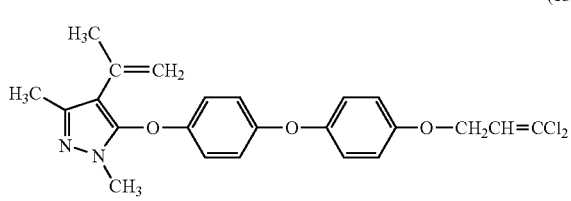

(13)

(hereinafter, referred as the present invention compound (13)).

$^1$H-NMR (CDCl$_3$, TMS) δ (ppm): 1.92 (3H, m), 2.31 (3H, s), 3.56 (3H, s), 4.63 (2H, d), 4.94 (1H, m), 4.96 (1H, m), 6.15 (1H, t), 6.79-6.95 (8H, m)

PRODUCTION EXAMPLE 14

260 mg of the compound shown by the formula (vi) was dissolved in 2 ml of N,N-dimethylformamide, 130 mg of potassium carbonate and 110 mg of 1,3-dichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 300 mg of the compound shown by the formula (14):

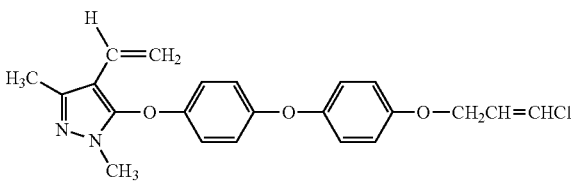

(14)

as a mixture of geometric isomers (hereinafter, referred as the present invention compound (14)).

$^1$H-NMR (CDCl$_3$, TMS) δ (ppm): 2.31 (3H, s), 3.58 (3H, s), 4.49 (1H, dd), 4.74 (1H, dd), 5.01 (1H, dd), 5.27 (1H, dd), 6.03-6.39 (3H, m), 6.82-6.95 (8H, m)

PRODUCTION EXAMPLE 15

0.42 ml of lithium diisopropylamide (2.0 mol/L heptane-tetrahydrofuran-ethylbenzene solution) was added to 870 mg of hexane solution which contained 10% trimethyl silyldiazomethane at −78° C., and the mixture was stirred at same temperature for two hours. After that, 300 mg of the compound shown by the formula (ii) was added to the mixture at −78° C. with stirring, and the mixture was warmed to 0° C. over 3 hours with stirring. After that, saturated aqueous solution of ammonium chloride was added to the reaction mixture, and extracted with ethyl acetate. The organic layer was successively washed with diluted hydrochloric acid, water and saturated brine; dried over magnesium sulfate; and concentrated under reduced pressure. The residue was subjected to silica gel column chromatography to obtain 260 mg of the compound shown by the formula (15):

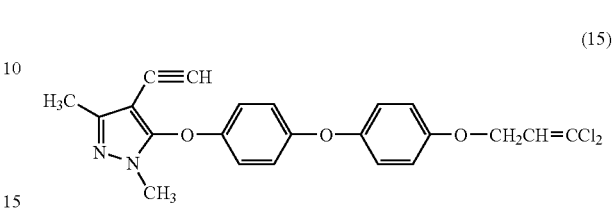

(15)

(hereinafter, referred as the present invention compound (15)).

$^1$H-NMR (CDCl$_3$, TMS) δ (ppm): 2.26 (3H, s), 2.99 (1H, s), 3.64 (3H, s), 4.64 (2H, d), 6.16 (1H, t), 6.85-7.01 (8H, m)

PRODUCTION EXAMPLE 16

180 mg of the compound shown by the formula (xiv):

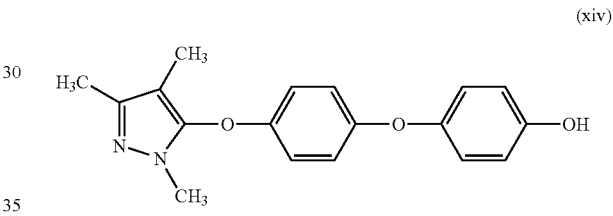

(xiv)

was dissolved in 2 ml of N,N-dimethylformamide, 100 mg of potassium carbonate and 100 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 220 mg of the compound shown by the formula (16):

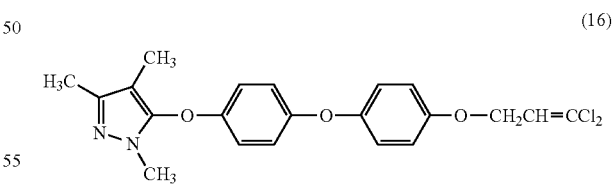

(16)

(hereinafter, referred as the present invention compound (16))

$^1$H-NMR (CDCl$_3$, TMS) δ (ppm): 1.75 (3H, s), 2.17 (3H, s), 3.58 (3H, s), 4.63 (2H, d), 6.16 (1H, t), 6.82-6.99 (8H, m)

PRODUCTION EXAMPLE 17

0.12 ml of lithium diisopropylamide (2.0 mol/L heptane-tetrahydrofuran-ethylbenzene solution) was added to 0.12 ml of hexane solution of trimethylsilyldiazomethane (2.0 mol/L)

at −78° C., and the mixture was stirred at same temperature for one hour. After that, 90 mg of the compound shown by the formula (xv):

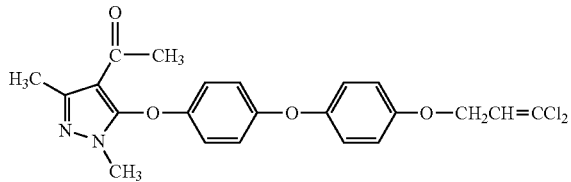

was added to the mixture at −78° C. with stirring, and the mixture was warmed to 0° C. over 30 minutes with stirring, and stirred for two hours at 0° C. After that, saturated aqueous solution of ammonium chloride was added to the reaction mixture, and extracted with ethyl acetate. The organic layer was successively washed with diluted hydrochloric acid, water and saturated brine; dried over magnesium sulfate; and concentrated under reduced pressure. The residue was subjected to silica gel column chromatography to obtain 40 mg of the compound shown by the formula (17):

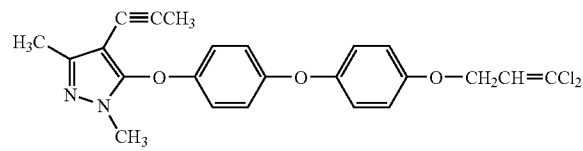

(hereinafter, referred as the present invention compound (17)).

$^1$H-NMR (CDCl$_3$, TMS) δ (ppm): 1.88 (3H, s), 2.23 (3H, s), 3.61 (3H, s), 4.64 (2H, d), 6.16 (1H, t), 6.81-7.00 (8H, m)

PRODUCTION EXAMPLE 18

100 mg of the compound shown by the formula (xvi):

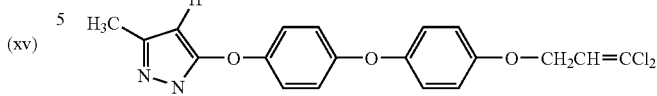

was dissolved in 2 ml of N,N-dimethylformamide, 60 mg of potassium carbonate and 60 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 130 mg of the compound shown by the formula (18):

(hereinafter, referred as the present invention compound (18))

$^1$H-NMR (CDCl$_3$, TMS) δ (ppm): 2.19 (3H, s), 3.67 (3H, s), 4.65 (2H, d), 5.37 (1H, s), 6.16 (1H, t), 6.86-7.06 (8H, m)

PRODUCTION EXAMPLE 19

By using 200 mg of the compound shown by the formula (xvii):

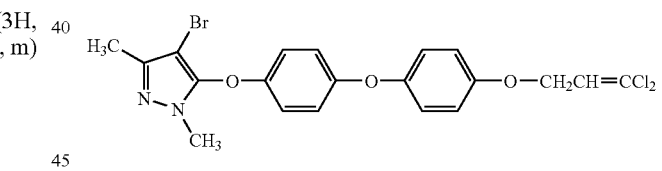

instead of the compound shown by the formula (xvi), and 90 mg of potassium carbonate, 90 mg of 1,1,3-trichloropropene and 2 ml of N,N-dimethylformamide, according to the similar method described in Production Example 18 was obtained 260 mg of the compound shown by the formula (19):

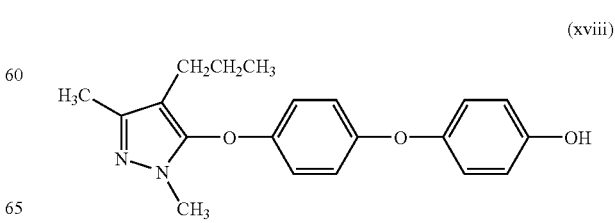

(hereinafter, referred as the present invention compound (19)).

$^1$H-NMR (CDCl$_3$, TMS) δ (ppm): 2.22 (3H, s), 3.65 (3H, s), 4.64 (2H, d), 6.16 (1H, t), 6.84-6.99 (8H, m)

PRODUCTION EXAMPLE 20

By using 400 mg of the compound shown by the formula (xviii):

instead of the compound shown by the formula (xvi), and 200 mg of potassium carbonate, 210 mg of 1,1,3-trichloropropene and 5 ml of N,N-dimethylformamide, according to the similar method described in Production Example 18 was obtained 490 mg of the compound shown by the formula (20):

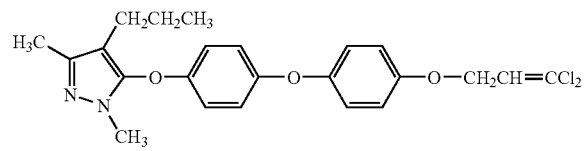

(20)

(hereinafter, referred as the present invention compound (20)).

$^1$H-NMR (CDCl$_3$, TMS) δ (ppm): 0.84 (3H, t), 1.40 (2H, m), 2.16 (2H, t), 2.19 (3H, s), 3.56 (3H, s), 4.63 (2H, d), 6.16 (1H, t), 6.80-6.96 (8H, m)

PRODUCTION EXAMPLE 21

By using 140 mg of the compound shown by the formula (xix):

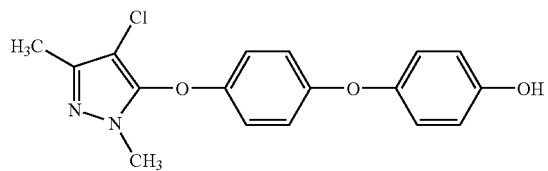

(xix)

instead of the compound shown by the formula (xvi), and 70 mg of potassium carbonate, 70 mg of 1,1,3-trichloropropene and 2 ml of N,N-dimethylformamide, according to the similar method described in Production Example 18 was obtained 140 mg of the compound shown by the formula (21):

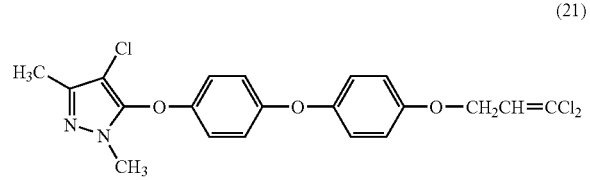

(21)

(hereinafter, referred as the present invention compound (21)).

$^1$H-NMR (CDCl$_3$, TMS) δ (ppm): 2.22 (3H, s), 3.63 (3H, s), 4.64 (2H, d), 6.16 (1H, t), 6.84-6.97 (8H, m)

PRODUCTION EXAMPLE 22

By using 120 mg of the compound shown by the formula (xx):

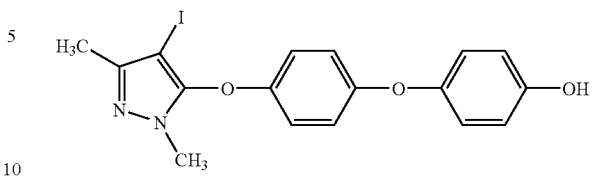

(xx)

instead of the compound shown by the formula (xvi), and 50 mg of potassium carbonate, 50 mg of 1,1,3-trichloropropene and 2 ml of N,N-dimethylformamide according to the similar method described in Production Example 18 was obtained 130 mg of the compound shown by the formula (22):

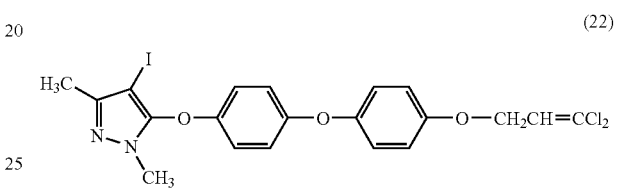

(22)

(hereinafter, referred as the present invention compound (22)).

$^1$H-NMR (CDCl$_3$, TMS) δ (ppm): 2.23 (3H, s), 3.67 (3H, s), 4.64 (2H, d), 6.16 (1H, t), 6.83-6.99 (8H, m)

PRODUCTION EXAMPLE 23

500 mg of the compound shown by the formula (ii) was dissolved 5 ml of chloroform, 400 mg of (dimethylamino)sulfur trifluoride was added to the mixture under ice cooling, and the mixture was stirred at room temperature for ten hours. After that, saturated aqueous solution of sodium hydrogen carbonate was added to the reaction mixture, and extracted with ethylacetate. The organic layer was washed with saturated brine, dried over magnesium sulfate, and concentrated-under reduced pressure. The residue was subjected to silica gel column chromatography to obtain 60 mg of the compound shown by the formula (23):

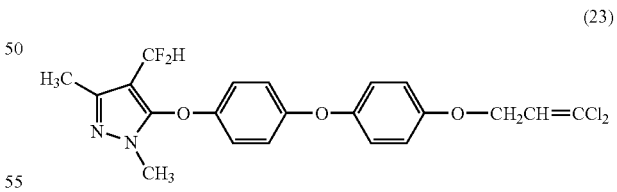

(23)

(hereinafter, referred as the present invention compound (23)).

$^1$H-NMR (CDCl$_3$, TMS)δ (ppm): 2.34 (3H, s), 3.59 (3H, s), 4.64 (2H, d), 6.16 (1H, t), 6.37 (1H, t), 6.85-6.98 (8H, m)

PRODUCTION EXAMPLE 24

200 mg of the compound shown by the formula (xiv) was dissolved in 2 ml of N,N-dimethylformamide, 110 mg of potassium carbonate and 120 mg of 1,3-dichloro-1-butene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 230 mg of the compound shown by the formula (24):

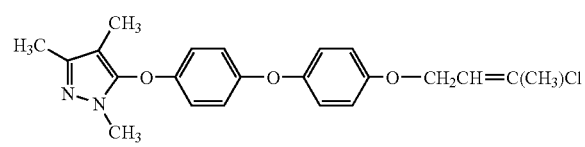

(24)

as a mixture of geometric isomers (hereinafter, referred as the present invention compound (24)).

$^1$H-NMR (CDCl$_3$, TMS) δ (ppm): 1.75 (3H, s), 2.17 (6H, m), 3.58 (3H, s), 4.49 (0.4H, m), 4.66 (1.6H, m), 5.76 (0.8H, m), 5.93 (0.2H, m), 6.81-6.95 (8H, m)

PRODUCTION EXAMPLE 25

150 mg of the compound shown by the formula (xiv) was dissolved in 2 ml of N,N-dimethylformamide, 50 mg of potassium carbonate and 40 mg of 3-chloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 150 mg of the compound shown by the formula (25):

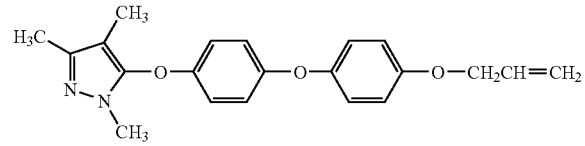

(25)

(hereinafter, referred as the present invention compound (25)).

$^1$H-NMR (CDCl$_3$, TMS) δ (ppm): 1.75 (3H, s), 2.17 (3H, s), 3.58 (3H, s), 4.51 (2H, m), 5.35 (2H, m), 6.05 (1H, m), 6.81-6.95 (8H, m)

PRODUCTION EXAMPLE 26

180 mg of the compound shown by the formula (xiv) was dissolved in 3 ml of N,N-dimethylformamide, 100 mg of potassium carbonate and 80 mg of 1-chloro-3-methyl-2-butene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 210 mg of the compound shown by the formula (26):

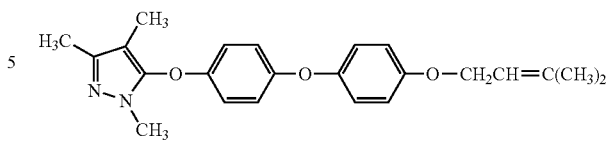

(26)

(hereinafter, referred as the present invention compound (26))

$^1$H-NMR (CDCl$_3$, TMS) δ (ppm): 11.75 (6H, m), 1.80 (3H, m), 2.17 (3H, s), 3.58 (3H, s), 4.48 (2H, d), 5.49 (1H, m), 6.80-6.99 (8H, m)

PRODUCTION EXAMPLE 27

190 mg of the compound shown by the formula (xxi):

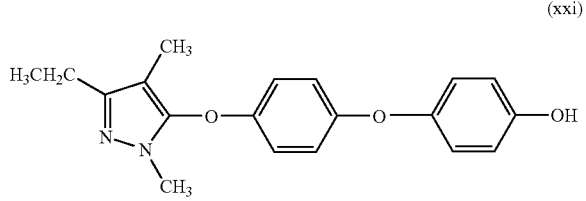

(xxi)

was dissolved in 2 ml of N,N-dimethylformamide, 100 mg of potassium carbonate and 100 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 200 mg of the compound shown by the formula (27):

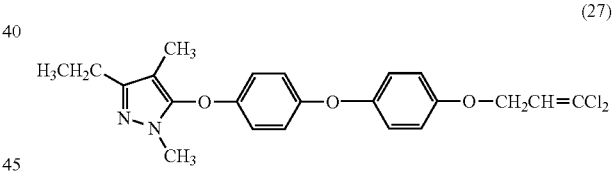

(27)

(hereinafter, referred as the present invention compound (27)).

$^1$H-NMR (CDCl$_3$, TMS) δ (ppm): 1.23 (3H, t), 1.77 (3H, s), 2.56 (2H, q), 3.59 (3H, s), 4.64 (2H, d), 6.16 (1H, t), 6.83-6.96 (8H, m)

PRODUCTION EXAMPLE 28

140 mg of the compound shown by the formula (xxii):

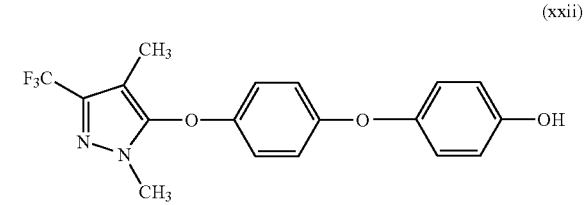

(xxii)

was dissolved in 2 ml of N,N-dimethylformamide, 70 mg of potassium carbonate and 70 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 170 mg of the compound shown by the formula (28):

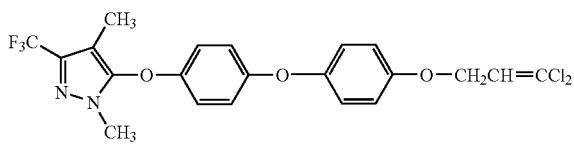

(28)

(hereinafter, referred as the present invention compound (28)).

$^1$H-NMR (CDCl$_3$, TMS) δ (ppm): 1.91 (3H, s), 3.70 (3H, s), 4.64 (2H, d), 6.16 (1H, t), 6.83-6.96 (8H, m)

PRODUCTION EXAMPLE 29

120 mg of the compound shown by the formula (xxiii):

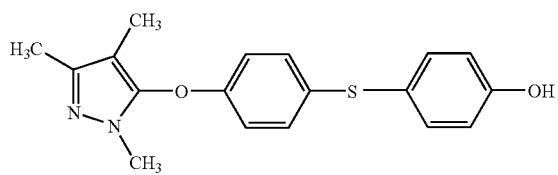

(xxiii)

was dissolved in 2 ml of N,N-dimethylformamide, 70 mg of potassium carbonate and 70 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 160 mg of the compound shown by the formula (29):

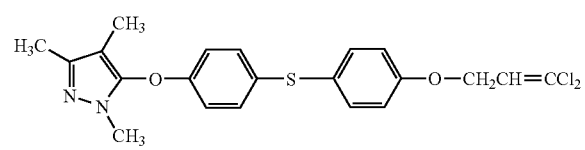

(29)

(hereinafter, referred as the present invention compound (29)).

$^1$H-NMR (CDCl$_3$, TMS) δ (ppm): 1.74 (3H, s), 2.17 (3H, s), 3.55 (3H, s), 4.65 (2H, d), 6.15 (1H, t), 6.78-6.87 (4H, m), 7.19-7.23 (2H, m), 7.32-7.36 (2H, m)

PRODUCTION EXAMPLE 30

140 mg of the compound shown by the formula (xxiv):

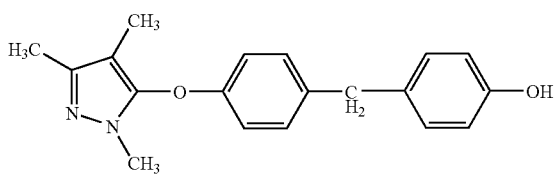

(xxiv)

was dissolved in 2 ml of N,N-dimethylformamide, 80 mg of potassium carbonate and 80 mg of 1,1,3-trichloropropene were added to the mixture, and the mixture was stirred at room temperature for ten hours. After that, the reaction mixture was added to dilute hydrochloric acid, and extracted with ethyl acetate. The organic layer was successively washed with water and saturated brine, dried over magnesium sulfate, and concentrated under reduced pressure. The residue was subjected to silica gel column chromatography to obtain 160 mg of the compound shown by the formula (30):

(30)

(hereinafter, referred as the present invention compound (30)).

$^1$H-NMR (CDCl$_3$, TMS) δ (ppm): 1.73 (3H, s), 2.17 (3H, s), 3.55 (3H, s), 3.87 (2H, s), 4.63 (2H, d), 6.15 (1H, t), 6.78-6.83 (4H, m), 7.07-7.11 (4H, m)

Next, the compound which was used to produce the compound of the present invention describes the reference production examples. Some of these reference production examples are also the production example of the intermediate compound of the present invention.

REFERENCE PRODUCTION EXAMPLE 1

200 mg of the compound shown by the formula (xii):

(xii)

was dissolved in 3 ml of N,N-dimethylformamide, 100 mg of potassium carbonate and 100 mg of 1,1,3-trichloropropene were added to the mixture, and the mixture was stirred at 70° c. for one hour. After that, water and 10% hydrochloric acid were added to the reaction mixture which was cooled to room temperature, and extracted with ethyl acetate. The organic layer was successively washed with water and saturated brine, dried over magnesium sulfate, and concentrated under reduced pressure. The residue was subjected to silica gel column chromatography to obtain 190 mg of the compound shown by the formula (ii).

$^1$H-NMR (CDCl$_3$, TMS) δ (ppm): 2.45 (3H, s), 3.66 (3H, s), 4.64 (2H, d), 6.16 (1H, t), 6.83-6.97 (8H, m), 9.51 (1H, s)

REFERENCE PRODUCTION EXAMPLE 2

300 mg of 4,4'-dihydroxybiphenylether shown by the formula:

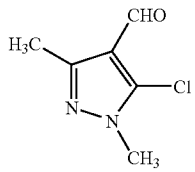

was dissolved in 5 ml of N,N-dimethylformamide, 120 mg of sodium hydride (60% in oil) ice-cooling under ice cooling, and was stirred at room temperature for ten minutes. After that, to the said mixture was added 3 ml of N,N-dimethylformamide solution of 230 mg of 5-chloro-1,3-dimethyl-1H-pyrazole-4-carbaldehyde shown by the formula:

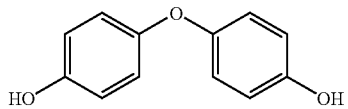

over ten minutes at 70° C., and then the mixture was stirred at 70° C. for two hours. After that, water and 10% hydrochloric acid were added to the reaction mixture which was cooled to room temperature, and extracted with ethyl acetate. The organic layer was successively washed with water and saturated brine, dried over magnesium sulfate, and concentrated under reduced pressure. The residue was subjected to silica gel column chromatography to obtain 260 mg of the compound shown by the formula (xii).

$^1$H-NMR (CDCl$_3$ TMS) δ (ppm): 2.45 (3H, s), 3.66 (3H, s), 5.44 (1H, br), 6.76-6.99 (8H, m), 9.50 (1H, s)

REFERENCE PRODUCTION EXAMPLE 3

2.0 g of the compound shown by the formula (ii) was dissolved in 3 ml of pyridine, 0.35 g of hydroxylamine hydrochloride was added to the mixture under ice cooling, and then the mixture stirred thirty minutes at room temperature. After that, the reaction mixture was concentrated under reduced pressure. Water and 10% hydrocloric acid were added to the residue, and was extracted with ethyl acetate. The organic layer was successively washed with water and saturated brine, dried over magnesium sulfate, and concentrated under reduced pressure. The residue was subjected to silica gel column chromatography to obtain 2.0 g of the compound shown by the formula (i).

$^1$H-NMR (CDCl$_3$, TMS) δ (ppm): 2.36 (3H, s), 3.61 (3H, s), 4.64 (2H, d), 6.16 (1H, t), 6.84-6.96 (8H, m), 7.08 (1H, s), 7.83 (1H, s)

REFERENCE PRODUCTION EXAMPLE 4

0.19 g of sodium hydride (55% in oil) was suspended to 10 ml of N,N-dimethylformaide, and 1.03 g of 4,4'-dihydroxybiphenylether was added to the suspension under ice-cooling, and the mixture was stirred at 70° C. for thirty minutes. After that, to the said mixture was added 5 ml of N,N-dimethylformamide solution of 0.64 g of 5-chloro-1,3-dimethyl-1H-pyrazole-4-carboxylic acid methyl ester shown by the formula:

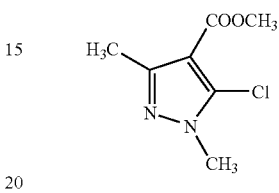

over thirty minutes at 70° C., and then the mixture was stirred at 70° C. for ten hours. After that, saturated aqueous solution of ammonium chloride was added to the reaction mixture which was cooled to room temperature, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 0.19 g of the compound shown by the formula (iii).

$^1$H-NMR (CDCl$_3$, TMS) δ (ppm): 2.44 (3H, s), 3.63 (3H, s), 3.64 (3H, s), 4.91 (1H, br), 6.79-6.91 (8H, m)

REFERENCE PRODUCTION EXAMPLE 5

130 mg of the compound shown by the formula (iii) was dissolved to 3 ml of toluene, and 2 ml of aqueous solution of sodium hydroxide (1 mole/L) was added to the mixture, and the mixture was stirred at 80° C. for two hours. After that, the reaction mixture was cooled to room temperature, toluene was added to the reaction mixture, and extracted with aqueous solution of sodium hydroxide (1 mole/L). The aqueous layer was acidified by adding concentrated hydrochloric acid, and extracted by ethyl acetate. The organic layer was successively washed with diluted hydrochloric acid, water and saturated brine, dried over magnesium sulfate, and concentrated under reduced pressure, to obtain 110 mg of the compound shown by the formula (Iv).

$^1$H-NMR ((CD$_3$)$_2$SO, TMS) δ (ppm): 2.29 (3H, s), 3.52 (3H, s), 6.71-6.87 (8H, m), 9.34 (1H, br)

REFERENCE PRODUCTION EXAMPLE 6

0.43 g of sodium hydride (55% in oil) was suspended to 10 ml of N,N-dimethylformaide, and 1.57 g of 4,4'-dihydroxybiphenylether was added to the suspension under ice-cooling, and the mixture was stirred at 70° C. for thirty minutes. After that, to the said mixture was added 5 ml of N,N-dimethylformamide solution of 1.43 g of 5-chloro-1,3-dimethyl-1H-pyrazole-4-carboxylic acid ethyl ester shown by the formula:

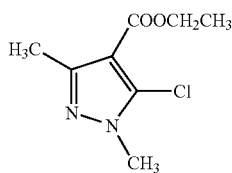

over thirty minutes at 70° C., and then the mixture was stirred at 70° C. for ten hours. After that, saturated aqueous solution of ammonium chloride was added to the reaction mixture which was cooled to room temperature, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 0.85 g of the compound shown by the formula (v).

$^1$H-NMR (CDCl$_3$, TMS) δ (ppm): 1.07 (3H, t), 2.46 (3H, s), 3.65 (3H, s), 4.10 (2H, q), 6.44 (1H, br), 6.76-6.91 (8H, m)

REFERENCE PRODUCTION EXAMPLE 7

2.2 g of methyltriphenylphosphonium bromide was suspended to 5 ml of tetrahydrofuran, 3.9 ml of hexane solution of normal butyllithium (1.58 mole/L) was dropped to the suspension, and then the mixture was stirred at room temperature for thirty minutes. 1.0 g of the compound shown by the formula (xii) was added to the mixture, and then refluxed for one hour. After that, saturated aqueous solution of ammonium chloride was added to the reaction mixture which was cooled to room temperature, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 0.9 g of the compound shown by the formula (vi).

$^1$H-NMR (CDCl$_3$, TMS) δ (ppm): 2.31 (3H, s), 3.58 (3H, s), 5.03 (1H, dd), 5.28 (1H, dd), 6.02 (1H, br), 6.32 (1H, dd), 6.77-6.92 (8H, m)

REFERENCE PRODUCTION EXAMPLE 8

230 mg of ethyltriphenylphosphonium bromide was dissolved to 1 ml of tetrahydrofuran, 0.8 ml of hexane solution of normal butyllithium (1.58 mole/L) was dropped to the solution, and then the mixture was stirred at room temperature for thirty minutes. 100 mg of the compound shown by the formula (xii) was added to the mixture, and then stirred at room temperature for three hours. After that, saturated aqueous solution of ammonium chloride was added to the reaction mixture, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 130 mg of the compound shown by the formula (vii) as mixture of geometric isomers.

$^1$H-NMR (CDCl$_3$, TMS) δ (ppm): 1.63 (1.5H, dd), 1.73 (1.5H, dd), 2.17 (1.5H, s), 2.28 (1.5H, s), 3.55 (1.5H, s), 3.62 (1.5H, s), 5.58 (0.5H, m), 5.78 (0.5H, m), 5.86 (0.5H, m), 5.98 (0.5H, m), 6.77-6.90 (8H, m)

REFERENCE PRODUCTION EXAMPLE 9

260 mg of propyltriphenylphosphonium bromide was suspended to 1 ml of tetrahydrofuran, 0.6 ml of hexane solution of normal butyllithium (1.58 mole/L) was dropped to the solution, and then the mixture was stirred at room temperature for thirty minutes. 150 mg of the compound shown by the formula (xii) was added to the mixture, and then stirred at room temperature for three hours. After that, saturated aqueous solution of ammonium chloride was added to the reaction mixture, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 170 mg of the compound shown by the formula (viii) as mixture of geometric isomers.

$^1$H-NMR (CDCl$_3$, TMS) δ (ppm): 0.93 (3H, m), 2.04 (2H, m), 2.17 (2.1H, s), 2.28 (0.9H, s), 3.57 (0.9H, s), 3.61 (2.1H, s), 5.45 (0.7H, m), 5.78 (1H, m), 5.9 (0.3H, m), 6.76-6.94 (8H, m)

REFERENCE PRODUCTION EXAMPLE 10

400 mg of isopropyltriphenylphosphonium iodide was suspended to 2 ml of tetrahydrofuran, 0.6 ml of hexane solution of normal butyllithium (1.58 mole/L) was dropped to the solution, and then the mixture was stirred at room temperature for thirty minutes. 150 mg of the compound shown by the formula (xii) was added to the mixture, and then stirred at room temperature for three hours. After that, saturated aqueous solution of ammonium chloride was added to the reaction mixture, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 110 mg of the compound shown by the formula (1x).

$^1$H-NMR (CDCl$_3$, TMS) δ (ppm): 1.60 (3H, d), 1.71 (3H, d), 2.14 (3H, s), 3.60 (3H, s), 5.59 (1H, m), 6.76-6.94 (8H, m)

REFERENCE PRODUCTION EXAMPLE 11

The compound shown by the formula (vi) was dissolved to 15 ml of methanol, to the solution was added 20 mg of 10% palladium-carbon, and then the mixture was stirred vigorously under hydrogen atmosphere at room temperature for six hours. After that, ethyl acetate was added to the reaction mixture, and was filtered. Filtrate was concentrated under reduced pressure to obtain 790 mg of the compound shown by the formula (x).

$^1$H-NMR (CDCl$_3$, TMS) δ (ppm): 0.99 (3H, t), 2.21 (3H, s), 2.23 (2H, q), 3.56 (3H, s), 6.77-6.91 (8H, m)

REFERENCE PRODUCTION EXAMPLE 12

470 mg of methyltriphenylphosphonium bromide was suspended to 2 ml of tetrahydrofuran, 2.5 ml of hexane solution of normal butyllithium (1.58 mole/L) was dropped to the suspension, and then the mixture was stirred at room temperature for one hour. 200 mg of the compound shown by the formula (xiii):

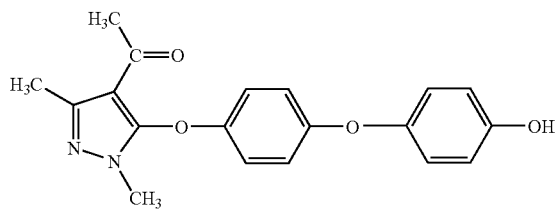

(xiii)

was added to the mixture, and then refluxed for four hours. After that, saturated aqueous solution of ammonium chloride was added to the reaction mixture which was cooled to room temperature, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 180 mg of the compound shown by the formula (xi).

$^1$H-NMR (CDCl$_3$, TMS) δ (ppm): 1.92 (3H, m), 2.31 (3H, s), 3.56 (3H, s), 4.78 (1H, s), 4.94 (1H, m), 4.96 (1H, m), 6.79-6.90 (8H, m)

REFERENCE PRODUCTION EXAMPLE 13

560 mg of 4,4'-dihydroxybiphenylether was dissolved to 10 ml of N,N-dimethylformaide, 140 mg of sodium hydride (60% in oil) was added to the solution under ice-cooling, and then the mixture was stirred at 70° C. for one hour. After that, to the said mixture was added 5 ml of N,N-dimethylformamide solution of 400 mg of 1-(5-chloro-1,3-dimethyl-1H-pyrazo-4-yl)ethanone shown by the formula:

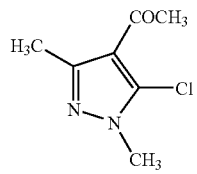

over fifteen minutes at 70° C., and then the mixture was stirred at 70° C. for six hours. After that, diluted hydrochloric acid was added to the reaction mixture which was cooled to room temperature, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 340 mg of the compound shown by the formula (xiii).

$^1$H-NMR (CDCl$_3$, TMS) δ (ppm): 2.26 (3H, s), 2.47 (3H, s), 3.57 (3H, s), 5.22 (1H, s), 6.79-6.95 (8H, m)

REFERENCE PRODUCTION EXAMPLE 14

3.0 g of the compound shown by the formula (xii):

(xii)

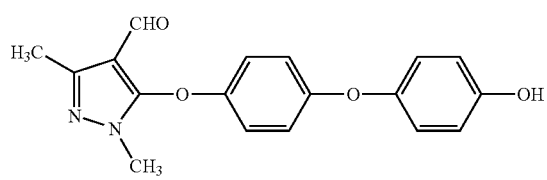

was dissolved to 30 ml of di (ethylene glycol), 0.51 g of hydrazine hydrate and 1.1 g of potassium hydroxide were added, and then stirred at 80° C. for one hour, and at 180° C. for one hour. After that, the reaction mixture which was cooled to room temperature was acidified by adding diluted hydrochloric acid, and extracted by ethyl acetate. The organic layer was successively washed with water and saturated brine, dried over magnesium sulfate, and concentrated under reduced pressure. The residue was subjected to silica gel column chromatography to obtain 1.9 g of the compound shown by the formula (xiv).

(xiv)

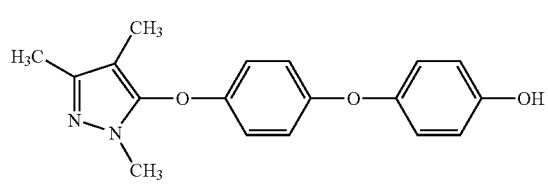

$^1$H-NMR (CDCl$_3$, TMS) δ (ppm): 1.75 (3H, s), 2.18 (3H, s), 3.58 (3H, s), 6.27 (1H, br), 6.80-6.90 (8H, m)

REFERENCE PRODUCTION EXAMPLE 15

270 mg of the compound shown by the formula (xiii):

(xiii)

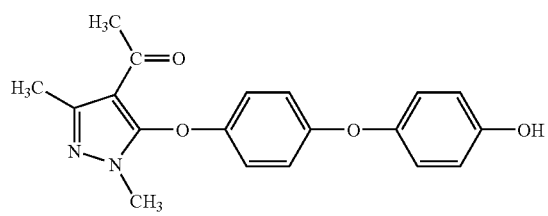

was dissolved in 2 ml of N,N-dimethylformamide, 150 mg of potassium carbonate and 140 mg of 1,1,3-trichloropropene were added to the mixture, and the mixture was stirred at room temperature for ten hours. After that, diluted hydrochloric acid was added to the reaction mixture, and extracted with ethyl acetate. The organic layer was successively washed with water and saturated brine, dried over magnesium sulfate, and concentrated under reduced pressure. The residue was subjected to silica gel column chromatography to obtain 350 mg of the compound shown by the formula (xv).

(xv)

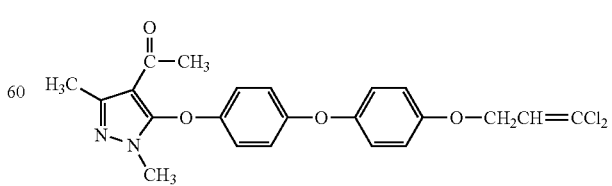

$^1$H-NMR (CDCl$_3$, TMS) δ (ppm): 2.25 (3H, s), 2.47 (3H, s), 3.57 (3H, s), 4.64 (2H, d), 6.16 (1H, t), 6.81-6.97 (8H, m)

REFERENCE PRODUCTION EXAMPLE 16

1.5 g of the compound shown by the formula (v):

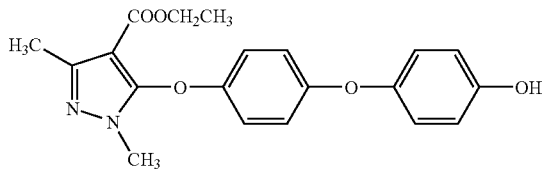

(v)

was suspended to 15 ml of toluene. The suspension was dissolved at 80° C., 12 ml of aqueous solution of sodium hydroxide (1 mole/L) was added to the solution, and the mixture refluxed for two hours. After that the reaction mixture was cooled to room temperature, standed and separated to two phase. To the aqueous layer, 10 ml of water was added, and then 15 ml of concentrated hydrochloric acid was added. 15 ml of toluene was added to the mixture and refluxed for seven hours. The mixture was cooled to room temperature, and extracted with ethyl acetate. The organic layer was successively washed with water and saturated brine, dried over magnesium sulfate, and concentrated under reduced pressure. The residue was subjected to silica gel column chromatography to obtain 1.1 g of the compound shown by the formula (xvi).

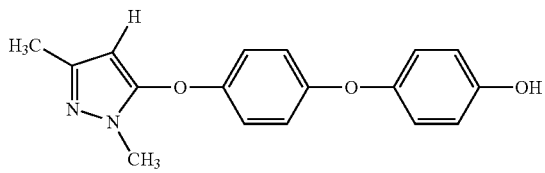

(xvi)

$^1$H-NMR (CDCl$_3$, TMS) δ (ppm): 2.19 (3H, s), 3.67 (3H, s), 4.96 (1H, br), 5.37 (1H, s), 6.80-7.05 (8H, m)

REFERENCE PRODUCTION EXAMPLE 17

300 mg of the compound shown by the formula (xvi) was dissolved 2 ml of N,N-dimethylformamide, added 200 mg of N-bromosuccinimide to the solution under ice-cooling, and then the mixture was stirred at 0° C. for one hour. After that, water was added to the reaction mixture, and extracted with ethyl acetate. The organic layer was successively washed with diluted hydrochloric acid, water and saturated brine, dried over magnesium sulfate, and concentrated under reduced pressure. The residue was recrystallized to obtain 340 mg of the compound shown by the formula (xvii).

$^1$H-NMR (CDCl$_3$, TMS) δ (ppm): 2.22 (3H, s), 3.64 (3H, s), 4.69 (1H, br), 6.79-6.92 (8H, m)

REFERENCE PRODUCTION EXAMPLE 18

690 mg of the compound shown by the formula (viii):

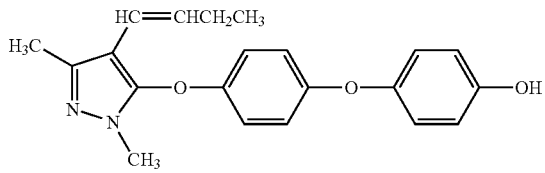

(viii)

was dissolved 10 ml of ethyl acetate, to the solution was added 140 mg of 10% palladium-carbon, and then the mixture was stirred vigorously under hydrogen atmosphere at room temperature for five hours. After that ethyl acetate was added to the reaction mixture, and was filtered. Filtrate was concentrated under reduced pressure. The residue was subjected to silica gel column chromatography to obtain 690 mg of the compound shown by the formula (xviii).

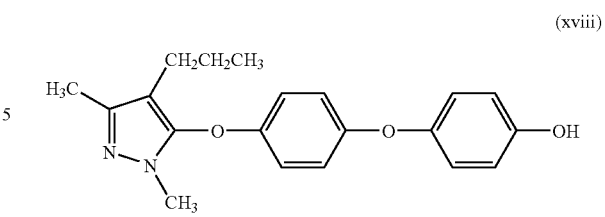

(xviii)

$^1$H-NMR (CDCl$_3$, TMS) δ (ppm): 0.83 (3H, t), 1.40 (2H, m), 2.16 (2H, t), 2.19 (3H, s), 3.56 (3H, s), 5.34 (1H, br), 6.79-6.90 (8H, m)

REFERENCE PRODUCTION EXAMPLE 19

200 mg of the compound shown by the formula (xvi) was dissolved 2 ml of N,N-dimethylformamide, added 110 mg of N-chlorosuccinimide to the solution under ice-cooling, and then the mixture was stirred at room temperature for ten hours. After that water was added to the reaction mixture, and extracted with ethyl acetate. The organic layer was successively washed with diluted hydrochloric acid, water and saturated brine, dried over magnesium sulfate, and concentrated under reduced pressure. The residue was recrystallized to obtain 190 mg of the compound shown by the formula (xix).

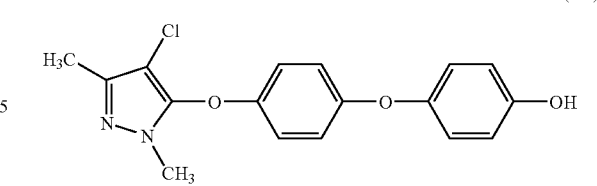

(xix)

$^1$H-NMR (CDCl$_{31}$, TMS) δ (ppm): 2.22 (3H, s), 3.63 (3H, s), 4.82 (1H, br), 6.77-6.92 (8H, m)

REFERENCE PRODUCTION EXAMPLE 20

120 mg of the compound shown by the formula (xvi) was dissolved 2 ml of N,N-dimethylformamide, added 110 mg of N-iodosuccinimide to the solution under ice-cooling, and then the mixture was stirred at 0° C. for three hours. After that, water was added to the reaction mixture, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 180 mg of the compound shown by the formula (xx).

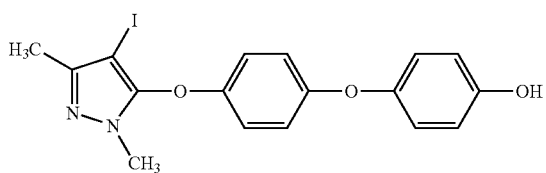

$^1$H-NMR (CDCl$_3$, TMS) δ (ppm): 2.23 (3H, s), 3.67 (3H, s), 4.74 (1H, br), 6.79-6.93 (8H, m)

REFERENCE PRODUCTION EXAMPLE 21

400 mg of the compound shown by the formula (xxv):

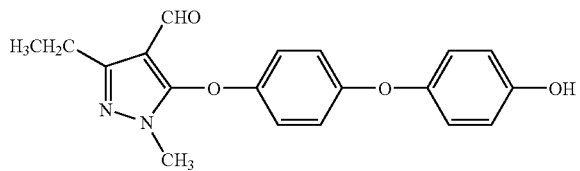

was dissolved to 5 ml of di (ethylene glycol), 90 mg of hydrazine hydrate and 150 mg of potassium hydroxide were added, and then stirred at 80° C. for ten minutes, and at 180° C. for one hour. After that the reaction mixture was acidified by adding diluted hydrochloric acid, and extracted by ethyl acetate. The organic layer was successively washed with water and saturated brine, dried over magnesium sulfate, and concentrated under reduced pressure. The residue was subjected to silica gel column chromatography to obtain 340 mg of the compound shown by the formula (xxi).

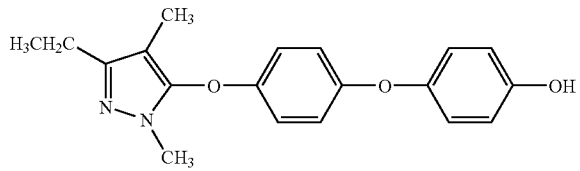

$^1$H-NMR (CDCl$_3$, TMS) δ (ppm): 1.23 (3H, t), 1.77 (3H, s), 2.57 (2H, q), 3.58 (3H, s), 4.80 (1H, br), 6.77-6.91 (8H, m)

REFERENCE PRODUCTION EXAMPLE 22

500 mg of the compound shown by the formula (xxvi):

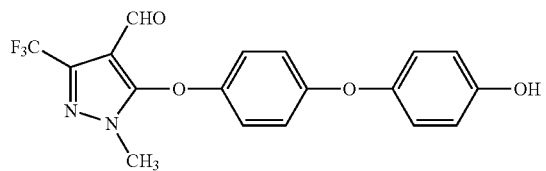

was dissolved to 5 ml of di (ethylene glycol), 130 mg of hydrazine hydrate and 160 mg of potassium hydroxide were added, and then stirred at 80° C. for ten minutes, and at 180° C. for one hour. After that the reaction mixture was acidified by adding diluted hydrochloric acid, and extracted by ethyl acetate. The organic layer was successively washed with water and saturated brine, dried over magnesium sulfate, and concentrated under reduced pressure. The residue was subjected to silica gel column chromatography to obtain 140 mg of the compound shown by the formula (xxii).

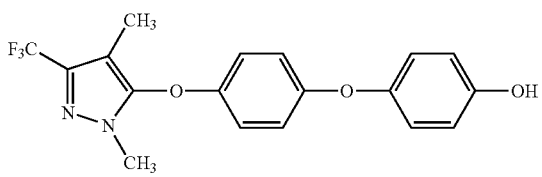

$^1$H-NMR (CDCl$_3$, TMS) δ (ppm): 1.91 (3H, s), 3.70 (3H, s), 4.80 (1H, br), 6.77-6.98 (8H, m)

REFERENCE PRODUCTION EXAMPLE 23

200 mg of the compound shown by the formula (xxvii):

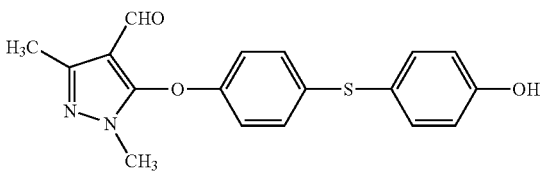

was dissolved to 5 ml of di (ethylene glycol), 60 mg of hydrazine hydrate and 70 mg of potassium hydroxide were added, and then stirred at 80° C. for one hour, and at 180° C. for one hour. After that the reaction mixture was acidified by adding diluted hydrochloric acid, and extracted by ethyl acetate. The organic layer was successively washed with water and saturated brine, dried over magnesium sulfate, and concentrated under reduced pressure. The residue was subjected to silica gel column chromatography to obtain 130 mg of the compound shown by the formula (xxiii).

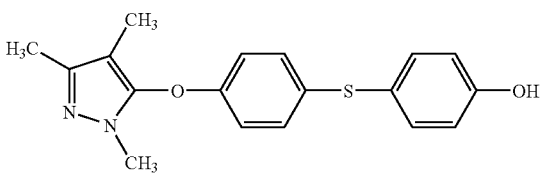

$^1$H-NMR (CDCl$_3$, TMS) δ (ppm): 1.74 (3H, s), 2.17 (3H, s), 3.55 (3H, s), 5.32 (1H, br), 6.78-6.82 (4H, m), 7.17-7.19 (2H, m), 7.30-7.32 (2H, m)

REFERENCE PRODUCTION EXAMPLE 24

200 mg of the compound shown by the formula (xxviii):

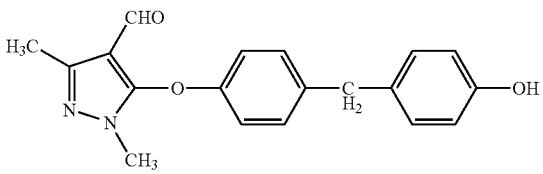

was dissolved to 5 ml of di (ethylene glycol), 60-mg of hydrazine hydrate and 70 mg of potassium hydroxide were added, and then stirred at 80° C. for one hour, and at 180° C. for one hour. After that the reaction mixture was acidified by adding diluted hydrochloric acid, and extracted by ethyl acetate. The organic layer was successively washed with water and saturated brine, dried over magnesium sulfate, and concentrated under reduced pressure. The residue was subjected to silica gel column chromatography to obtain 150 mg of the compound shown by the formula (xxiv).

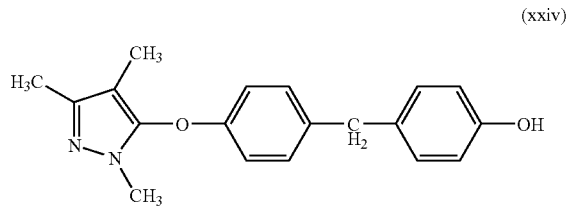

(xxiv)

$^1$H-NMR (CDCl$_3$, TMS) δ (ppm): 1.74 (3H, s), 2.17 (3H, s), 3.55 (3H, s), 3.86 (2H, s), 5.00 (1H, br), 6.74-6.81 (4H, m), 7.02-7.10 (4H, m)

REFERENCE PRODUCTION EXAMPLE 25

500 mg of 4,4'-dihydroxybiphenylether was dissolved to 5 ml of N,N-dimethylformaide, 200 mg of sodium hydride (60% in oil) was added to the solution under ice-cooling, and then the mixture was stirred at room temperature for ten minutes. After that, to the said mixture was added 5 ml of N,N-dimethylformamide solution of 410 mg of 5-chloro-3-ethyl-1-methyl-1H-pyrazol-4-carbaldehyde shown by the formula:

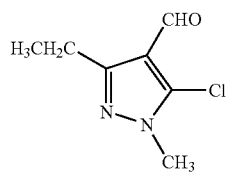

over ten minutes at 70° C., and then the mixture was stirred at 70° C. for two hours. After that, water and 10% hydrochloric acid were added to the reaction mixture which was cooled to room temperature, and extracted with ethyl acetate. The organic layer was successively washed with water and saturated brine, dried over magnesium sulfate, and concentrated under reduced pressure. The residue was subjected to silica gel column chromatography to obtain 460 mg of the compound shown by the formula (xxv).

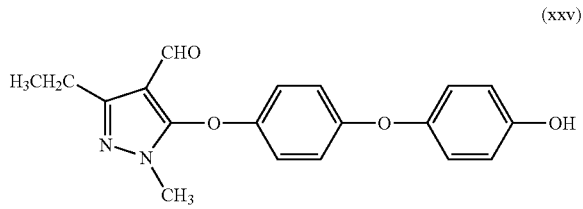

(xxv)

$^1$H-NMR (CDCl$_3$, TMS) δ (ppm): 9.51 (1H, s), 6.79-6.94 (8H, m), 5.44 (1H, s), 3.66 (3H, s), 2.86 (2H, q), 1.27 (3H, t)

REFERENCE PRODUCTION EXAMPLE 26

570 mg of 4,4'-dihydroxybiphenylether was dissolved to 5 ml of N,N-dimethylformaide, 170 mg of sodium hydride (60% in oil) was added to the solution under ice-cooling, and then the mixture was stirred at room temperature for ten minutes. After that, to the said mixture was added 5 ml of N,N-dimethylformamide solution of 570 mg of 5-chloro-1-methyl-3-trifluoromethyl-1H-pyrazol-4-carbaldehyde shown by the formula:

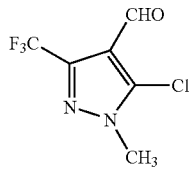

over ten minutes at 70° C., and then the mixture was stirred at 70° C. for two hours. After that, water and 10% hydrochloric acid were added to the reaction mixture which was cooled to room temperature, and extracted with ethyl acetate. The organic layer was successively washed with water and saturated brine, dried over magnesium sulfate, and concentrated under reduced pressure. The residue was subjected to silica gel column chromatography to obtain 440 mg of the compound shown by the formula (xxvi).

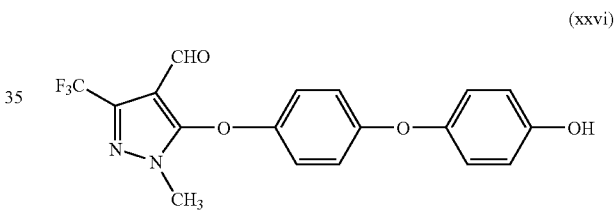

(xxvi)

$^1$H-NMR (CDCl$_3$, TMS) δ (ppm): 9.66 (1H, s), 6.79-6.93 (8H, m), 4.95 (1H, s), 3.81 (3H, s)

REFERENCE PRODUCTION EXAMPLE 27

0.4 g of sodium hydride (60% in oil) was suspended to 15 ml of N,N-dimethylformamide, 1.5 g of 4,4'-tiodiphenol shown by the formula:

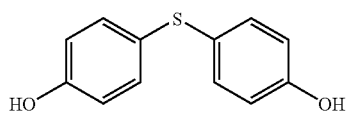

was added at room temperature, and then the mixture stirred at 70° C. for one hour. After that, to the said mixture was added 5 ml of N,N-dimethylformamide solution of 1.0 g of 5-chloro-1,3-dimethyl-1H-pyrazole-4-carbaldehyde over ten minutes at 70° C., and then the mixture was stirred at 70° C. for eight hours. After that, aqueous solution of saturated ammonium chloride was added to the reaction mixture which was cooled to room temperature, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 1.8 g of the compound shown by the formula (xxvii).

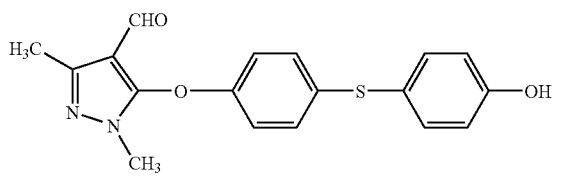

1H-NMR (CDCl$_3$, TMS) δ (ppm): 2.45 (3H, s), 3.63 (3H, s), 6.82-6.90 (4H, m), 7.15-7.36 (4H, m), 9.53 (1H, s)

REFERENCE PRODUCTION EXAMPLE 28

0.4 g of sodium hydride (60% in oil) was suspended to 15 ml of N,N-dimethylformamide, 1.3 g of bis(4-hydroxyphenyl)methane was added at room temperature, and then the mixture stirred at 70° C. for two hours. After that, to the said mixture was added 5 ml of N,N-dimethylformamide solution of 1.0 g of 5-chloro-1,3-dimethyl-1H-pyrazole-4-carbaldehyde over ten minutes at 70° C., and then the mixture was stirred at 70° C. for seven hours. After that, aqueous solution of saturated ammonium chloride was added to the reaction mixture which was cooled to room temperature, and extracted with ethyl acetate. The organic layer was successively washed with diluted hydrochloric acid, water and saturated brine, dried over magnesium sulfate, and concentrated under reduced pressure. The residue was subjected to silica gel column chromatography to obtain 1.2 g of the compound shown by the formula (xxviii).

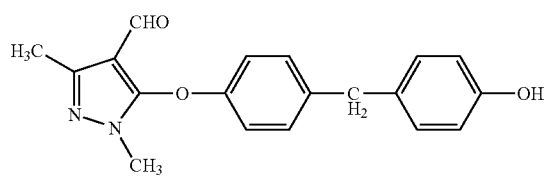

$^1$H-NMR (CDCl$_3$, TMS) δ (ppm): 2.45 (3H, s), 3.63 (3H, s), 3.88 (2H, s), 6.75-6.78 (2H, m), 6.90-6.92 (2H, m), 7.02-7.04 (2H, m), 7.13-7.15 (2H, m), 9.51 (1H, s)

REFERENCE PRODUCTION EXAMPLE 29

200 g of 1,3-dimethyl-5-pyrazolone was dissolved to 156 g of N,N-dimethylformamide. 629 g of phosphorous oxychloride was added to the mixture at room temperature, and then stirred at 90° C. for three hours. After the reaction mixture was cooled to room temperature, the reaction mixture was poured into water, and extracted with ethyl acetate.

The organic layer was successively washed with water, saturated aqueous solution of sodium hydrogen carbonate, and saturated brine, dried over magnesium sulfate, and concentrated under reduced pressure to obtain 223 g of 5-chloro-1,3-dimethyl-1H-pyrazole-4-carbaldehyde.

$^1$H-NMR (CDCl$_3$, TMS) δ (ppm): 2.45 (3H, s), 3.84 (3H, s), 9.86 (1H, s)

Next, formulation examples are described below. Parts represent parts by weight.

FORMULATION EXAMPLE 1

10 parts of each of the present invention compounds (1) to (30) is dissolved in 35 parts of xylene and 35 parts of N,N-dimethylformamide, and 14 parts of polyoxyethylene styryl phenyl ether and 6 parts of calcium dodecylbenzenesulfonate are added thereto, followed by well stirring and mixing, to give 10% emulsifiable concentrate for each compound.

FORMULATION EXAMPLE 2

20 parts of each of the present invention compounds (1) to (30) is added to a mixture containing 4 parts of sodium laurylsulfate, 2 parts of calcium lignin sulfonate, 20 parts of synthetic hydrated silicone oxide fine powder, and 54 parts of diatomaceous earth, followed by well stirring and mixing, to give 20% wettable powder for each compound.

FORMULATION EXAMPLE 3

To 2 parts of each of the present invention compounds (1) to (30) are added 1 part of synthetic hydrated silicon oxide fine powder, 2 parts of calcium lignin sulfonate, 30 parts of bentonite, and 65 parts of kaolin clay, followed by well stirring and mixing, and an appropriate amount of water is added to this mixture, followed by further stirring, granulation with a granulator, and air drying, to give 2% granule for each compound.

FORMULATION EXAMPLE 4

1 part of each of the present invention compounds (1) to (30) is dissolved in an appropriate amount of acetone, and parts of synthetic hydrated silicon oxide fine powder, 0.3 part of PAP, and 93.7 parts of Fubasami clay are well stirring and mixing, and acetone is removed by evaporation from the mixture, to give 1% dust for each compound.

FORMULATION EXAMPLE 5

10 parts of each of the present invention compounds (1) to (30), 35 parts of white carbon containing 50 parts of polyoxyethylene alkyl ether sulfate ammonium salt, and 55 parts of water are mixed and pulverized by the wet grinding method to give 10% flowable for each compound.

FORMULATION EXAMPLE 6

0.1 part of each of the present invention compounds (1) to (30) is dissolved in a mixture of 5 parts of xylene and 5 parts of trichloroethane, and the resulting solution is mixed with 89.9 parts of deodorized kerosene to give 0.1% oil solution.

FORMULATION EXAMPLE 7

10 mg of each of the present invention compounds (1) to (30) is dissolved in 0.5 ml of acetone, the solution is applied to 5 g of powdery solid animal food (powdery solid animal food for bleeding CE-2; a product of CLEA Japan, Inc.) and mixed uniformly, and acetone is removed by evaporation from the mixture, to give a poison bait for each compound.

The following test example will demonstrate the noxious arthropod pests controlling activity of the compound of the present invention.

TEST EXAMPLE 1

The formulation obtained according to Formulation Example 1 using the present invention compounds (1) to (30) and the comparative compound (a) described below respectively, was diluted with water so that the concentration of the present invention compound or the comparative compound came to 200 ppm.

About twenty female adults of *Tetranychus urticae* were set free on brush bean (*Phaseolus vulgaris*) in the primary leaf stage, which had been potted in a plastic cup for 7 days after the seeding. After 1 day, a 30 ml of the diluted formulation described-above was sprayed over the plant. On the 8th and 13th day after the application, the numbers of lived *Tetranychus urticae* on the leaf of brush bean plant were examined, and the Controlling Rates were calculated by the following scheme.

Controlling Rate=100×{1−(a number of lived *Tetranychus urticae* in the treatment)/(a number of lived *Tetranychus urticae* in the non-treatment)}

As a result, in the treatment of the present invention compounds (1) to (30), all of the Controlling rates were not less than 90% on 8th day and 13th day after the application.

On the other hand, in the treatment of the comparative compound (a), the Controlling rates were less than 30% on 8th day and 13th day after the application.

Comparative compound (a)

(a)

which is disclosed as the Compound No. 189 in the Japan Laid-Open Patent specification sho 63-183564A, p. 21.

TEST EXAMPLE 2

The formulation obtained according to Formulation Example 1 using the present invention compound (25):

(25)

and the comparative compound (b) described below respectively, was diluted with water so that the concentration of the present invention compound or the comparative compound came to 200 ppm.

30 ml of the diluted formulation described above was sprayed over the seedling of apple, which had been potted in plastic cup for 28 days after seeding about 15 cm height. After the sprayed solution was dried, about sixty first-instar larvae of *Adoxophyes orana fasciata* were set free on the apple seedling. On the 7 th day after application, the number of surviving or dyed *Adoxophyes orana fasciata* on the apple seedling was examined, and the rate of dead pests was calculated.

As a result, in the treatment of the present invention compound (25), the rate of dead pests was 90% or more. On the other hand, in the treatment of the comparative compound (b), the rate of dead pests was less than 80%.

Comparative compound (b)

(b)

which is disclosed as the Compound No. 23 in the Japan Laid-Open Patent specification sho 62-53970A, p. 3.

INDUSTRIAL APPLICABILITY

The compound of the present invention is useful to control pests.

The invention claimed is:

1. A pyrazole compound represented by the formula (a):

(a)

wherein, $R^1$ represents a hydrogen atom, a C1 to C4 alkyl group or a trifluoromethyl group;

$R^2$ represents a C1 to C4 alkyl group;

$R^3$ represents a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group, a halogen atom or a cyano group;

$R^4$ represents a halogen atom, a C1 to C3 alkyl group, a C1 to C3 alkoxy group, a C1 to C3 haloalkyl group or a C1 to C3 haloalkoxy group;

m represents an integer of 0 to 4 and when m is an integer of 2 to 4, each of $R^4$s may be the same or different;

$R^5$ represents a halogen atom, a C1 to C3 alkyl group, a C1 to C3 alkoxy group, a C1 to C3 haloalkyl group or a C1 to C3 haloalkoxy group;

n represents an integer of 0 to 4 and when n is an integer of 2 to 4, each of $R^5$s may be the same or different;

each of $R^6$ and $R^7$ may be the same or different and represents a hydrogen atom, a halogen atom or a methyl group;

Q represents an oxygen atom, a sulfur atom or a C1 to C5 alkylidene.

2. The pyrazole compound according to claim 1, wherein
R¹ is a C1 to C4 alkyl group or a trifluoromethyl group;
R² is a C1 to C4 alkyl group;
R³ is a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group or a cyano group;
R⁴ is a halogen atom, a C1 to C3 alkyl group, a C1 to C3 alkoxy group, a C1 to C3 haloalkyl group or a C1 to C3 haloalkoxy group;
m is an integer of 0 to 4 and when m is an integer of 2 to 4, each of R⁴s may be the same or different;
R⁵ is a halogen atom, a C1 to C3 alkyl group, a C1 to C3 alkoxy group, a C1 to C3 haloalkyl group or a C1 to C3 haloalkoxy group;
n is an integer of 0 to 4 and when n is an integer of 2 to 4, each of R⁵s may be the same or different;
each of R⁶ and R⁷ may be the same or different and is a hydrogen atom, a halogen atom or a methyl group;
Q represents an oxygen atom in the formula (a).

3. The pyrazole compound according to claim 1, wherein R³ is a C1 to C6 alkyl group, a C1 to C6 haloalkyl group, a C2 to C6 alkenyl group or a C2 to C6 alkynyl group in the formula (a).

4. The pyrazole compound according to claim 1, wherein R³ is a halogen atom in the formula (a).

5. The pyrazole compound according to claim 1, wherein R¹ is a C1 to C4 alkyl group or trifluoromethyl group in the formula (a).

6. The pyrazole compound according to claim 1, wherein R¹ is a methyl group in the formula (a).

7. The pyrazole compound according to claim 1, wherein Q is an oxygen atom in the formula (a).

8. The pyrazole compound according to claim 1, wherein m is an integer of 0 in the formula (a).

9. The pyrazole compound according to claim 1, wherein n is an integer of 0 in the formula (a).

10. The pyrazole compound according to claim 1, wherein m is an integer of 0 and n is an integer of 0 in the formula (a).

11. The pyrazole compound according to claim 1, wherein R⁶ and R⁷ are chlorine atoms in the formula (a).

12. A noxious arthropod pests controlling composition comprising the pyrazole compound according to claim 1 as an active ingredient and an inert carrier.

13. A method for controlling noxious arthropod pests comprising applying an effective amount of the pyrazole compound according to claim 1 to noxious arthropod pests or habitat noxious arthropod pests.

14. A compound of formula (b):

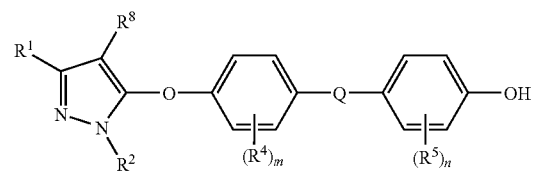

wherein,
R¹ represents a hydrogen atom, a C1 to C4 alkyl group or a trifluoromethyl group;
R² represents a C1 to C4 alkyl group;
R⁸ represents a hydrogen atom, a C1 to C6 alkyl group, a C1 to C6 haloalkyl group, a C2 to C6 alkenyl group, a C2 to C6 haloalkenyl group, a C2 to C6 alkynyl group, a C2 to C6 haloalkynyl group, a C1 to C5 hydroxyalkyl group, a C2 to C6 alkoxyalkyl group, a C2 to C6 alkoxycarbonyl group, a C4 to C6 alkenyloxycarbonyl group, a C4 to C6 haloalkenyloxycarbonyl group, a carboxyl group, a halogen atom or a cyano group;
R⁴ represents a halogen atom, a C1 to C3 alkyl group, a C1 to C3 alkoxy group, a C1 to C3 haloalkyl group or a C1 to C3 haloalkoxy group;
m represents an integer of 0 to 4 and when m is an integer of 2 to 4, each of R⁴s may be the same or different;
R⁵ represents a halogen atom, a C1 to C3 alkyl group, a C1 to C3 alkoxy group, a C1 to C3 haloalkyl group or a C1 to C3 haloalkoxy group;
n represents an integer of 0 to 4 and when n is an integer of 2 to 4, each of R⁵s may be the same or different;
Q represents an oxygen atom, a sulfur atom or a C1 to C5 alkylidene group.

15. The compound according to claim 14, wherein R⁸ is a C1 to C6 alkyl group, a C2 to C6 alkenyl group, a C2 to C6 alkynyl group or a halogen atom in the formula (b).

* * * * *